US012807685B2

(12) United States Patent
Nordenfelt et al.

(10) Patent No.: US 12,807,685 B2
(45) Date of Patent: Nov. 24, 2026

(54) ANTIBODIES AGAINST STREPTOCOCCAL M PROTEIN

(71) Applicant: Aventera Antibodies AB, Lund (SE)

(72) Inventors: Bill Pontus Nordenfelt, Lund (SE); Anders Johan Malmström, Uppsala (SE); Wael Gabriel Bahnan, Uppsala (SE); Lotta Johanna Oksanen Happonen, Uppsala (SE); Hamed Khakzad, Uppsala (SE); Oonagh Shannon, Uppsala (SE); Lars Henrik Björck, Uppsala (SE); Lars Gustav Malmström, Uppsala (SE)

(73) Assignee: Aventera Antibodies AB, Lund (SE)

( * ) Notice: Subject to any disclaimer, the term of this patent is extended or adjusted under 35 U.S.C. 154(b) by 613 days.

(21) Appl. No.: 18/245,884

(22) PCT Filed: Sep. 20, 2021

(86) PCT No.: PCT/EP2021/075789

§ 371 (c)(1),
(2) Date: Mar. 17, 2023

(87) PCT Pub. No.: WO2022/058584

PCT Pub. Date: Mar. 24, 2022

(65) Prior Publication Data

US 2024/0010712 A1 Jan. 11, 2024

(30) Foreign Application Priority Data

Sep. 18, 2020 (EP) .................................... 20196885

(51) Int. Cl.
*C07K 16/1275* (2026.01)
*A61K 39/00* (2006.01)
*A61P 31/04* (2006.01)

(52) U.S. Cl.
CPC .......... *C07K 16/1275* (2013.01); *A61P 31/04* (2018.01); *A61K 2039/505* (2013.01);
(Continued)

(58) Field of Classification Search
CPC ............ C07K 16/1275; C07K 2317/31; C07K 2317/54; C07K 2317/565; A61P 31/04; A61K 2039/505
See application file for complete search history.

(56) References Cited

U.S. PATENT DOCUMENTS

| | | | | |
|---|---|---|---|---|
| 8,466,263 B2 * | 6/2013 | Marasco | ............ | A61K 51/1075 424/134.1 |
| 11,603,405 B2 * | 3/2023 | Gaudet | .................. | A61P 35/00 |

FOREIGN PATENT DOCUMENTS

| | | |
|---|---|---|
| WO | WO 2019/218022 A1 | 11/2019 |
| WO | WO 2022/058584 A1 | 3/2022 |

OTHER PUBLICATIONS

Rosenstein et al. (2020). "Production of F(ab')2 from Monoclonal and Polyclonal Antibodies". Current Protocols in Molecular Biology, 131(1):e119. (Year: 2020).*

(Continued)

*Primary Examiner* — Samira J Jean-Louis
*Assistant Examiner* — Bailey M Morgan
(74) *Attorney, Agent, or Firm* — Weston R. Gould; DINSMORE & SHOHL LLP

(57) ABSTRACT

Provided herein are antibodies and antibody compositions. Also provided are method for obtaining such antibodies and methods for using such antibodies and compositions for treating bacterial and viral infections and for research and screening purposes. The antibodies and compositions can affect the immune system and inhibiting pathogenic infections including streptococcal infections.

7 Claims, 39 Drawing Sheets

Specification includes a Sequence Listing.

(52) U.S. Cl.
CPC ...... *C07K 2317/21* (2013.01); *C07K 2317/54* (2013.01); *C07K 2317/565* (2013.01); *C07K 2317/76* (2013.01); *C07K 2317/92* (2013.01)

(56) References Cited

OTHER PUBLICATIONS

Rudikoff et al. "Single amino acid substitution altering antigen-binding specificity", Mar. 1982, Proceedings of the National Academies of Sciences, vol. 79, p. 1979-1983. (Year: 1982).*
MacCallum et al. "Antibody-antigen Interactions: Contact Analysis and Binding Site Topography", 1996, Journal of Molecular Biology, vol. 262, p. 732-745. (Year: 1996).*
Pascalis et al. "Grafting of "Abbreviated" Complementarity-Determining Regions Containing Specificity-Determining Residues Essential for Ligand Contact to Engineer a Less Immunogenic Humanized Monoclonal Antibody", 2002, The Journal of Immunology, p. 3076-3084 (Year: 2002).*
Casset et al. "A peptide mimetic of an anti-CD4 monoclonal antibody by rational design" 2003, Biochemical and Biophysical Research Communications, vol. 307, p. 198-205. (Year: 2003).*
Vajdos et al. "Comprehensive Functional Maps of the Antigen-binding Site of an Anti-ErbB2 Antibody Obtained with Shotgun Scanning Mutagenesis", 2002, Journal of Molecular Biology, vol. 320, p. 415-428. (Year: 2002).*
Patterson, MJ. *Streptococcus*. In: Baron S, editor. Medical Microbiology. 4th edition. Galveston (TX): University of Texas Medical Branch at Galveston; 1996. Chapter 13. (Year: 1996).*
Addgenene, General Transfection, https://www.addgene.org/protocols/transfection/, retrieved on Mar. 15, 2023.
Ahnilde et al., A Predictive Model of Antibody Binding in the Presence of IgG-Interacting Bacterial Surface Proteins, Frontiers in Immunology, vol. 12, Article 629103, 2021.
Akesson et al., Protein H—a novel IgG binding bacterial protein, Molecular Immunology 27(6), pp. 523-531, 1990.
Akesson et al., M1 protein and protein H: IgGFc- and albumin-binding streptococcal surface proteins encoded by adjacent genes, The Biochemical Journal 300 ( Pt 3), pp. 877-886, 1994.
Azure et al., Recent advances in the development of peptide vaccines and their delivery systems against group A *Streptococcus*, Vaccines 7(3), 2019, Azuar et al.
Bakalar et al., Size-Dependent Segregation Controls Macrophage Phagocytosis of Antibody-Opsonized Targets, Cell 174(1), p. 131-142.e13, 2018.
Bournazos et al., Signaling by antibodies: recent progress, Annual Review of Immunology 35, pp. 285-311., 2017.
Calarese et al., Dissection of the carbohydrate specificity of the broadly neutralizing anti-HIV-1 antibody 2G12, Proc. Natl. Acad. Sci. USA 102, 13372-13377., 2005.
Carapetis et al., The global burden of group A streptococcal diseases, The Lancet Infectious Diseases 5(11), pp. 685-694, 2005.
Carlsson et al., Evasion of phagocytosis through cooperation between two ligand-binding regions in *Streptococcus pyogenes* M protein, The Journal of Experimental Medicine 198(7), pp. 1057-1068, 2003.
Carlsson et al., Human fibrinogen bound to *Streptococcus pyogenes* M protein inhibits complement deposition via the classical pathway, Molecular Microbiology 56(1), pp. 28-39, 2005.
Cedervall et al., Allosteric and temperature effects on the plasma protein binding by streptococcal M protein family members, Scandinavian Journal of Immunology 42(4), pp. 433-441.
Collin et al., EndoS, a novel secreted protein from *Streptococcus pyogenes* with endoglycosidase activity on human IgG., The EMBO Journal 20(12), pp. 3046-3055, 2001.
Collin et al., Generation of a mature streptococcal cysteine proteinase is dependent on cell wall-anchored M1 protein, Molecular Microbiology 36(6), pp. 1306-1318, 2000.
Dale et al., Update on group A streptococcal vaccine development, Current Opinion in Infectious Diseases, vol. 33, No. 3, pp. 244-250, 2020.
Freeman et al., Transmembrane Pickets Connect Cyto- and Pericellular Skeletons Forming Barriers to Receptor Engagement, Cell 172(1-2), p. 305-317.e10, 2018.
Gach et al., Proline is not uniquely capable of providing the pivot point for domain swapping in 2G12, a broadly neutralizing antibody against HIV-1, J. Biol. Chem. 285, 10 1122-1127, 2010.
Ghosh, P., Variation, Indispensability, and Masking in the M protein. Trends in Microbiology 26(2), pp. 132-144.
Gray, J.J. 2006. High-resolution protein-protein docking, Current Opinion in Structural Biology 16(2), pp. 183-193, 2018.
Happonen et al., A quantitative *Streptococcus pyogenes*-human protein-protein interaction map reveals localization of opsonizing antibodie, Nature Communications 10(1), p. 2727, 2019.
Hattori et al., . Antigen clasping by two antigen-binding sites of an exceptionally specific antibody for histone methylation, Proceedings of the National Academy of Sciences of the United States of America 113(8), pp. 2092-2097, 2016.
Hauri et al., Rapid determination of quaternary protein structures in complex biological samples, Nature Communications 10(1), p. 192.
Herr e tal., Insights into IgA-mediated immune responses from the crystal structures of human FcalphaRI and its complex with IgA1-Fc., Nature 423(6940), pp. 614-620, 2003.
Herwald et al., M protein, a classical bacterial virulence determinant, forms complexes with fibrinogen that induce vascular leakage, Cell 116(3), pp. 367-379, 2004.
Hollands et al., A bacterial pathogen co-opts host plasmin to resist killing by cathelicidin antimicrobial peptides, The Journal of Biological Chemistry 287(49), pp. 40891-40897, 2012.
Johansson et al., Cathelicidin LL-37 in severe *Streptococcus pyogenes* soft tissue infections in humans, Infection and Immunity 76(8), pp. 3399-3404, 2008.
Kadri et al., Impact of Intravenous Immunoglobulin on Survival in Necrotizing Fasciitis With Vasopressor-Dependent Shock: A Propensity Score-Matched Analysis From 130 US Hospitals, Clinical Infectious Diseases 64(7), pp. 877-885, 2017.
Kanyavuz et al., Breaking the law: unconventional strategies for antibody diversification. Nature Reviews. Immunology 19(6), pp. 355-368, 2019.
Karami et al., DaReUS-Loop: a web server to model multiple loops in homology models. Nucleic Acids Research 47(W1), pp. W423-W428, 2019.
Klein et al., Few and far between: how HIV may be evading antibody avidity, PLoS Pathogens 6(5), p. e1000908., 2010.
Kline et al., Bacterial adhesins in host-microbe interactions. Cell Host & Microbe 5(6), pp. 580-592, 2009.
Koehler et al., Macromolecular modeling and design in rosetta: new methods and frameworks, 2019.
Kong et al., Molecular recognition of HIV glycans by antibodies, in HIV Glycans in Infection and Immunity, R. Pantophlet, ed. (New York, NY: Springer New York), pp. 117-141, 2014.
Kontermann et al., Bispecific antibodies, Drug Discovery Today 20(7), pp. 838-847., 2015.
Kurosaki et al., Memory B cells, Nature Reviews Immunology 15(3), pp. 149-159, 2015.
Laabei et al., Catch Me if You Can: *Streptococcus pyogenes* Complement Evasion Strategies, Journal of/nnate Immunity 11(1), pp. 3-12, 2019.
Linner et al., Clinical efficacy of polyspecific intravenous immunoglobulin therapy in patients with streptococcal toxic shock syndrome: a comparative observational study, Clinical Infectious Diseases 59(6), pp. 851-857, 2014.
Lu et al., Beyond binding: antibody effector functions in infectious diseases, Nature Reviews. Immunology 18(1), pp. 46-61, 2018.
Macheboeuf et al., Streptococcal M1 protein constructs a pathological host fibrinogen network, Nature 472(7341), pp. 64-68, 2011.
Madsen et al., Immunoglobulin G for patients with necrotising soft tissue infection (Instinct): a randomised, blinded, placebo- controlled trial. Intensive Care Medicine 43(11), pp. 1585-1593, 2017.

(56) References Cited

OTHER PUBLICATIONS

Mitchell, T.J., The pathogenesis of streptococcal infections: from tooth decay to meningitis, Nature Reviews, Microbiology 1(3), pp. 219-230, 2003.
Mitsi et al., Agglutination by anti-capsular polysaccharide antibody is associated with protection against experimental human pneumococcal carriage. Mucosa/ Immunology 10(2), pp. 385-394, 2017.
Moor et al., High-avidity IgA protects the intestine by enchaining growing bacteria, Nature 544(7651), pp. 498-502, 2017.
Motley et al., Monoclonal antibody-based therapies for bacterial infections, Current Opinion in Infectious Diseases 32(3), pp. 210-216, 2019.
De Neergaard et al., High-sensitivity assessment of phagocytosis by persistent association-based normalization. BioRxiv, 2016.
Nordenfelt et al., Phagosome dynamics during phagocytosis by neutrophils. Journal of Leukocyte Biology 90(2), pp. 271-284, 2011.
Nordenfelt et al., Antibody orientation at bacterial surfaces is related to invasive infection. The Journal of Experimental Medicine 209(13), pp. 2367-2381, 2012.
Okumura et al., Subterfuge and sabotage: evasion of host innate defenses by invasive gram-positive bacterial pathogens. Annual Review of Microbiology 68, p. 439-458, 2014.
Oliver et al., Group A *Streptococcus pharyngitis* and pharyngeal carriage: A meta-analysis, PLoS Neglected Tropical Diseases 12(3), p. e0006335, 2018.
Ozberk et al., Contribution of cryptic epitopes in designing a group A streptococcal vaccine. Human vaccines & immunotherapeutics 14(8), pp. 2034-2052, 2018.
Pandey et al., Streptococcal immunity is constrained by lack of immunological memory following a single episode of pyoderma, PLoS Pathogens 12(12), p. e1006122, 2016.
Parks et al., Polyspecific Intravenous Immunoglobulin in Clindamycin-treated Patients With Streptococcal Toxic Shock Syndrome: A Systematic Review and Meta-analysis, Clinical Infectious Diseases 67(9), pp. 1434-1436, 2018.
Pascual et al., Analysis of somatic mutation in five B cell subsets of human tonsil, The Journal of Experimental Medicine 180(1), pp. 329-339, 1994.
Von Pawel-Rammingen et al., a novel streptococcal cysteine proteinase with unique specificity for immunoglobulin G, The EMBO Journal 21(7), pp. 1607-1615, 2002.
Skwarczynski et al., Chemical science (Royal Society of Chemistry: 2010) 7(2), pp. 842-854, 2016.
Smith et al., Rapid generation of fully human monoclonal antibodies specific to a vaccinating antigen, Nature Protocols 4(3), pp. 372-384, 2009.
Sondermann et al., The 3.2-Å crystal structure of the human IgG1 Fc fragment-Fc gammaRIII complex. Nature 406(6793), pp. 267-273, 2000.
Song et al., High-resolution comparative modeling with RosettaCM. Structure 21(10), pp. 1735-1742, 2013.
Spoerry et al., Novel IgG-Degrading Enzymes of the IgdE Protease Family Link Substrate Specificity to Host Tropism of *Streptococcus* Species, Plos One 11(10), p. e0164809, 2016.
Sriskandan et al., Human intravenous immunoglobulin for experimental streptococcal toxic shock: bacterial clearance and modulation of inflammation, The Journal of Antimicrobial Chemotherapy 58(1), pp. 117-124.
Staali et al., *Streptococcus pyogenes* bacteria modulate membrane traffic in human neutrophils and selectively inhibit azurophilic granule fusion with phagosomes, Cellular Microbiology 8(4), pp. 690-703, 2006.
Swanson et al., Shaping cups into phagosomes and macropinosomes, Nature Reviews. Molecular Cell Biology 9(8), pp. 639-649, 2008.
Trkola et al., Human monoclonal antibody 2G12 defines a distinctive neutralization epitope on the gp120 glycoprotein of human immunodeficiency virus type 1. J. Virol. 70, 1100-1108, 1996.
Weineisen et al., Streptococcal MS protein prevents neutrophil phagocytosis by interfering with CD11b/CD18 receptor-mediated association and signaling, Journal of Immunology 172(6), pp. 3798-3807, 2004.
Weitzner et al., Modeling and docking of antibody structures with Rosetta, Nature Protocols 12(2), pp. 401-416, 2017.
Wilson et al., Somatic hypermutation introduces insertions and deletions into immunoglobulin V genes, The Journal of Experimental Medicine 187(1), pp. 59-70, 1998.
Woof et al., Human antibody-Fe receptor interactions illuminated by crystal structures, Nature Reviews Immunology 4(2), pp. 89-99, 2004.
Yan et al., HSYMDOCK: a docking web server for predicting the structure of protein homo-oligomers with Cn or On symmetry, Nucleic Acids Research 46(W1), pp. W423-W431, 2018.
Quinn et al., Autoantibody germ-line gene segment encodes VH and VL regions of a human anti-streptococcal monoclonal antibody recognizing streptococcal M protein and human cardiac myosin epitopes, The Journal of Immunology, vol. 154, pp. 4203-4212, 1995.
Beacheys et al., Repeating Covalent Structure and Protective Immunogenicity of Type 24 Streptococcal M Protein, The Journal of Biological Chemistry, vol. 258, No. 21, pp. 13250-13257, 1983.
Brinkmann et al., The making of bispecific antibodies, MABS, vol. 9, No. 2, pp. 182-212, 2017.
Dondelinger et al., Understanding the Significance and Implications of Antibody Numbering and Antigen-Binding Surface/Residue Definition, Frontiers in Immunology, vol. 9, pp. 1-15, 2018.
Extended European Search Report dated Jun. 24, 2021 in EP Application No. 20196885.6.
Hasty et al., Hybridoma antibodies against protective and nonprotective antigenic determinants of a structurally define polypeptide fragment to streptococcal M protein, J. Exp. Med., vol. 155, pp. 1010-1018, 1982.
International Search Report & Written Opinion mailed Jan. 31, 2022 in International Application No. PCT/EP2021/075789.
Jones et al., The importance of the location of antibody binding on the M6 protein for opsonization and phagocytosis of group A M6 streptococci, The Journal of Experimental Medicine, vol. 167, No. 3, pp. 1114-1123, 1988.
Partial European Search Report dated Mar. 11, 2021 in EP Application No. 20196885.6.
Roche et al., Antibody blocks acquisition of bacterial colonization through agglutination, Mucosal Immunology, vol. 8, No. 1, pp. 176-185, 2014.
Rudikoff et al., Single amino acid substitution altering antigen-binding specificity, Proceedings of the National Academy of Sciences, vol. 79, No. 6, pp. 1979-1983, 1982.

* cited by examiner

Figure 18

```
SEQ ID NO:1   Ab25H   CARSYPHKRWLRPPFDYW----
SEQ ID NO:2   Ab26H   CAKNS-RSGWY-FFFDYWGQ--
SEQ ID NO:3   Ab32H   CARQGFDTRGE-DAFEIWG---
SEQ ID NO:4   Ab49H   CVRD---SRFW-GIFDYWGQGT
                      *.:.   .      *: *
```

```
SEQ ID NO:5   Ab25L   QYNSYPV--TFGQGTKV
SEQ ID NO:6   Ab26L   QYDNLPL--TFGGGTKV
SEQ ID NO:7   Ab32L   QRSGWPSIFTFGPGTKV
SEQ ID NO:8   Ab49L   QRSNWPP--TFGQGTKV
                      * .. *   *** ****
```

Ab overlay

Fab affinity

Figure 38

```
SEQ ID NO:25 M1_B1B2B3   ----------------------------------------------------------------------------------ATALEKELEEKKEALELAIDQASRDYHRATALE  38
SEQ ID NO:26 M1_C1C2C3   ------------------------------------------------------------------------------------------------------------------------  0
SEQ ID NO:27 M1_FL       MDGNFREVIEDLAANHPAIQNIRLRYENKDLKARLENAMEVAGRDFKRAEELERAKQALEDQRRDLETKLKELQQDYDLAKESTSWDRQRLEKELEEKKEALELAIDQASRDYHRATALE  120

             M1_B1B2B3   KELEEKKKALELAIDQASQDYNRANVLEEELE----------------------------------------------------------------------------------------  65
             M1_C1C2C3   ------------------------------------------------------------------AKLEEEKQISDASRQSLRRDLDASREAKKQVEKDLANLTAELDKVKEDKQISDA  54
             M1_FL       KELEEKKKALELAIDQASQDYNRANVLEEELETTITREQEINRNLLSNAELELDQLSSENEQLTIEKAELEEEKQISDASRQSLRRDLDASREAKKQVEKDLANLTAELDKVKEDKQISDA  240

             M1_B1B2B3   ------------------------------------------------------------------------------------------------------------------------  65
             M1_C1C2C3   SRQGLRRDLDASREAKKQVEKDLANLTAELDKVKEEKQISDASRQGLRRDLDASREAKKQVEKALE------------------------------------------------------  120
             M1_FL       SRQGLRRDLDASREAKKQVEKDLANLTAELDKVKEEKQISDASRQGLRRDLDASREAKKQVEKALEEANSKLAALEKLNKELEESKKLTEKEKAELQAKLEAEAKALKEQLAKQAEELAK  360

             M1_B1B2B3   ----------------------------------------------------------------------------------  65
             M1_C1C2C3   ----------------------------------------------------------------------------------  120
             M1_FL       LRAGRASDSQTPDTKPGNKAVPGKGQAPQAGTKPNQNKAPMKETKRQLPSTGETANPFFTAAALTVMATAGVAAVVKRKEEN  442
```

ANTIBODIES AGAINST STREPTOCOCCAL M PROTEIN

PRIORITY AND CROSS REFERENCE TO RELATED APPLICATIONS

This application is the U.S. National Stage Application under 35 U.S.C. § 371 of International Application No. PCT/EP2021/075789, filed Sep. 20, 2021, designating the U.S. and published in the English language as WO 2022/058584 A1 on Mar. 24, 2022, which claims the benefit of European Patent Application No. EP 20196885.6, filed Sep. 18, 2020. Any and all applications for which a foreign or a domestic priority is claimed is/are identified in the Application Data Sheet filed herewith and is/are hereby incorporated by reference in their entirety under 37 C.F.R. § 1.57.

INCORPORATION BY REFERENCE OF MATERIAL IN SEQUENCE LISTING

This application incorporates the material provided in the accompanying text file entitled 2026_06_08_Sequence_Listing_AVEN0002PA.txt, created Jun. 8, 2026, which is 42,534 bytes in size.

I hereby state that the previous "Sequence Listing" that is replaced by the currently submitted replacement "Sequence Listing" in accordance with 37 C.F.R. § 1.825(b) is amended wherein residue 14 of SEQ ID NO: 29 has been updated to glycine (G). I hereby state that the replacement "Sequence Listing", made in accordance with 37 C.F.R. § 1.825(b) is supported in the application, as originally filed at page 3, line 19 reciting that $B_{14}$ is G. I hereby state that the replacement "Sequence Listing", submitted in accordance with 37 C.F.R. § 1.825(b), includes no new matter.

FIELD OF THE INVENTION

The present invention relates to the fields of medical science, immunology and pharmaceutical products. The present invention provides antibodies and compositions capable of affecting the immune system and inhibiting pathogenic infections, such as streptococcal infections. The present invention also provides methods for obtaining such antibodies as well as the uses of such antibodies.

BACKGROUND OF THE INVENTION

Antibodies are essential components of the immune system used to recognize and neutralize external intruders such as pathogenic bacteria. They are produced by B cells after their B cell receptor reacts with a specific antigen in the lymphoid tissue. B cell maturation and antibody development have evolved to allow for an extraordinary variety enabling the binding of diverse targets. V(D)J recombination events, as well as somatic hypermutation, give rise to a vast repertoire of antibody variable domains. The result of B cell activation, clonal expansion, maturation, and class switching is the generation of IgG antibodies that offer long term protection against infectious agents. An IgG antibody is a Y-shaped molecule composed of two identical Fab fragments and one Fc domain, where the unique specificity is provided by Fab interaction with an antigen. IgG typically binds with either Fab and, dependent on the antigen density and organization, can bind with a higher strength through avidity to two copies of the same antigen (Klein and Bjorkman 2010). We designate this latter form of binding as dual-Fab trans binding. When bound to their target, IgG molecules carry out effector functions by triggering clustering of Fc receptors on immune cells, which induces cell signaling and leads to a variety of downstream effects such as phagocytosis, immune recognition, and activation.

Group A *Streptococcus* (GAS) is a common human pathogen causing significant morbidity and mortality in the human population and is an important causative agent of severe invasive infections. The bacterium has evolved an extensive array of measures to counteract the human immune response, including resistance to phagocytosis, and several immunoglobulin-targeting mechanisms (IdeS, EndoS, protein M/H). The streptococcal M protein, a virulence determinant, has a long coiled-coiled structure with repeating regions (A, B, S, C, and D). These regions are typically associated with distinct protein interactions and bind many components of the humoral immune response such as C4BP and albumin, and forms complexes with fibrinogen that induce vascular leakage and contribute to phagocytosis resistance. The M protein can also reduce phagocytosis by reversing the orientation of IgG by capturing IgG Fc domains. These pathogenic mechanisms deprive the immune system of crucial defenses, allowing GAS to disseminate within a host and across the population.

Although GAS infections generate a humoral immune response, repeated exposures seem to be required to generate protective memory B cell immunity. There are few candidates for anti-bacterial monoclonal antibody therapy in general, and none available for GAS. Much effort has been allocated to developing vaccines against GAS (Dale and Walker 2020), with the prime immunizing antigen being M protein, particularly with M protein-based peptides (Azuar et al. 2019). Yet, no effective vaccine against GAS has been approved to date. It is unclear what makes it so difficult to generate immunity, but potentially formation of antibody subsets is suppressed by immunodominant regions or cryptic epitopes (Ozberk et al. 2018). In severe life-threatening invasive GAS infections, intravenous IgG antibodies (IVIG) from human pooled plasma are used as therapy, even though reports on their efficacy show contradictory results. Also, there remain safety issues with medicaments derived from human plasma. Hence, there is a dire need to find new ways to treat these critically ill patients.

Hence, there is a need for effective and safe new antibodies for combatting diseases originating from external intruders such as pathogenic bacteria and vira. One such pathogenic bacterium is Group A *Streptococcus* (GAS).

SUMMARY OF THE INVENTION

The present inventors have discovered that anti-M protein antibodies derived from a healthy donor who had previously undergone a GAS infection, these antibodies when exposed to GAS and M protein bind and exert various effects including a range of protective immune functions, including bacterial agglutination, NFkB activation, phagocytosis, and in vivo protection. The inventors also identified a new type of interaction where the two identical Fabs of one of the monoclonal IgG antibodies simultaneously bind to two distinct epitopes on the same molecule. This form of binding is designated as dual-Fab cis binding.

In a first aspect the present invention provides an antibody binding to streptococcal M protein, wherein said antibody comprises:

A Complementarity Determining Region (CDR) H3 loop comprising the sequence $A_1$-$A_{18}$, (SEQ ID NO:28) wherein $A_1$ is C, $A_2$ is A or V, $A_3$ is R or K, $A_4$ is S, N, Q or D, $A_5$ is Y, S G or absent, $A_6$ is P, F or absent, $A_7$ is H, R, D or absent, $A_8$ is K, S or T, $A_9$ is R or G, $A_{10}$ is W, G or F, $A_{11}$ is L, Y, E or W, $A_{12}$ is R or absent, $A_{13}$ is P, F, D or G, $A_{14}$ is P, F, A or I, $A_{15}$ is F, $A_{16}$ is D or E, $A_{17}$ is Y or I, A18 is W, or the sequence $A_1$-$A_{18}$ comprising no more than 6 conservative substitutions therefrom; and A CDR L3 loop comprising the sequence $B_1$-$B_{17}$, (SEQ ID NO:29) wherein $B_1$ is Q, $B_2$ is Y or R, $B_3$ is N, D or S, $B_4$ is S, N or G, $B_5$ is Y, L or W, $B_6$ is P, $B_7$ is V, L, S or P, $B_8$ is I or absent, $B_9$ is F or absent, $B_{10}$ is T, $B_{11}$ is F, $B_{12}$ is G, $B_{13}$ is Q, G or P, $B_{14}$ is G, $B_{15}$ is T, $B_{16}$ is K, $B_{17}$ is V, or the sequence $B_1$-$B_{17}$ comprising no more than 6 conservative substitutions therefrom.

In one embodiment the antibody is selected from the group consisting of an antibody comprising SEQ ID NO: 9 as the heavy chain and SEQ ID NO: 13 as the light chain, an antibody comprising SEQ ID NO: 10 as the heavy chain and SEQ ID NO: 14 as the light chain, an antibody comprising SEQ ID NO: 11 as the heavy chain and SEQ ID NO: 15 as the light chain, and an antibody comprising SEQ ID NO: 12 as the heavy chain and SEQ ID NO: 16 as the light chain.

In another embodiment the antibody of the present invention binds to streptococcal M protein with a $K_D$ of less than $50\times10^{-9}$ $M^{-1}$, as determined by binding to *Streptococcus pyogenes* SF370.

Antibodies of the present invention have been found to have the ability to mediate bacterial agglutination. In further embodiments the antibodies according to the invention have been found to mediate NFkB-activation. In yet further embodiments of the invention the antibodies of the present invention have been found to have the ability to induce phagocytosis.

In yet further embodiments, antibodies of the present invention have the ability to exhibit simultaneous binding to two different epitopes of the streptococcal M protein by way of dual-Fab cis antibody binding.

In a second aspect the present invention provides a pharmaceutical composition comprising the antibody as defined above and at least one pharmaceutically acceptable excipient.

In one embodiment the pharmaceutical composition comprises two or more different antibodies.

In a third aspect the present invention provides the use of the antibody according to the first aspect for the treatment of a streptococcal infection, such as a Group A *Streptococcus* infection.

In a fourth aspect the present invention provides the use of an antibody of the present invention in an application selected from Western blot, Flow Cytometry, ELISA and Immunoflourescence.

In a fifth aspect the present invention provides an antibody exhibiting binding to two different epitopes of a protein by way of dual-Fab cis antibody binding.

In a sixths aspect the present invention provides a method for obtaining an antibody exhibiting simultaneous binding to two different epitopes of a molecule by way of dual-Fab cis antibody binding, comprising the steps:

obtaining an antibody from a donor which has been exposed to said molecule such as to raise an immune response, cleaving the antibody in single Fab fragments from said antibody by enzymatic reaction, cleaving the antibody F(ab')2-fragments from said antibody by enzymatic reaction, measuring and comparing binding of the intact antibody versus F(ab')2-fragments and single Fab fragments, confirming a significant reduction in single Fab binding as compared to antibody binding, thereby identifying and providing said antibody.

In one embodiment the method for obtaining an antibody exhibiting dual-Fab cis antibody binding, said two different epitopes of a molecule is two different epitopes of a protein, such as streptococcal M protein.

In a seventh aspect the present invention provides a method for crosslinking antibody F(ab')2-fragments bound to a molecule, comprising the steps:

cleaving the antibody F(ab')2-fragments from the antibody by enzymatic reaction, isolating the antibody F(ab')2-fragments, contacting said antibody F(ab')2-fragments and said molecule in a solution, adding disuccinimidylsuberate to said solution and allowing the reaction to proceed, quenching the crosslinking reaction, thereby obtaining the crosslinked antibody F(ab')2-fragments.

In addition, in comparison with known antibodies and antibody compositions, the antibodies according to the present invention show improved properties for effectively exhibiting range of protective immune functions, including bacterial agglutination, NFkB activation, phagocytosis, and/or in vivo protection.

BRIEF DESCRIPTION OF THE DRAWINGS

FIG. 18 shows a multiple sequence alignment reflecting the L3-H3 loop differences on the amino acid sequence level for antibodies Ab25, Ab26, Ab32 and Ab49.

FIG. 38. Sequences of the M protein fragments used.

DETAILED DESCRIPTION

Figure 1:
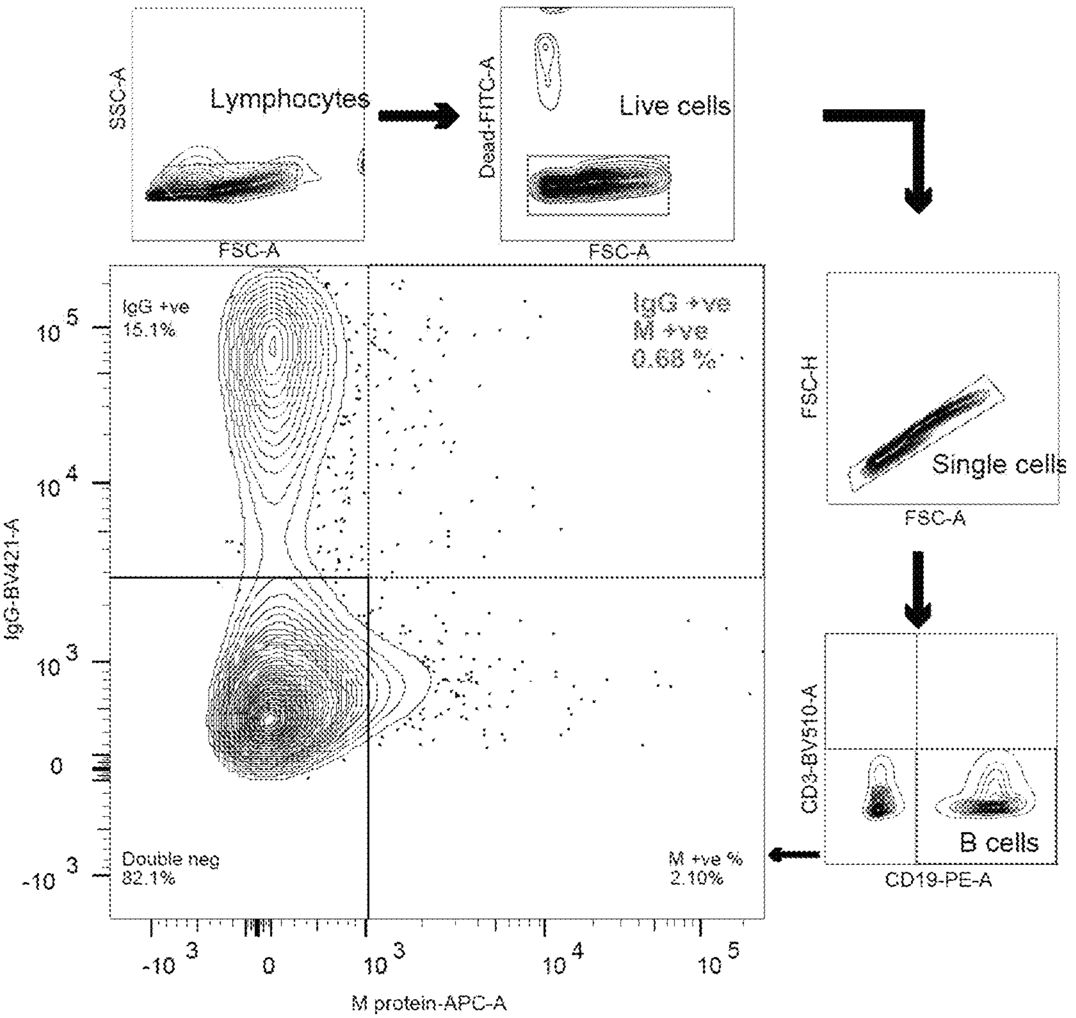
FIG. 1. Illustration of the method for antigen-baiting allowing the development of human single cell-derived M-specific antibodies, where B cells were isolated using Rosettesep B and were FACS sorted into single lymphocytes which were live (Syto9-FITC negative), expressing CD19 (PE), lacking CD3 (BV510) and which were dually positive for IgG and M protein (BV410 and AF647, respectively).

In a first aspect the present invention provides an antibody binding to streptococcal M protein, wherein said antibody comprises:

A Complementarity Determining Region (CDR) H3 loop comprising the sequence $A_1$-$A_{18}$, (SEQ ID NO:28) wherein $A_1$ is C, $A_2$ is A or V, $A_3$ is R or K, $A_4$ is S, N, Q or D, $A_5$ is Y, S G or absent, $A_6$ is P, F or absent, $A_7$ is H, R, D or absent, $A_8$ is K, S or T, $A_9$ is R or G, $A_{10}$ is W, G or F, $A_{11}$ is L, Y, E or W, $A_{12}$ is R or absent, $A_{13}$ is P, F, D or G, $A_{14}$ is P, F, A or I, $A_{15}$ is F, $A_{16}$ is D or E, $A_{17}$ is Y or I, A18 is W, or the sequence $A_1$-$A_{18}$ comprising no more than 6 conservative substitutions therefrom; and A CDR L3 loop comprising the sequence $B_1$-$B_{17}$, (SEQ ID NO:29) wherein $B_1$ is Q, $B_2$ is Y or R, $B_3$ is N, D or S, $B_4$ is S, N or G, $B_5$ is Y, L or W, $B_6$ is P, $B_7$ is V, L, S or P, $B_8$ is I or absent, $B_9$ is F or absent, $B_{10}$ is T, $B_{11}$ is F, $B_{12}$ is G, $B_{13}$ is Q, G or P, $B_{14}$ is G, $B_{15}$ is T, $B_{16}$ is K, $B_{17}$ is V, or the sequence $B_1$-$B_{17}$ comprising no more than 6 conservative substitutions therefrom.

In one embodiment the antibody has the sequence $A_1$-$A_{18}$ to comprises no more than 3 conservative substitutions, such as no more than 1 conservative substitution. In a second embodiment the antibody has the sequence $B_1$-$B_{18}$ comprises no more than 3 conservative substitutions, such as no more than 1 conservative substitution.

Conservative substitutions as used herein is defined as substitution within the classes of amino acids reflected in one or more of the groups in one or more of the Tables 1-3.

TABLE 1

| Amino acid residue classes for conservative substitutions. | |
|---|---|
| Acidic residues | Asp (D) and Glu (E) |
| Basic residues | Lys (K), Arg (R) and His (H) |
| Hydrophilic uncharged residues | Ser (S), Thr (T), Asn (N) and Gln (Q) |
| Aliphatic uncharged residues | Gly (G), Ala (A), Val (V), Leu (L) and Ile (I) |
| Non-polar uncharged residues | Cys (C), Met (M) and Pro (P) |
| Aromatic residues | Phe (F), Tyr (Y) and Trp (W) |

TABLE 2

Alternative conservative amino acid residue substitution classes.

| | | | |
|---|---|---|---|
| 1 | A | S | T |
| 2 | D | E | |
| 3 | N | Q | |
| 4 | R | K | |
| 5 | I | L | M |
| 6 | F | Y | W |

TABLE 3

| Alternative physical and functional conservative amino acid residue substitution classes. | |
|---|---|
| Alcoholic group-containing residues | S and T |
| Aliphatic residues | I, L, V and M |
| Cycloalkyl-associated residues | F, H, W and Y |
| Hydrophobic residues | A, C, F, G, H, I, L, M, R, T, V, W and Y |
| Negatively charged residues | D and E |
| Polar residues | C, D, E, H, K, N, Q, R, S and T |
| Positively charged residues | H, K and R |
| Small residues | A, C, D, G, N, P, S, T and V |
| Very small residues | A, G and S |
| Residues involved in turn formation | A, C, D, E, G, H, K, N, Q, R, S, P and T |
| Flexible residues | Q, T, K, S, G, P, D, E and R |

In one embodiment the antibody comprises:

A Complementarity Determining Region (CDR) H3 loop comprising the sequence $A_1$-$A_{18}$, (SEQ ID NO:28) wherein $A_1$ is C, $A_2$ is A or V, $A_3$ is R or K, $A_4$ is S, N, Q or D, $A_5$ is Y, S G or absent, $A_6$ is P, F or absent, $A_7$ is H, R, D or absent, $A_8$ is K, S or T, $A_9$ is R or G, $A_{10}$ is W, G or F, $A_{11}$ is L, Y, E or W, $A_{12}$ is R or absent, $A_{13}$ is P, F, D or G, $A_{14}$ is P, F, A or I, $A_{15}$ is F, $A_{16}$ is D or E, $A_{17}$ is Y or I, and A18 is W; and A CDR L3 loop comprising the sequence $B_1$-$B_{17}$, (SEQ ID NO:29) wherein $B_1$ is Q, $B_2$ is Y or R, $B_3$ is N, D or S, $B_4$ is S, N or G, $B_5$ is Y, L or W, $B_6$ is P, $B_7$ is V, L, S or P, $B_8$ is I or absent, $B_9$ is F or absent, $B_{10}$ is T, $B_{11}$ is F, $B_{12}$ is G, $B_{13}$ is Q, G or P, $B_{14}$ is G, $B_{15}$ is T, $B_{16}$ is K, and $B_{17}$ is V.

The antibody according to any the present invention preferably binds to streptococcal M protein with a $K_D$ of less than $50\times10^{-9}$ $M^{-1}$, as determined by binding to *Streptococcus pyogenes* SF370. In one embodiment the antibody binds to streptococcal M protein with a $K_D$ less than $15\times10^{-9}$ $M^{-1}$, less than $5\times10^{-9}$ $M^{-1}$ or less than $1\times10^{-9}$ $M^{-1}$.

In a further embodiment the antibody of the invention has said CDR H3 loop selected from SEQ ID NO:1, SEQ ID NO:2, SEQ ID NO:3, SEQ ID NO:4.

```
SEQ ID NO: 1 is CARSYPHKRWLRPPFDYW.

SEQ ID NO: 2 is CAKNSRSGWYFFFDYWGQ.

SEQ ID NO: 3 is CARQGFDTRGEDAFEIWG.

SEQ ID NO: 4 is CVRDSRFWGIFDYWGQGT.
```

In a further embodiment, the antibody according to the invention has a H3 chain selected from SEQ ID NO:9, SEQ ID NO:10, SEQ ID NO:11, SEQ ID NO:12 and any variant sequence having less than 20 conservative amino acid substitutions relative to SEQ ID NO:9, SEQ ID NO:10, SEQ ID NO:11 or SEQ ID NO:12.

```
The H3 chain of Ab25 is SEQ ID NO: 9
having the sequence:
VQLVESGGGVVQPGRSLRLSCAASGFTFSSYAMHWVRQAPGKG

LEWVALISYD-GRNKY-YADSVKGRFTISRDNSKNTLYLQMNS

LRAEDTAVYYCARSYPHKRWLRPPFDYWGQGTLVTVSS

The H3 chain of Ab26 is SEQ ID NO: 10
having the sequence:
VQLVESGGGVVQPGRSLRLSCAASGFTFSSYGMHWVRQAPGKG

LEWVAVISYD-GNNKY-YADSVKGRFTISRDNSKNTLYLQVNS

LRAEDTAVYYCAKNSRSGWYFFFDYWGQ

The H3 chain of Ab32 is SEQ ID NO: 11
having the sequence:
VQLVESGGGLVRPGGSLRLSCVASGFMFNEYYMSWIRQAPGKG

LEWISFISNAGTY-TNYAESVKGRFTISRDNAKDSLYLEMNSL

RGEDTAVYYCARQGFDTRGEDAFEIWGQGTMVTVSS

The H3 chain of Ab49 is SEQ ID NO: 12
having the sequence:
EVQLVESGGGLVQPGGSLRLSCAASGFTVSINYMSWVR-QAPG

KGLQWVSVIYSGGSTY-YADSVKGRFTISRDNSKNTLYLQMNS

LRAEDTAMYYCVRDSRFWGIFDYWGQGTLVTVSS
```

In some embodiments, the antibody comprises said variant sequence of H3 chain having less than 10 conservative amino acid substitutions, less than 5 conservative amino acid substitutions, or less than 2 conservative amino acid substitutions.

In another embodiment the antibody comprises said CDR L3 loop being selected from SEQ ID NO:5, SEQ ID NO:6, SEQ ID NO:7 and SEQ ID NO:8.

```
SEQ ID NO: 5 is QYNSYPVTFGQGTKV

SEQ ID NO: 6 is QYDNLPLTFGGGTKV

SEQ ID NO: 7 is QRSGWPSIFTFGPGTKV

SEQ ID NO: 8 is QRSNWPPTFGQGTKV
```

In a further embodiment, the antibody according to the invention has a L3 chain selected from SEQ ID NO:13, SEQ ID NO:14, SEQ ID NO:15, SEQ ID NO:16 and any variant sequence having less than 20 conservative amino acid substitutions relative to SEQ ID NO:13, SEQ ID NO:14, SEQ ID NO:15 or SEQ ID NO:16.

```
The L3 chain of Ab25 is SEQ ID NO: 13
having the sequence:
DIQMTQSPSTLSASVGDRVTITCRASQSISSWLAWYQQKP

GKAPKLLIYDAS-SLESGVPSRFSGSGSGTEFTLTISSLQ

PDDFASYCCQQYNSYPVTFGQGTKVDIK

The L3 chain of Ab26 is SEQ ID NO: 14
having the sequence:
DIQMTQSPSSLSASVGDRVTITCQASQDISNYLNWYQQKP

GKAPKLLIYDASN-LETGVPSRFSGSGSGTDFTFTISSLQ

PEDIATYYCQQYDNLPLTFGGGTKVEIK

The L3 chain of Ab32 is SEQ ID NO: 15
having the sequence:
EIVLTQSPATLSLSPGERATLSCRASQPLSGYLAWYQQKP

GQAPRLLIYNASKRAT-GIPARFTGSGSGTDFTLTISSLE

SEDFAVYYCQQRSGWPSIFTFGPGTKVDIK

The L3 chain of Ab49 is SEQ ID NO: 16
having the sequence:
EIVLTQSPATLSLSPGERATLSCRASQSVSSYLAWYQRKP

GQAPRLLIYDASNRAT-GIPARFSGSGSGTDFTLTISSLE

PEDFAVYYCQQRSNWPPTFGQGTKVEIK
```

In some embodiments, the antibody comprises said variant sequence of L3 chain having less than 10 conservative amino acid substitutions, less than 5 conservative amino acid substitutions, or less than 2 conservative amino acid substitutions.

In a further embodiment the antibody of the invention is selected from the group consisting of an antibody comprising SEQ ID NO: 17 as the heavy chain and SEQ ID NO: 21 as the light chain, an antibody comprising SEQ ID NO: 18 as the heavy chain and SEQ ID NO: 22 as the light chain, an antibody comprising SEQ ID NO: 19 as the heavy chain and SEQ ID NO: 23 as the light chain, an antibody comprising SEQ ID NO: 20 as the heavy chain and SEQ ID NO: 24 as the light chain, and an antibody which is a variant of any of said antibodies, which variant preferably has at most one, two, five or ten amino acid modifications in each of the heavy and/or light chains, more preferably amino acid substitutions, such as conservative amino acid substitutions in said sequences.

The heavy chain of Ab25 is SEQ ID NO: 17 having the sequence:
MGWSCIILFLVATATGVHSEVQLVESGGGVVQPGRSLRLS

CAASGFTFSSYAM-HWVRQAP-GKGLEWVALISYDGRNKY

YADSVKGRFTISRDNSKNTLYLQMNSLRAEDTAVYYCARS

YPHKRWLRPPFDYWGQGTLVTVSSASTKGPSVFPLAPSSK

STSGGTAALGCLV-KDYFPEP-VTVSWNSGALTSGVHTFP

AVLQSSGLYSLSSVVTVPSSSLGTQTYICNVNHKPSNTKV

DKRVEPKSCDKTHTCPPCPAPELLGGPSVFLFPPKPKDTL

MISRTPEVTCVVVDVS-HEDPEV-KFNWYVDGVEVHNAKT

KPREEQYNSTYRVVSVLTVLHQDWLNGKEYKCKVSNKALP

APIEKTISKAKGQPREPQVYTLPPSREEMTKNQVSLTCLV

KGFYPSDIAVEWESNG-QPEN-NYKTTPPVLDSDGSFFLY

SKLTVDKSRWQQGNVFSCSVMHEALHNHYTQKSLSLSPGK

The heavy chain of Ab26 is SEQ ID NO: 18 having the sequence:
MGWSCIILFLVATATGVHSEVQLVESGGGVVQP-GRSLRL

SCAASGFTFSSYGMHWVRQAP-GKGLEWVAVISYDGNNKY

YADSVKGRFTISRDNSKNTLYLQVNSLRAEDTAVYYCAKN

SRSGWYFFFDYWGQGTLVTVSSASTKGPSVFPLAPSSKST

SGGTAALGCLV-KDYFPEP-VTVSWNSGALTSGVHTFPAV

LQSSGLYSLSSVVTVPSSSLGTQTYICNVNHKPSNTKVDK

RVEPKSCDKTHTCPPCPAPELLGGPSVFLFPPKPKDTLMI

SRTPEVTCVVVDVS-HEDPEV-KFNWYVDGVEVHNAKTKP

REEQYNSTYRVVSVLTVLHQDWLNGKEYKCKVSNKALPAP

IEKTISKAKGQPREPQVYTLPPSREEMTKNQVSLTCLVKG

FYPSDIAVEWESNG-QPEN-NYKTTPPVLDSDGSFFLYSK

LTVDKSRWQQGNVFSCSVMHEALHNHYTQKSLSLSPGK

The heavy chain of Ab32 is SEQ ID NO: 19 having the sequence:
MGWSCIILFLVATATGVHSEVQLVESGGGLVRPGGSLRLS

CVASGFMF-NEYYMSWIRQAP-GKGLEWISFISNAGTYTN

YAESVKGRFTISRDNAKDSLYLEMNSLRGEDTAVYYCARQ

GFDTRGEDAFEIWGQGTMVTVSSASTKGPSVFPLAPSSKS

TSGGTAALGCLV-KDYFPEP-VTVSWNSGALTSGVHTFPA

VLQSSGLYSLSSVVTVPSSSLGTQTYICNVNHKPSNTKVD

KRVEPKSCDKTHTCPPCPAPELLGGPSVFLFPPKPKDTLM

ISRTPEVTCVVVDVS-HEDPEV-KFNWYVDGVEVHNAKTK

PREEQYNSTYRVVSVLTVLHQDWLNGKEYKCKVSNKALPA

PIEKTISKAKGQPREPQVYTLPPSREEMTKNQVSLTCLVK

-continued

GFYPSDIAVEWESNG-QPEN-NYKTTPPVLDSDGSFFLYS

KLTVDKSRWQQGNVFSCSVMHEALHNHYTQKSLSLSPGK

The heavy chain of Ab49 is SEQ ID NO: 20 having the sequence:
MGWSCIILFLVATATGVHSEVQLVESGGGLVQPGGSLRLS

CAASGFTVSINYMS-WVRQAP-GKGLQWVSVIYSGGSTYY

ADSVKGRFTISRDNSKNTLYLQMNSLRAEDTAMYYCVRDS

RFWGIFDYWGQGTLVTVSSASTKGPSVFPLAPSSKSTSGG

TAALGCLVKDYFPEP-VTVSWNSGALTSGVHTFPAVLQSS

GLYSLSSVVTVPSSSLGTQTYICNVNHKPSNTKVDKRVEP

KSCDKTHTCPPCPAPELLGGPSVFLFPPKPKDTLMISRTP

EVTCVVVDVS-HEDPEV-KFNWYVDGVEVHNAKTKPREEQ

YNSTYRVVSVLTVLHQDWLNGKEYKCKVSNKALPAPIEKT

ISKAKGQPREPQVYTLPPSREEMTKNQVSLTCLVKGFYPS

DIAVEWESNG-QPEN-NYKTTPPVLDSDGSFFLYSKLTVD

KSRWQQGNVFSCSVMHEALHNHYTQKSLSLSPGK

The light chain of Ab25 is SEQ ID NO: 21 having the sequence:
MGWSCIILFLVATATGVHSDIQMTQSPSTLSASVG-DRVT

ITCRASQSISSWLAWYQQKPGKAPKLLIYDASSLESGVPS

RFSGSGSGTEFTLTISSLQPDDFASYCCQQYNSYPVTFGQ

GTKVDIKRTVAAPSVFIFPPSDEQLKSG-TASVVCLLNNF

YPREAKVQWKVDNALQSGNSQESVTEQDSKDSTYSLSSTL

TLSKADYEKHKVYACEVTHQGLSSPVTKSFNRGEC

The light chain of Ab26 is SEQ ID NO: 22 having the sequence:
MGWSCIILFLVATATGVHSDIQMTQSPSSLSASVG-DRVT

ITCQASQDISNYLNWYQQKPGKAPKLLIYDASNLETGVPS

RFSGSGSGTDFTFTISSLQPEDIATYYCQQYDNLPLTFGG

GTKVEIKRTVAAPSVFIFPPSDEQLKSG-TASVVCLLNNF

YPREAKVQWKVDNALQSGNSQESVTEQDSKDSTYSLSSTL

TLSKADYEKHKVYACEVTHQGLSSPVTKSFNRGEC

The light chain of Ab32 is SEQ ID NO: 23 having the sequence:
MGWSCIILFLVATATGVHSEIVLTQSPATLSLSPGER-AT

LSCRASQPLSGYLAWYQQKPGQAPRLLIYNASKRATGI

PARFTGSGSGTDFTLTISSLESEDFAVYYCQQRSGWPSIF

TFGPGTKVDIKRTVAAPSVFIFPPSDEQLKSG-TASVVCL

LNNFYPREAKVQWKVDNALQSGNSQESVTEQDSKDSTYSL

SSTLTLSKADYEKHKVYACEVTHQGLSSPVTKSFNRGEC

The light chain of Ab49 is SEQ ID NO: 24 havingthesequence:MGWSCIILFLVATATGVHSEIV

LTQSPATLSLSPGERATLSCRASQSVSSYLAWYQRK-PGQ

APRLLIYDASNRATGIPARFSGSGSGTDFTLTISSLEPED

FAVYYCQQRSNWPPTFGQGTKVEIKRTVAAPSVFIFPPSD

-continued

```
EQLKSGTASVVCLLNNFYPREAK-VQWKVDNALQSGNSQE

SVTEQDSKDSTYSLSSTLTLSKADYEKHKVYACEVTHQGL

SSPVTKSFNRGEC
```

In another embodiment the antibody of the invention is selected from the group consisting of

- an antibody comprising SEQ ID NO: 17 as the heavy chain and SEQ ID NO: 21 as the light chain,
- an antibody comprising SEQ ID NO: 18 as the heavy chain and SEQ ID NO: 22 as the light chain,
- an antibody comprising SEQ ID NO: 19 as the heavy chain and SEQ ID NO: 23 as the light chain, and
- an antibody comprising SEQ ID NO: 20 as the heavy chain and SEQ ID NO: 24 as the light chain.

In another embodiment the antibody of the invention is selected from the group consisting of

- an antibody comprising all of the six CDRs from SEQ ID NO: 17 and SEQ ID NO: 21,
- an antibody comprising all of the six CDRs from SEQ ID NO: 18 and SEQ ID NO: 22,
- an antibody comprising all of the six CDRs from SEQ ID NO: 19 and SEQ ID NO: 23, and
- an antibody comprising all of the six CDRs from SEQ ID NO: 20 and SEQ ID NO: 24.

In an embodiment, the antibody according to the invention has the ability to mediate bacterial agglutination.

In another embodiment, the antibody according to the invention has the ability to mediate NFkB-activation.

In yet another embodiment the antibody according to the invention has the ability to induce phagocytosis.

In yet another embodiment the antibody has the ability to exhibit simultaneous binding to two different epitopes of the streptococcal M protein by way of dual-Fab cis antibody binding. In an embodiment the antibody has said two different epitopes of the streptococcal M protein being a) in the B repeats and C repeats, b) in the linear sequence, or c) in the 3-dimensional structure.

The term "dual-Fab cis antibody binding" as used herein is intended to mean binding by an antibody where only one binding site binds to two distinct binding sites on the target molecule. Hence, dual-Fab cis antibody binding is different from the binding by known bi-specific antibodies which contain two independent variable sites each binding to one of two sites on the target molecule. Ab25 is capable of dual-Fab cis binding in an intramolecular cis-binding fashion to two distinct, non-identical epitopes.

The requirement of dual-Fab cis binding to separate epitopes that Ab25 exhibits, is an unexpected mode of functional antibody interaction, adding to the already astounding diversity found in antibodies (Kanyavuz et al., 2019). A related phenomenon to the dual-Fab cis binding is the case of the anti-HIV 2G12 antibody (Trkola et al., 1996) which has a mutation in its hinge region leading to Fab dimerization (Gach et al., 2010). The two Fabs of 2G12 bind to high-mannose sugars but due to the fact of their unorthodox dimerization, essentially behave as one large Fab (Calarese et al., 2005). In fact, normal single Fab-based interactions between multiple anti-HIV glycan antibodies gave similar biological outcomes as 2G12 (for a review see Kong et al., 2014). This indicates that while 2G12 has an unorthodox structure, its function is correlated to the specific epitope and not due to a distinct mode of interaction. In the context of unorthodox antibodies, bispecific antibodies (Kontermann and Brinkmann, 2015) or antigen clasping antibodies (Hattori et al., 2016) have been engineered for improved functionality, and the present invention shows that evolution has resulted in similar outcomes. The present invention reveal an, up till now, unknown added value of using F(ab')2 fragments rather than Fabs when screening for functional antibodies.

In a further aspect the invention provides a pharmaceutical composition comprising the antibody of the invention and at least one pharmaceutically acceptable excipient.

In one embodiment the pharmaceutical composition comprises two or more different antibodies as defined by the invention.

The antibodies and antibody compositions of the invention disclosed herein may be used to combat bacterial or viral infections in individuals. In particular the antibodies may be used to treat infections with Group A *Streptococcus.*

Pharmaceutical compositions for parenteral administration such as intravenous or subcutaneous administration may be liquid or solid formulations for administration. Solid formulations for reconstitution may be delivered by injection or infusion. Such formulations are typically sterile products.

The treatment method may consist of a single administration or a plurality of administrations over a period of time.

Depending upon the particular treatment and the individual to be treated, as well as the route of administration, the compositions may be administered at varying doses and/or frequencies.

The pharmaceutical compositions must be stable under the conditions of manufacture and storage; thus, if necessary they should be preserved against the contaminating action of microorganisms such as bacteria and fungi. In case of liquid formulations such as solutions, the carrier can be a solvent containing, for example, water, ethanol, polyol (e.g. glycerol, propylene glycol and liquid polyethylene glycol), buffer, isotonicity agent and suitable mixtures thereof.

The compositions for use in the treatment methods of the invention comprises at least one pharmaceutically acceptable excipient, such as carriers, solvents, pH-adjusting agents, buffers, stabilizing agents, surfactants, solubilizers, preservatives etc.

It should be understood that in addition to the ingredients particularly mentioned above the formulations of this invention may include other agents conventional in the art having regard to the type of formulation in question. A person skilled in the art will know how to choose a suitable formulation and how to prepare it (see eg Remington's Pharmaceutical Sciences 18 Ed. or later). A person skilled in the art will also know how to choose a suitable administration route and dosage.

In a further aspect the invention provides the use of the antibody of the invention for the treatment of a streptococcal infection, such as Group A *Streptococcus.*

In one embodiment the use of the antibody according to the invention is for the treatment of sepsis.

In a further embodiment the use of said antibody comprises the parenteral administration, such as intravenously, subcutaneously or intramuscularly.

In an embodiment this use is in combination with intravenous immunoglobulin (IVIG). In another embodiment the use of the pharmaceutical composition of the invention is for the treatment of sepsis. In a further embodiment this use of said antibody comprises administration intravenously, subcutaneously or intramuscularly.

In a further aspect the present invention provides the use of an antibody of the invention in an application selected from Western blot, Flow Cytometry, ELISA and Immunoflourescence.

In a further aspect the present invention provides an antibody exhibiting binding to two different epitopes of a molecule by way of dual-Fab cis antibody binding. In an embodiment said two different epitopes of a molecule is two different epitopes of a protein or a carbohydrate. In one embodiment said molecule is a protein. In another embodiment said two different epitopes of a protein is two different epitopes of streptococcal M protein.

In a further aspect the present invention provides a method for obtaining an antibody exhibiting simultaneous binding to two different epitopes of a molecule by way of Dual-Fab cis antibody binding, comprising the steps:

obtaining an antibody from a donor which has been exposed to said molecule such as to raise an immune response, cleaving the antibody in single Fab fragments from said antibody by enzymatic reaction, cleaving the antibody F(ab')2-fragments from said antibody by enzymatic reaction, measuring and comparing binding of the intact antibody versus F(ab')2-fragments and single Fab fragments, confirming a significant reduction in single Fab binding as compared to antibody binding, thereby identifying and providing said antibody.

In one embodiment of this method said two different epitopes of a molecule is two different epitopes of streptococcal M protein.

In a further aspect the present invention provides a method for crosslinking antibody F(ab')2-fragments bound to a molecule, comprising the steps:

cleaving the antibody F(ab')2-fragments from the antibody by enzymatic reaction, isolating the antibody F(ab')2-fragments, contacting said antibody F(ab')2-fragments and said molecule in a solution, adding disuccinimidylsuberate to said solution and allowing the reaction to proceed, quenching the crosslinking reaction, thereby obtaining the crosslinked antibody F(ab')2-fragments.

In an embodiment of this method said molecule is a protein, such as streptococcal M protein.

The following list of non-limiting embodiments further illustrate the invention:

1. An antibody binding to streptococcal M protein, wherein said antibody comprises:
   A Complementarity Determining Region (CDR) H3 loop comprising the sequence $A_1$-$A_{18}$, (SEQ ID NO:28) wherein
   $A_1$ is C, $A_2$ is A or V, $A_3$ is R or K, $A_4$ is S, N, Q or D, $A_5$ is Y, S G or absent, $A_6$ is P, F or absent, $A_7$ is H, R, D or absent, $A_8$ is K, S or T, $A_9$ is R or G, $A_{10}$ is W, G or F, $A_{11}$ is L, Y, E or W, $A_{12}$ is R or absent, $A_{13}$ is P, F, D or G, $A_{14}$ is P, F, A or I, $A_{15}$ is F, $A_{16}$ is D or E, $A_{17}$ is Y or I, A18 is W, or the sequence $A_1$-$A_{18}$ comprising no more than 6 conservative substitutions therefrom; and
   A CDR L3 loop comprising the sequence $B_1$-$B_{17}$, (SEQ ID NO:29) wherein
   $B_1$ is Q, $B_2$ is Y or R, $B_3$ is N, D or S, $B_4$ is S, N or G, $B_5$ is Y, L or W, $B_6$ is P, $B_7$ is V, L, S or P, $B_8$ is I or absent, $B_9$ is F or absent, $B_{10}$ is T, $B_{11}$ is F, $B_{12}$ is G, $B_{13}$ is Q, G or P, $B_{14}$ is G, $B_{15}$ is T, $B_{16}$ is K, $B_{17}$ is V, or the sequence $B_1$-$B_{17}$ comprising no more than 6 conservative substitutions therefrom.
2. The antibody according to embodiment 1, wherein said sequence $A_1$-$A_{18}$ comprises no more than 3 conservative substitutions.
3. The antibody according to embodiment 1, wherein said sequence $B_1$-$B_{18}$ comprises no more than 3 conservative substitutions.
4. The antibody according to embodiment 1, wherein said sequence $A_1$-$A_{18}$ comprises no more than 1 conservative substitution.
5. The antibody according to embodiment 1, wherein said sequence $B_1$-$B_{18}$ comprises no more than 1 conservative substitution.
6. The antibody according to any of the preceding embodiments, wherein said antibody comprises:
   A Complementarity Determining Region (CDR) H3 loop comprising the sequence $A_1$-$A_{18}$, (SEQ ID NO:28) wherein
   $A_1$ is C, $A_2$ is A or V, $A_3$ is R or K, $A_4$ is S, N, Q or D, $A_5$ is Y, S G or absent, $A_6$ is P, F or absent, $A_7$ is H, R, D or absent, $A_8$ is K, S or T, $A_9$ is R or G, $A_{10}$ is W, G or F, $A_{11}$ is L, Y, E or W, $A_{12}$ is R or absent, $A_{13}$ is P, F, D or G, $A_{14}$ is P, F, A or I, $A_{15}$ is F, $A_{16}$ is D or E, $A_{17}$ is Y or I, and A18 is W; and
   A CDR L3 loop comprising the sequence $B_1$-$B_{17}$, (SEQ ID NO:29) wherein
   $B_1$ is Q, $B_2$ is Y or R, $B_3$ is N, D or S, $B_4$ is S, N or G, $B_5$ is Y, L or W, $B_6$ is P, $B_7$ is V, L, S or P, $B_8$ is I or absent, $B_9$ is F or absent, $B_{10}$ is T, $B_{11}$ is F, $B_{12}$ is G, $B_{13}$ is Q, G or P, $B_{14}$ is G, $B_{15}$ is T, $B_{16}$ is K, and $B_{17}$ is V.
7. The antibody according to any of the preceding embodiments, which binds to streptococcal M protein with a $K_D$ of less than $50\times10^{-9}$ $M^{-1}$, as determined by binding to *Streptococcus pyogenes* SF370.
8. The antibody according to embodiment 7, wherein said $K_D$ is less than $15\times10^{-9}$ $M^{-1}$.
9. The antibody according to embodiment 7, wherein said $K_D$ is less than $5\times10^{-9}$ $M^{-1}$.
10. The antibody according to embodiment 7, wherein said $K_D$ is less than $1\times10^{-9}$ $M^{-1}$.
11. The antibody according to any of the preceding embodiments, wherein said CDR H3 loop is selected from SEQ ID NO:1, SEQ ID NO:2, SEQ ID NO:3 and SEQ ID NO:4.
12. The antibody according to any of the preceding embodiments, wherein said CDR L3 loop is selected from SEQ ID NO:5, SEQ ID NO:6, SEQ ID NO:7 and SEQ ID NO:8.
13. The antibody according to any of the preceding embodiments wherein the H3 chain is selected from SEQ ID NO:9, SEQ ID NO:10, SEQ ID NO:11, SEQ ID NO:12 and any variant sequence having less than 20 conservative amino acid substitutions relative to SEQ ID NO:9, SEQ ID NO:10, SEQ ID NO:11 or SEQ ID NO:12.
14. The antibody according to any of the preceding embodiments, wherein said L3 chain is selected from SEQ ID NO:13, SEQ ID NO:14, SEQ ID NO:15, SEQ ID NO:16 and any variant sequence having less than 20 conservative amino acid substitutions relative to SEQ ID NO:13, SEQ ID NO:14, SEQ ID NO:15 or SEQ ID NO:16.
15. The antibody according to any of embodiments 13-14, wherein said variant sequence has less than 10 conservative amino acid substitutions.

16. The antibody according to any of embodiments 13-14, wherein said variant sequence has less than 5 conservative amino acid substitutions.
17. The antibody according to any of embodiments 13-14, wherein said variant sequence has less than 2 conservative amino acid substitutions.
18. The antibody according to any of the preceding embodiments, wherein said H3 chain is selected from SEQ ID NO:9, SEQ ID NO:10, SEQ ID NO:11 and SEQ ID NO:12.
19. The antibody according to any of the preceding embodiments, wherein said L3 chain is selected from SEQ ID NO:13, SEQ ID NO:14, SEQ ID NO:15 and SEQ ID NO:16.
20. The antibody according to any of the preceding embodiments, which is selected from the group consisting of
    an antibody comprising SEQ ID NO: 17 as the heavy chain and SEQ ID NO: 21 as the light chain,
    an antibody comprising SEQ ID NO: 18 as the heavy chain and SEQ ID NO: 22 as the light chain,
    an antibody comprising SEQ ID NO: 19 as the heavy chain and SEQ ID NO: 23 as the light chain,
    an antibody comprising SEQ ID NO: 20 as the heavy chain and SEQ ID NO: 24 as the light chain, and
    an antibody which is a variant of any of said antibodies, which variant preferably has at most one, two, five or ten amino acid modifications in each of the heavy and/or light chains, more preferably amino acid substitutions, such as conservative amino acid substitutions in said sequences.
21. The antibody according to embodiment 20, which is selected from the group consisting of
    an antibody comprising SEQ ID NO: 17 as the heavy chain and SEQ ID NO: 21 as the light chain,
    an antibody comprising SEQ ID NO: 18 as the heavy chain and SEQ ID NO: 22 as the light chain,
    an antibody comprising SEQ ID NO: 19 as the heavy chain and SEQ ID NO: 23 as the light chain, and
    an antibody comprising SEQ ID NO: 20 as the heavy chain and SEQ ID NO: 24 as the light chain.
22. The antibody according to any of the preceding embodiments, which is selected from the group consisting of
    an antibody comprising all of the six CDRs from SEQ ID NO: 17 and SEQ ID NO: 21,
    an antibody comprising all of the six CDRs from SEQ ID NO: 18 and SEQ ID NO: 22,
    an antibody comprising all of the six CDRs from SEQ ID NO: 19 and SEQ ID NO: 23, and
    an antibody comprising all of the six CDRs from SEQ ID NO: 20 and SEQ ID NO: 24.
23. The antibody according to any of the preceding embodiments, which has the ability to mediate bacterial agglutination.
24. The antibody according to any of the preceding embodiments, which has the ability to mediate NFkB-activation.
25. The antibody according to any of the preceding embodiments, which has the ability to induce phagocytosis.
26. The antibody according to any of the preceding embodiments, which has the ability to exhibit simultaneous binding to two different epitopes of the streptococcal M protein by way of dual-Fab cis antibody binding.
27. The antibody according to embodiment 26, wherein said two different epitopes of the streptococcal M protein are a) in the B repeats and C repeats, b) in the linear sequence, or c) in the 3-dimensional structure.
28. A pharmaceutical composition comprising the antibody as defined in any of embodiments 1-27 and at least one pharmaceutically acceptable excipient.
29. The pharmaceutical composition according to embodiment 28, which comprises two or more different antibodies as defined in any of embodiments 1-26.
30. The use of the antibody according to any of embodiments 1-27 for the treatment of a streptococcal infection, such as Group A *Streptococcus.*
31. The use of the antibody according to any of embodiments 1-27 for the treatment of sepsis.
32. The use according to any of embodiments 30-31, wherein said antibody is administered parenterally, such as intravenously, subcutaneously or intramuscularly.
33. The use according to any of embodiments 30-32 which is in combination with intravenous immunoglobulin (IVIG).
34. The use of the pharmaceutical composition as defined in any of embodiments 28-29 for the treatment of sepsis.
35. The use according to any of embodiments 30-34, wherein said antibody is administered parenterally, such as intravenously, subcutaneously or intramuscularly.
36. Use of an antibody as defined in any of embodiments 1-27 in an application selected from Western blot, Flow Cytometry, ELISA and Immunoflourescence.
37. An antibody exhibiting binding to two different epitopes of a molecule by way of dual-Fab cis antibody binding.
38. The antibody according to embodiment 37, wherein said two different epitopes of a molecule is two different epitopes of a protein, such as streptococcal M protein.
39. Method for obtaining an antibody exhibiting simultaneous binding to two different epitopes of a molecule by way of Dual-Fab cis antibody binding, comprising the steps:
    obtaining an antibody from a donor which has been exposed to said molecule such as to raise an immune response,
    cleaving the antibody in single Fab fragments from said antibody by enzymatic reaction,
    cleaving the antibody F(ab')2-fragments from said antibody by enzymatic reaction,
    measuring and comparing binding of the intact antibody versus F(ab')2-fragments and single Fab fragments,
    confirming a significant reduction in single Fab binding as compared to antibody binding,
    thereby identifying and providing said antibody.
40. The method according to embodiment 39, wherein said two different epitopes of a molecule is two different epitopes of a protein, such as streptococcal M protein.
41. Method for crosslinking antibody F(ab')2-fragments bound to a molecule, comprising the steps:
    cleaving the antibody F(ab')2-fragments from the antibody by enzymatic reaction,
    isolating the antibody F(ab')2-fragments,
    contacting said antibody F(ab')2-fragments and said molecule in a solution, adding disuccinimidylsuberate to said solution and allowing the reaction to proceed, quenching the crosslinking reaction, thereby obtaining the crosslinked antibody F(ab')2-fragments.

42. The method according to embodiment 41, wherein said molecule is a protein such as streptococcal M protein.

REFERENCES

Åkesson, P., Cooney, J., Kishimoto, F. and Björck, L. 1990. Protein H—a novel IgG binding bacterial protein. *Molecular Immunology* 27(6), pp. 523-531.

Åkesson, P., Schmidt, K. H., Cooney, J. and Björck, L. 1994. M1 protein and protein H: IgGFc- and albumin-binding streptococcal surface proteins encoded by adjacent genes. *The Biochemical Journal* 300 (Pt 3), pp. 877-886.

Azuar, A., Jin, W., Mukaida, S., Hussein, W. M., Toth, I. and Skwarczynski, M. 2019.

Recent advances in the development of peptide vaccines and their delivery systems against group A *Streptococcus*. *Vaccines* 7(3).

Bakalar, M. H., Joffe, A. M., Schmid, E. M., Son, S., Podolski, M. and Fletcher, D. A. 2018. Size-Dependent Segregation Controls Macrophage Phagocytosis of Antibody-Opsonized Targets. *Cell* 174(1), p. 131-142.e13.

Bournazos, S., Wang, T. T., Dahan, R., Maamary, J. and Ravetch, J. V. 2017. Signaling by antibodies: recent progress. *Annual Review of Immunology* 35, pp. 285-311.

Calarese, D. A., Lee, H.-K., Huang, C.-Y., Best, M. D., Astronomo, R. D., Stanfield, R. L., Katinger, H., Burton, D. R., Wong, C.-H., and Wilson, I. A. (2005). Dissection of the carbohydrate specificity of the broadly neutralizing anti-HIV-1 antibody 2G12. Proc. Natl. Acad. Sci. USA 102, 13372-13377.

Carapetis, J. R., Steer, A. C., Mulholland, E. K. and Weber, M. 2005. The global burden of group A streptococcal diseases. *The Lancet Infectious Diseases* 5(11), pp. 685-694.

Carlsson, F., Berggärd, K., Stälhammar-Carlemalm, M. and Lindahl, G. 2003. Evasion of phagocytosis through cooperation between two ligand-binding regions in *Streptococcus pyogenes* M protein. *The Journal of Experimental Medicine* 198(7), pp. 1057-1068.

Carlsson, F., Sandin, C. and Lindahl, G. 2005. Human fibrinogen bound to *Streptococcus pyogenes* M protein inhibits complement deposition via the classical pathway. *Molecular Microbiology* 56(1), pp. 28-39.

Cedervall, T., Akesson, P., Stenberg, L., Herrmann, A. and Åkerström, B. 1995. Allosteric and temperature effects on the plasma protein binding by streptococcal M protein family members. *Scandinavian Journal of Immunology* 42(4), pp. 433-441.

Collin, M. and Olsén, A. 2001. EndoS, a novel secreted protein from *Streptococcus pyogenes* with endoglycosidase activity on human IgG. *The EMBO Journal* 20(12), pp. 3046-3055.

Collin, M. and Olsén, A. 2000. Generation of a mature streptococcal cysteine proteinase is dependent on cell wall-anchored M1 protein. *Molecular Microbiology* 36(6), pp. 1306-1318.

Dale, J. B. and Walker, M. J. 2020. Update on group A streptococcal vaccine development. *Current Opinion in Infectious Diseases.*

Freeman, S. A., Vega, A., Riedl, M., et al. 2018. Transmembrane Pickets Connect Cyto- and Pericellular Skeletons Forming Barriers to Receptor Engagement. *Cell* 172(1-2), p. 305-317.e10.

Frick, I. M., Mörgelin, M. and Björck, L. 2000. Virulent aggregates of *Streptococcus pyogenes* are generated by homophilic protein-protein interactions. *Molecular Microbiology* 37(5), pp. 1232-1247.

Gach, J. S., Furtmüller, P. G., Quendler, H., Messner, P., Wagner, R., Katinger, H., and Kunert, R. (2010). Proline is not uniquely capable of providing the pivot point for domain swapping in 2G12, a broadly neutralizing antibody against HIV-1. J. Biol. Chem. 285, 1122-1127.

Ghosh, P. 2018. Variation, Indispensability, and Masking in the M protein. *Trends in Microbiology* 26(2), pp. 132-144.

Gray, J. J. 2006. High-resolution protein-protein docking. *Current Opinion in Structural Biology* 16(2), pp. 183-193.

Happonen, L., Hauri, S., Svensson Birkedal, G., et al. 2019. A quantitative *Streptococcus pyogenes*-human protein-protein interaction map reveals localization of opsonizing antibodies. *Nature Communications* 10(1), p. 2727.

Hattori, T., Lai, D., Dementieva, I. S., et al. 2016. Antigen clasping by two antigen-binding sites of an exceptionally specific antibody for histone methylation. *Proceedings of the National Academy of Sciences of the United States of America* 113(8), pp. 2092-2097.

Hauri, S., Khakzad, H., Happonen, L., Teleman, J., Malmström, J. and Malmström, L. 2019. Rapid determination of quaternary protein structures in complex biological samples. *Nature Communications* 10(1), p. 192.

Herr, A. B., Ballister, E. R. and Bjorkman, P. J. 2003. Insights into IgA-mediated immune responses from the crystal structures of human FcalphaRI and its complex with IgA1-Fc. *Nature* 423(6940), pp. 614-620.

Herwald, H., Cramer, H., Mörgelin, M., et al. 2004. M protein, a classical bacterial virulence determinant, forms complexes with fibrinogen that induce vascular leakage. *Cell* 116(3), pp. 367-379.

Hollands, A., Gonzalez, D., Leire, E., et al. 2012. A bacterial pathogen co-opts host plasmin to resist killing by cathelicidin antimicrobial peptides. *The Journal of Biological Chemistry* 287(49), pp. 40891-40897.

Johansson, L., Thulin, P., Sendi, P., et al. 2008. Cathelicidin LL-37 in severe *Streptococcus pyogenes* soft tissue infections in humans. *Infection and Immunity* 76(8), pp. 3399-3404.

Kadri, S. S., Swihart, B. J., Bonne, S. L., et al. 2017. Impact of Intravenous Immunoglobulin on Survival in Necrotizing Fasciitis With Vasopressor-Dependent Shock: A Propensity Score-Matched Analysis From 130 US Hospitals. *Clinical Infectious Diseases* 64(7), pp. 877-885.

Kanyavuz, A., Marey-Jarossay, A., Lacroix-Desmazes, S. and Dimitrov, J. D. 2019. Breaking the law: unconventional strategies for antibody diversification. *Nature Reviews. Immunology* 19(6), pp. 355-368.

Karami, Y., Rey, J., Postic, G., Murail, S., Tufféry, P. and de Vries, S. J. 2019. DaReUS-Loop: a web server to model multiple loops in homology models. *Nucleic Acids Research* 47(W1), pp. W423-W428.

Klein, J. S. and Bjorkman, P. J. 2010. Few and far between: how HIV may be evading antibody avidity. *PLoS Pathogens* 6(5), p. e1000908.

Kline, K. A., Fslker, S., Dahlberg, S., Normark, S. and Henriques-Normark, B. 2009. Bacterial adhesins in host-microbe interactions. *Cell Host & Microbe* 5(6), pp. 580-592.

Koehler Leman, J., Weitzner, B. D., Lewis, S. M., Consortium, R. and Bonneau, R. 2019. Macromolecular modeling and design in rosetta: new methods and frameworks.

Kong, L., Stanfield, R. L., and Wilson, I. A. (2014). Molecular recognition of HIV glycans by antibodies. In HIV Glycans in Infection and Immunity, R. Pantophlet, ed. (New York, NY: Springer New York), pp. 117-141.

Kontermann, R. E. and Brinkmann, U. 2015. Bispecific antibodies. *Drug Discovery Today* 20(7), pp. 838-847.

Kurosaki, T., Kometani, K. and Ise, W. 2015. Memory B cells. *Nature Reviews. Immunology* 15(3), pp. 149-159.

Laabei, M. and Ermert, D. 2019. Catch Me if You Can: *Streptococcus pyogenes* Complement Evasion Strategies. *Journal of Innate Immunity* 11(1), pp. 3-12.

Linnér, A., Darenberg, J., Sjölin, J., Henriques-Normark, B. and Norrby-Teglund, A. 2014. Clinical efficacy of polyspecific intravenous immunoglobulin therapy in patients with streptococcal toxic shock syndrome: a comparative observational study. *Clinical Infectious Diseases* 59(6), pp. 851-857.

Lu, L. L., Suscovich, T. J., Fortune, S. M. and Alter, G. 2018. Beyond binding: antibody effector functions in infectious diseases. *Nature Reviews. Immunology* 18(1), pp. 46-61.

Macheboeuf, P., Buffalo, C., Fu, C., et al. 2011. Streptococcal M1 protein constructs a pathological host fibrinogen network. *Nature* 472(7341), pp. 64-68.

Madsen, M. B., Hjortrup, P. B., Hansen, M. B., et al. 2017. Immunoglobulin G for patients with necrotising soft tissue infection (INSTINCT): a randomised, blinded, placebo-controlled trial. *Intensive Care Medicine* 43(11), pp. 1585-1593.

Mitchell, T. J. 2003. The pathogenesis of streptococcal infections: from tooth decay to meningitis. *Nature Reviews. Microbiology* 1(3), pp. 219-230.

Mitsi, E., Roche, A. M., Reiné, J., et al. 2017. Agglutination by anti-capsular polysaccharide antibody is associated with protection against experimental human pneumococcal carriage. *Mucosal Immunology* 10(2), pp. 385-394.

Moor, K., Diard, M., Sellin, M. E., et al. 2017. High-avidity IgA protects the intestine by enchaining growing bacteria. *Nature* 544(7651), pp. 498-502.

Motley, M. P., Banerjee, K. and Fries, B. C. 2019. Monoclonal antibody-based therapies for bacterial infections. *Current Opinion in Infectious Diseases* 32(3), pp. 210-216.

de Neergaard, T., Sundwall, M. and Nordenfelt, P. 2019. High-sensitivity assessment of phagocytosis by persistent association-based normalization. *BioRxiv.*

Nordenfelt, P. and Tapper, H. 2011. Phagosome dynamics during phagocytosis by neutrophils. *Journal of Leukocyte Biology* 90(2), pp. 271-284.

Nordenfelt, P., Waldemarson, S., Linder, A., et al. 2012. Antibody orientation at bacterial surfaces is related to invasive infection. *The Journal of Experimental Medicine* 209(13), pp. 2367-2381.

Okumura, C. Y. M. and Nizet, V. 2014. Subterfuge and sabotage: evasion of host innate defenses by invasive gram-positive bacterial pathogens. *Annual Review of Microbiology* 68, pp. 439-458.

Oliver, J., Malliya Wadu, E., Pierse, N., Moreland, N. J., Williamson, D. A. and Baker, M. G. 2018. Group A *Streptococcus* pharyngitis and pharyngeal carriage: A meta-analysis. *PLoS Neglected Tropical Diseases* 12(3), p. e0006335.

Ozberk, V., Pandey, M. and Good, M. F. 2018. Contribution of cryptic epitopes in designing a group A streptococcal vaccine. *Human vaccines & immunotherapeutics* 14(8), pp. 2034-2052.

Pandey, M., Ozberk, V., Calcutt, A., et al. 2016. Streptococcal immunity is constrained by lack of immunological memory following a single episode of pyoderma. *PLoS Pathogens* 12(12), p. e1006122.

Parks, T., Wilson, C., Curtis, N., Norrby-Teglund, A. and Sriskandan, S. 2018. Polyspecific Intravenous Immunoglobulin in Clindamycin-treated Patients With Streptococcal Toxic Shock Syndrome: A Systematic Review and Meta-analysis. *Clinical Infectious Diseases* 67(9), pp. 1434-1436.

Pascual, V., Liu, Y. J., Magalski, A., de Bouteiller, O., Banchereau, J. and Capra, J. D. 1994. Analysis of somatic mutation in five B cell subsets of human tonsil. *The Journal of Experimental Medicine* 180(1), pp. 329-339.

von Pawel-Rammingen, U., Johansson, B. P. and Björck, L. 2002. IdeS, a novel streptococcal cysteine proteinase with unique specificity for immunoglobulin G. *The EMBO Journal* 21(7), pp. 1607-1615.

Skwarczynski, M. and Toth, I. 2016. Peptide-based synthetic vaccines. *Chemical science* (*Royal Society of Chemistry:* 2010) 7(2), pp. 842-854.

Smith, K., Garman, L., Wrammert, J., et al. 2009. Rapid generation of fully human monoclonal antibodies specific to a vaccinating antigen. *Nature Protocols* 4(3), pp. 372-384.

Sondermann, P., Huber, R., Oosthuizen, V. and Jacob, U. 2000. The 3.2-A crystal structure of the human IgG1 Fc fragment-Fc gammaRIII complex. *Nature* 406(6793), pp. 267-273.

Song, Y., DiMaio, F., Wang, R. Y.-R., et al. 2013. High-resolution comparative modeling with Rosetta C M. *Structure* 21(10), pp. 1735-1742.

Spoerry, C., Hessle, P., Lewis, M. J., Paton, L., Woof, J. M. and von Pawel-Rammingen, U. 2016. Novel IgG-Degrading Enzymes of the IgdE Protease Family Link Substrate Specificity to Host Tropism of *Streptococcus* Species. *Plos One* 11(10), p. e0164809.

Sriskandan, S., Ferguson, M., Elliot, V., Faulkner, L. and Cohen, J. 2006. Human intravenous immunoglobulin for experimental streptococcal toxic shock: bacterial clearance and modulation of inflammation. *The Journal of Antimicrobial Chemotherapy* 58(1), pp. 117-124.

Staali, L., Bauer, S., Mörgelin, M., Bjorck, L. and Tapper, H. 2006. *Streptococcus pyogenes* bacteria modulate membrane traffic in human neutrophils and selectively inhibit azurophilic granule fusion with phagosomes. *Cellular Microbiology* 8(4), pp. 690-703.

Swanson, J. A. 2008. Shaping cups into phagosomes and macropinosomes. *Nature Reviews. Molecular Cell Biology* 9(8), pp. 639-649.

Trkola, A., Purtscher, M., Muster, T., Ballaun, C., Buchacher, A., Sullivan, N., Srinivasan, K., Sodroski, J., Moore, J. P., and Katinger, H. (1996). Human monoclonal antibody 2G12 defines a distinctive neutralization epitope on the gp120 glycoprotein of human immunodeficiency virus type 1. J. Virol. 70, 1100-1108.

Weineisen, M., Sjöbring, U., Fällman, M. and Andersson, T. 2004. Streptococcal M5 protein prevents neutrophil phagocytosis by interfering with CD11b/CD18 receptor-mediated association and signaling. *Journal of Immunology* 172(6), pp. 3798-3807.

Weitzner, B. D., Jeliazkov, J. R., Lyskov, S., et al. 2017. Modeling and docking of antibody structures with Rosetta. *Nature Protocols* 12(2), pp. 401-416.

Wilson, P. C., de Bouteiller, O., Liu, Y. J., et al. 1998. Somatic hypermutation introduces insertions and deletions into immunoglobulin V genes. *The Journal of Experimental Medicine* 187(1), pp. 59-70.

Woof, J. M. and Burton, D. R. 2004. Human antibody-Fc receptor interactions illuminated by crystal structures. *Nature Reviews. Immunology* 4(2), pp. 89-99.

Yan, Y., Tao, H. and Huang, S.-Y. 2018. HSYMDOCK: a docking web server for predicting the structure of protein homo-oligomers with Cn or Dn symmetry. *Nucleic Acids Research* 46(W1), pp. W423-W431.

EXAMPLES

General Methods/Materials

STAR Methods

| REAGENT or RESOURCE | SOURCE | IDENTIFIER |
|---|---|---|
| Antibodies | | |
| CD19-PE | BD | 555413 |
| CD3-BV510 | BD | 564713 |
| IgG-BV421 | BD | 562581 |
| XOLAIR ® (Omalizumab) | Novartis | 28268 |
| Alexa Fluor ® 647 AffiniPure $F(ab')_2$ Fragment Goat Anti-Human IgG, $F(ab')_2$ fragment specific | Jackson Immunoresearch | 109-606-097 |
| Human IgG (H&L) Secondary Antibody Peroxidase Conjugated Pre-Adsorbed | Rockland (BioNordika) | 609-103-123 |
| Privigen, 100 mg/ml | Behring CSL | 126684 |
| Alexa Fluor ® 647 AffiniPure $F(ab')_2$ Fragment Goat Anti-Human IgG, Fcγ Fragment Specific | Jackson Immunoresearch | 109-606-170 |
| Bacterial and Virus Strains | | |
| MC25 | Collin and Olsén 2000 | |
| Mix'n'go DH5a *E. coli* | Nordic Biolabs | T3002 |
| Group A *Streptococcus* SF370 M1 | ATCC | 700294 |
| Group A *Streptococcus* AP1 M1 | World Health Organization | 40/58; covS truncated |
| Biological Samples | | |
| Donor blood, plasma serum | | |
| Chemicals, Peptides, and Recombinant Proteins | | |
| Phosphate Buffered Saline PBS | GIBCO | 10010-015 |
| Bovine Serum Albumin | VWR | 422351S |
| Sytox-FITC live/dead stain | Thermofischer | S34860 |
| RPMI-1640 | Sigma Aldrich | R8758-6X500ML |
| DMEM | Fischer scientific | 11584516 |
| Chloroquine diphosphate | Fischer scientific | 15368865 |
| Polyetheleneimine (PEI) | Fischer scientific | 11460630 |
| OptiMEM | Life technologies | 31985070 |
| Todd-Hewitt Yeast media | Thermo scientific | CM0189 |
| Oregon Green 488-X succinimidyl ester | Thermo scientific | O6147 |
| Cypher5E NHS ester | Fischer scientific | 11505834 |
| Fibrinogen | Sigma Aldrich | F4883-5G |
| Protein G-HRP | Biorad | 1706425 |
| B1B2B3 | Proteogenix | |
| C1C2C3 | Proteogenix | |
| Supersignal west femto chemiluminescent | Fischer scientific | 10391544 |
| Paraformaldehyde 16% | Fischer scientific | 10751395 |
| Wheat Germ Agglutinin, Alexa Fluor ™ 488 Conjugate | ThermoFisher | W11261 |
| X5 Prolong gold antifade reagent | Fischer scientific | 11569306 |
| Quanti blue solution | Invivogen | rep-qbs |
| Critical Commercial Assays | | |
| Rosettesep B | Stem cell technologies | 15064 |
| Lymphoprep | Stem cell technologies | 7811 |
| Alexa Fluor 647 using the microscale labeling kit | Invitrogen | A30009 |

-continued

| STAR Methods | | |
|---|---|---|
| REAGENT or RESOURCE | SOURCE | IDENTIFIER |
| OneStep RT-PCR kit | Qiagen | 210212 |
| Gammabind Protein G beads | Cytiva | 11564945 |
| Cytometric bead assay | BD Bioscence | 552364 |
| ZymoPURE II ™ Plasmid Midiprep Kit | Nordic Biosite | D4200 |
| Deposited Data | | |
| Experimental Models: Cell Lines | | |
| THP1 cells | Sigma Aldrich | 88081201-1VL |
| THP1-XBlue cells | Invivogen | thp-nfkb |
| HEK293 | Sigma Aldrich | 12022001-1VL |
| Experimental Models: Organisms/Strains | | |
| C57BL/6J mice | Scanbur/Charles River Laboratories | |
| Oligonucleotides | | |
| All nucleotides published previously | | (Smith et al. 2009) |
| Recombinant DNA | | |
| pGFP1 | lab of Dr. Anna Norrby-Teglund | Constitutively expressed GFP |
| Software and Algorithms | | |
| Other | | |

Single B Cell Purification, Baiting, and Isolation

B cell isolation was performed as described previously (Smith et al. 2009), with some modifications. Briefly, 35 ml of blood was drawn (into citrated collection tubes) from a young woman who had recently recovered from a group A streptococcal infection with no post-infection (autoimmune) sequelae. The blood was treated with 2.5 μl/ml Rosettesep B (Stemcell technologies) for 20 mins at room temperature. The blood was then diluted 1:1 in phosphate buffered saline (PBS) and layered onto Lymphoprep gradients. After centrifugation (30 mins at 800×g), the plasma was collected and frozen while the B cell layer (around 7 ml) was removed, diluted with 43 ml of PBS, and centrifuged again. This washing step was repeated twice. The B cells were counted and kept at room temperature for staining (typical yields are 2-5 million cells per 30-40 ml of blood).

B Cell Staining, Baiting, and Sorting

The B cells were concentrated into a final volume of 500 μl in PBS. The cells were then blocked with 5% BSA for 20 minutes before being stained with antibodies against CD19-PE (BD-555413), CD3-BV510 (BD-564713), and IgG-BV421 (BD-562581). The B cells were also labelled with the Sytox-FITC live/dead stain (Thermofischer-S34860). Baiting of the B cells was done using soluble M1 protein isolated from an MC25 group A *Streptococcus* M1 strain. The M1 protein isolation procedure was previously described elsewhere (Collin and Olsen 2000). The M1 protein was directly conjugated to Alexa Fluor 647 using the microscale labeling kit (Invitrogen). In addition to the antibodies and live/dead stains, 0.1 μg/ml of AF694-M1 was added to the cells and the mixture was incubated at 32° C. for 20 minutes (M1 undergoes a conformational change at 4° C. which could obscure important epitopes (Cedervall et al. 1995)). After the incubation, the cells were washed with PBS twice and were kept on ice until further analysis. The gates for sorting were set on a FACSAriaFusion sorter using unstained cells and FMO-1 samples. A total of 100 cells were sorted from 2.5 million B cells directly into 10 μl of water containing RNase inhibitor in 96-well plates and were immediately transferred to a −80° C. freezer. The cells at this point would have been lysed due to osmotic pressure and the RNA stabilized in solution.

Reverse Transcription, Family Identification, and Cloning

The cells previously frozen in plates were thawed on ice and RT-PCR was performed using the OneStep RT-PCR kit (Qiagen) protocol without modification. The primer sequences used in the PCR steps were taken directly from the Smith et al (2009) paper without any modifications. After the RT-PCR, the nested PCR was performed and the bands corresponding to the variable regions of the heavy and light chains were sequenced to identify the antibody families. Family-specific cloning primers were used to clone the variable chains into the plasmids containing the constant regions of the heavy and light chains. The expression plasmids were generously donated by Dr. Patrick Wilson's group.

General Cell Culture and Transfection

THP1 cells (Leukemic monocytes) were maintained in RPMI media supplemented with L-Glutamine and 10% FBS. The cells were kept at a cell density between $5\text{-}10\times10^5$ cells per ml. THP1-XBlue cells were maintained like regular THP1 cells. HEK293 cells were maintained in DMEM supplemented with L-Glutamine and 10% FBS. The cells were never allowed to grow to 100% confluency. The day before transfection, $8\times10^6$ cells were plated in circular 150 mm dishes. This transfection format allowed for the most efficient antibody recovery.

Transfection, Expression, and Purification

In total, 10 antibody construct pairs were successfully generated from 100 starting cells. The Antibody pairs were transformed into Mix'n'go *E. coli*. Transformant colonies were verified by sequencing and the plasmids were further propagated and DNA was extracted using a Zymoresearch midiprep kit. Plasmid pairs encoding full mature antibodies were co-transfected into HEK293 cells using the PEI transfection method (https://www.addgene.org/protocols/transfection/). Cells were briefly treated with 25 μM Chloroquine for 5 hours. Thereafter, 20 μg of heavy and light chain expression plasmid DNA were diluted in OptiMEM (Life technologies) media containing polyetheleneimine (PEI) at a 1:3 ratio (for 50 μg of DNA, 114 μl of a 1 mg/ml PEI stock was used). The cells were incubated at 37° C. for 18 hours before they were washed 2 times with PBS and the DMEM media was exchanged with OptiMEM. The cells were incubated for a further 72 hours before the supernatants were collected. The antibodies in the supernatants were purified using Protein G beads in a column setup. The antibodies were then titrated by comparing their concentrations on an SDS-PAGE to serial dilutions of a known concentration of XOLAIR® (Omalizumab) (commercially bought Omalizumab, stored at 150 mg/ml).

Bacterial Strains, Growth, and Transformation

*Streptococcus pyogenes* strain SF370 (emm1 serotype) and AP1 (emm1 serotype) was grown in Todd-Hewitt Yeast media (THY) at 37° C. The bacteria were maintained on agar plates for 3 weeks before being discarded. We chose to use SF370 in all of our experiments since it is an M1 serotype strain lacking protein H which is a complicating factor (due to its strong Fc binding capacity and extensive homology with M protein (Åkesson et al. 1990)). For experiments, overnight cultures were prepared in THY and were diluted 1:20 on the day of the experiments. After dilution, three hours of growth at 37° C. ensured that the bacteria were in mid-log growth. For the generation of GFP-expressing strains, the SF370 and its ΔM isogenic counterpart were grown to mid-log before being washed with ice-cold water. The electrocompetent bacteria were electroporated with 20 μg of the pGFP1 plasmid and plated on Erythromycin supplemented THY plates. The successful transformants were fluorescent when examined under ultraviolet light. Heat killing the bacteria was done by growing the cultures to mid log, washing them once in PBS and incubating them on ice for 5 minutes. The bacteria were then heat shocked at 80° C. for 5 minutes before being placed on ice for 15 minutes. For the phagocytosis assay, the heat killed bacteria were centrifuged at 8000×g for 3 minutes and resuspended in Na-medium (5.6 mM glucose, 127 mM NaCl, 10.8 mM KCl, 2.4 mM $KH_2PO_4$, 1.6 mM $MgSO_4$, 10 mM HEPES, 1.8 mM $CaCl_2$; pH adjusted to 7.3 with NaOH). Heat-killed bacteria were stained with 5 μM Oregon Green 488-X succinimidyl ester (Thermofischer) at 37° C. under gentle rotation and protected from light for 30 min. The bacteria were then centrifuged and resuspended in Sodium carbonate buffer (0.1 M, pH 9.0) for an additional staining step with the pH-sensitive dye CypHer5E (Fischer scientific). This was used at a concentration of 7 μg/ml in a volume of 1.5 ml for 2 h at room temperature under gentle rotation, protected from light. The samples were washed once with Na-medium to remove excess dye and stored at 4° C. for later use.

Antibody Screening and Flow Cytometry

For ELISAs: ELISA plates were coated overnight with human fibrinogen (25 μg/ml in 100 μl of PBS) at 4° C. The following day, the coating buffer was washed with PBST and the plates were coated with 10 μg/ml M1, which had been purified from MC25 culture supernatants (Collin and Olsén 2000). After a 1-hour incubation at 37° C., the wells were washed 3 times with PBST and blocked with 2% BSA in 300 μl PBST for 30 minutes. After blocking, 300 μl of antibody containing supernatants were added to the wells, or diluted donor plasma as a control. The samples were incubated for 1 hour at 37° C., washed, and a solution of Protein G-HRP (diluted 1:3000) was added to the wells and incubated at 37° C. for 1 hour. The samples were then washed and developed with 100 μl developing reagent (20 ml Substrate buffer NaCitrate pH 4.5+1 ml ABTS Peroxide substrate+0.4 ml $H_2O_2$). Absorbance was read at $OD_{450}$ following 5-30 minutes of color development at room temperature.

For ELISA using the shorter M1 B1B2B3 and C1C2C3 constructs, open reading frames encoding for the B1B2B3 repeats of the M1 protein (UniProt ID: Q99XV0, emm1; amino acids 132-194) and the C1C2C3 repeats (amino acids 229-348) were cloned at the Lund Protein Production Platform (LP3) (Lund, Sweden). The encoding sequences were ordered as a synthetic construct from Genscript (NJ, USA), and cloned into a pNIC28-Bsa4-based vector incorporating a tandem affinity purification tag (histidine-hemagglutinin-StrepII-tobacco etch virus protease recognition site) at the C-terminus of the construct. The constructs were expressed in Luria-Bertani Broth (Difco) supplemented with 50 μg/ml of kanamycin at 25° C. in *E. coli* TUNER (DE3) cells. For protein expression the temperature was lowered to 18° C. and the expression induced with 0.1 mM IPTG at $OD_{600}$ 0.6. Expressed cells were harvested and resuspended in phosphate buffer (50 mM $NaPO_4$, 300 mM NaCl, 20 mM imidazole, pH 8.0) supplemented with EDTA-free Complete Protease Inhibitor tablets (Roche). The cells were lysed using a French pressure cell at 18,000 psi. The lysate was cleared via ultracentrifugation (Ti 50.2 rotor, 244,000×g, 60 min, 4° C.) and subsequently passed through a 0.45 μm filter prior to loading on a HisTrap HP column (GE Healthcare). The column was washed with 20 column volumes (CVs) of phosphate buffer, and bound protein was eluted using a gradient of 0-500 mM imidazole in phosphate buffer. Fractions containing the desired protein were pooled, and dialyzed against 1× phosphate buffer saline (PBS; 10 mM phosphate buffer, 2.7 mM KCl, 137 mM NaCl) pH 7.3, and stored at −80° C. These constructs were subsequently used to coat the ELISA wells or as competition for the M antibodies.

For flow cytometric screening: Overnights of SF370-GFP bacteria or its ΔM counterpart were diluted 1:20 into THY and grown until mid-log. 100 μl of the bacteria were distributed into wells of a 96 well plate. Antibodies purified from cell culture supernatants were diluted to 5 μg/ml and were digested with 1 μg/ml of IdeS for 3 hours at 37° C. The digested antibodies were further diluted 1:10 into the bacterial suspension. Reaching a final concentration of 0.5 μg/ml. The bacteria were incubated for 30 minutes at 37° C. before being washed twice with PBS. AF647-conjugated Fab α-Fab antibody fragments were used as secondary antibodies to detect binding of the primary α-M antibodies. After a 30-minute incubation with the Fab α-Fab fragments, the bacteria were washed and analyzed on a Cytoflex flow cytometer (Beckman coulter). The gates for the GFP-expressing bacteria were set using the SF370 parent strain (not expressing the GFP plasmid). GFP-expressing bacteria within the GFP-expressing gate were assessed for antibody staining (APC channel). Antibody staining reflects the presence of surface-bound primary-secondary antibody complexes and is indicative of bound anti-M antibodies.

For western blotting: Antibody reactivity to linear epitopes was assessed by probing the lysates of SF370 and its ΔM mutant using western blotting. Briefly, pellets of logarithmically grown bacteria were incubated with phospholipase C for 30 minutes in PBS until the lysates became clear. The lysates were sonicated and cleared by centrifugation (15,000×g for 3 minutes). We loaded 40 μg of 5 replicate sets of SF370 vs ΔM mutant protein on a gradient SDS-PAGE gel (4-20%). The gel electrophoresis was run for 60 minutes to achieve protein separation. The proteins were transferred from the gel to a PVDF membrane which was blocked for 45 minutes with 5% skimmed milk in PBST. The replicate lanes of the membrane were then cut and probed with 2 or 10 μg/ml of XOLAIR® (Omalizumab), Ab25, 32, 49 or IVIgG overnight at 4° C. The membranes were washed 3 times with PBST and probed with the secondary HRP-conjugated goat anti-human IgG secondary (Rockland) antibody for 1 hour at room temperature. The secondary was later washed, and the membrane developed using a chemilumunescence reagent (WestFemto substrate, Thermofischer).

Agglutination Assays

For Agglutination Assays:

Overnight cultures of SF370 and its ΔM strain were diluted 1:5 in RPMI and were treated with 100 μg/ml of the anti-M antibodies, or with 5% donor plasma. It is crucial for this series of experiments that the bacteria are incubated in a cuvette and are not shaken or vortexed during incubation. At indicated time points, the $OD_{600}$ of the bacteria was measured and at the 3.5 hour mark the cuvettes were photographed.

For Aggregate Dissolution Experiments

SF370 bacteria were grown overnight, diluted 1:20 in THY and left to grow for two hours. The bacteria were then supplemented with 100 μg/ml of the appropriate antibody. Two hours after inoculation, the bacteria were vortexed, imaged (randomly) and the aggregate areas were analyzed using Image J.

SIM Imaging

Logarithmic phase bacteria were sonicated (VialTweeter; Hielscher) for 0.5 minutes to separate any aggregates and incubated fixed in 4% paraformaldehyde for 5 minutes on ice. The bacteria were thereafter washed with PBS twice (10,000×g for 3 min). SF370 was stained with Alexa Fluor 647-conjugated wheat germ agglutinin (WGA). Bacteria were incubated with IdeS-cleaved XOLAIR® (Omalizumab), Ab25, Ab32, and Ab49 and stained with fluorescently labelled IgGFab or IgGFc specific F(ab')2 fragments (DyLight488-conjugated anti-human IgGFc or IgGFab; Jackson ImmunoResearch Laboratory). Samples were mounted on glass slides using Prolong Gold Antifade Mountant with No. 1.5 coverslips. Images of single bacteria were acquired using an N-SIM microscope with LU-NV laser unit, CFI SR HP Apochromat TIRF 100× Oil objective (N.A. 1.49) and an additional 1.5× magnification. The camera used was ORCA-Flash 4.0 sCMOS camera (Hamamatsu Photonics K.K.) and the images were reconstructed with Nikon's SIM software on NIS-Elements Ar (NIS-A 6D and N-SIM Analysis). Images of the bacteria were acquired with 488 and 640 nm lasers. For site localization, single bacteria were manually identified and imaged in time series with 50 frames. The analysis pipeline for site localization was implemented in Julia and is available on GitHub (Kumra Ahnlide et al manuscript 2020). A cut off of initial signal-to-noise ratio (SNR) was set to 0.3 and timeframes included were the ones with at least 70% of the initial SNR.

Binding Curves

SF370 bacteria were grown to mid log, washed and 10 ml of culture were concentrated into 1000 μl of PBS. The bacteria were stained with halving serial dilutions of the anti-M antibodies. 30 μl of bacteria were used per every 100 μl of IdeS treated antibody. The staining was performed at 4° C. for 30 minutes (with shaking) before the bacteria were washed and stained with an excess of AF647-conjugated Fab anti-Fab fragments in a volume of 30 μl for 30 minutes at 4° C. with shaking. The bacteria were then diluted to 250 μl in PBS and analyzed by flow cytometry. Theoretical fit was done in MATLAB using fminsearch for an ideal binding curve with the dissociation constant as an unknown variable.

Crosslinking of Antibody F(Ab')2 Fragments to the M1 Protein

For the crosslinking of Ab25, Ab32 and Ab49 F(ab')2 fragments to the M1 protein, we used two different preparations of the M1 protein; one expressed and purified as recombinant in *E. coli* as described for the B1B2B3 and C1C2C3 constructs above, and one purified from the culture supernatant of the *S. pyogenes* MC25 strain (Collin and Olsén 2000). The antibody F(ab')2 fragments were cleaved and purified from the expressed intact antibodies using the FragIT-kit with Fc-capture columns (Genovis) according to the manufacturer's instructions. For crosslinking, 25 μg of the recombinant M1 protein or 8 μg of the MC25 M1 protein were incubated with 5 μg of the respective F(ab')2 fragments in 1×PBS pH 7.4 at 37° C., 800 rpm, 30 min. Heavy/light disuccinimidylsuberate (DSS; DSS-H12/D12, Creative Molecules Inc.) resuspended in dimethylformamide (DMF) was added to final concentrations 250 and 500 μM and incubated for a further of 60 min at 37° C., 800 rpm. The crosslinking reaction was quenched with a final concentration of 50 mM ammonium bicarbonate at 37° C., 800 rpm, 15 min.

Sample Preparation for MS

The crosslinked samples mixed with 8 M urea and 100 mM ammonium bicarbonate, and the cysteine bonds were reduced with 5 mM TCEP (37° C. for 2 h, 800 rpm) and alkylated with 10 mM iodoacetamide (22° C. for 30 min, in the dark). The proteins were first digested with 1 μg of sequencing grade lysyl endopeptidase (Wako Chemicals) (37° C., 800 rpm, 2h). The samples were diluted with 100 mM ammonium bicarbonate to a final urea concentration of 1.5 M, and 1 μg sequencing grade trypsin (Promega) was added for further protein digestion (37° C., 800 rpm, 18 h). Samples were acidified (to a final pH 3.0) with 10% formic acid, and the peptides purified with C18 reverse phase spin columns according to the manufacturer's instructions (Macrospin columns, Harvard Apparatus). Peptides were dried in a speedvac and reconstituted in 2% acetonitrile, 0.2% formic acid prior to mass spectrometric analyses.

Liquid Chromatography Tandem Mass Spectrometry (LC-MS/MS)

All peptide analyses were performed on Q Exactive HF-X mass spectrometer (Thermo Scientific) connected to an EASY-nLC 1200 ultra-high-performance liquid chromatography system (Thermo Scientific). Peptides were loaded onto an Acclaim PepMap 100 (75 μm×2 cm) C18 (3 μm, 100 Å) pre-column and separated on an EASY-Spray column (Thermo Scientific; ID 75 μm×50 cm, column temperature 45° C.) operated at a constant pressure of 800 bar. A linear gradient from 4 to 45% of 80% acetonitrile in aqueous 0.1% formic acid was run for 65 min at a flow rate of 350 nl min−1. One full MS scan (resolution 60000 @ 200 m/z; mass range 390-1 210m/z) was followed by MS/MS scans (resolution 15000 @ 200 m/z) of the 15 most abundant ion signals. The precursor ions were isolated with 2 m/z isolation width and fragmented using HCD at a normalized collision energy of 30. Charge state screening was enabled, and precursors with an unknown charge state and a charge state of 1 were rejected. The dynamic exclusion window was set to 10 s. The automatic gain control was set to 3e6 and 1e5 for MS and MS/MS with ion accumulation times of 110 ms and 60 ms, respectively. The intensity threshold for precursor ion selection was set to 1.7e4.

Computational Modeling

Several protocols of Rosetta software suit (Koehler Leman et al. 2019) were employed for macromolecular modeling of this study. To model the full-length antibodies, first the antigen-binding domains were characterized using Rosetta antibody protocol (Weitzner et al. 2017). Then, comparative models have been generated for both heavy and light chains using RosettaCM protocol (Song et al. 2013) and aligned on the antigen-binding domains to represent the initial structure of the antibody. HSYMDOCK (Yan et al. 2018), and DaReUS_loop (Karami et al. 2019) web servers were used for symmetric docking of the Fc-domains and to model the hinge regions, respectively. Finally, 4K models were produced for each antibody as the final refinement and the top-scored models were selected based on XLs derived from mass spectrometry combined with rosetta energy scores. Moreover, to characterize the M1 antibody interactions, TX-MS protocol were used (Hauri et al. 2019), through which 2K docking models were generated and filtered out using distance constraints from DDA data. A final round of high-resolution modeling was performed on top models to repack the sidechains using RosettaDock protocol (Gray 2006).

Fluorescent XOLAIR® (Omalizumab) Competition Experiments

Logarithmically grown SF370 bacteria were heat killed and labelled with Oregon Green (as described previously). The bacteria were mixed with antibodies or plasma/IVIG and incubated for 30 minutes at 37° C. while shaking. Fluorescently conjugated XOLAIR® (Omalizumab) (conjugated to Alexafluor 647 using the protein labeling kit (Invitrogen) according to the manufacturer's instructions) was then added to the bacteria at a concentration of 100 μg/ml for an additional 30 minutes before being directly analyzed by flow cytometry. For experiments in which Fabs were used, the Fabs were generated using the Fabalactica digestion kit (Genovis) according to manufacturer's instructions.

Phagocytosis Assay

The phagocytosis experiments were performed using persistent association normalization (de Neergaard et al. 2019). Prior to opsonization, the CypHer5E- and Oregon Green-stained SF370 bacteria were sonicated for up to 5 min (VialTweeter; Hielscher) to disperse any large aggregates of bacteria. Sonication was deemed sufficient when clump dispersal was confirmed by microscopy. Staining as well as bacterial count (events/μl in the FITC+ve gate) was assessed by flow cytometry (CytoFLEX, Beckman-Coulter). The pH responsiveness of CypHer5E was tested by measuring the bacterial fluorescent staining in the APC channel before and after the addition of 1 μl of sodium acetate (3 M, pH 5.0) to 100 μl of bacterial suspension. The presence of an acid induced shift in fluorescence indicated successful staining. On the day of experiments, the appropriate number of bacteria were opsonized to suit each experiment. The opsonization with our M-specific antibodies, XOLAIR® (Omalizumab) or with IVIG was performed at 37° C. for 30 minutes. For experiments with a variable MOP, serial dilutions of the opsonized bacteria were made and used to incubate with the THP-1 cells. By gating on the leukocyte population, specifically on single cells, we were able to group the cells into those associated with bacteria (FITC positive) and with internalized bacteria (FITC and APC positive). In experiments where antibody concentration was the variable, serial dilutions of the antibodies were made in Na-medium in 96 well plates and the bacteria were directly added to the antibodies for opsonization. THP1 cells were washed in PBS on the day of the experiment and resuspended in Na-medium. The concentration of THP-1 cells was measured prior to phagocytosis by flow cytometry and adjusted to 2000 cells/μl (100 000 cells per well). The cells were then added to the 96-well plates previously prepared with varying concentrations of previously opsonized bacteria (MOP) or with different antibody concentrations. Finally, 50 μl of THP-1 cells were added on ice resulting in a final phagocytic volume of 150 μl. After a 5-minute incubation on ice, the plate was directly transferred to a shaking heating block set to 37° C. while being protected from light or kept on ice as a control for internalization. Phagocytosis was stopped by putting the samples on ice for at least 15 min before data acquisition. Three experiments were performed to assess the association curves and four experiments were performed at MOP 400 to compare different antibodies. Flow cytometric acquisition was performed using a CytoFLEX (Beckman-Coulter) with 488 nm and 638 nm lasers and filters 525/40 FITC and 660/10 APC. Threshold was set at FSC-H 70,000 for phagocytosis and for bacteria FSC-H 2000 and SSC-H 2000. Gain was set to 3 for FITC and 265 for APC. Acquisition was set to capture at least 5 000 events of the target population with a velocity of 30 μl/min taking approximately 30 min to assess all samples. Throughout the data acquisition the 96-well plate was kept on an ice-cold insert to inhibit further phagocytosis.

NF-κB Activity Luciferase Assay

THP-XBlue-CD14 (Invivogen) cells were seeded at a density of 200,000 cells per well in 96 well plates. The cells were treated with the appropriate antibodies (at 0.5 μg/ml) with or without M1 protein (2 μg/ml) for 18 hours at 37° C. After the incubation, 20 μl of the cell supernatant were aspirated and mixed with the developing reagent, as described by the assay instructions (QuantiBlue solution, Invivogen). The samples were incubated at 37° C. until development was appropriate and the OD650 measurement of the samples was done using a multi-well spectrophotometer.

Animal Model

All animal use and procedures were approved by the local Malmö/Lund Institutional Animal Care and Use Committee, ethical permit number 03681-2019. Nine-week-old female C57BL/6J mice (Scanbur/Charles River Laboratories) were used. Monoclonal antibody Ab25 (0.4 mg/mouse), or intravenous immunoglobulin (10 mg/mouse) was administered intraperitoneally 6 h pre-infection. *S. pyogenes* AP1 was grown to logarithmic phase in Todd-Hewitt broth (37° C., 5% CO2). Bacteria were washed and resuspended in sterile PBS. $10^6$ CFU of bacteria were injected subcutaneously into the scruff leading to systemic infection within 24h. Mice were sacrificed 24 h post infection, and organs (blood, livers, spleens, and kidneys) were harvested to determine the degree of bacterial dissemination. The blood cell counts were analyzed by flow cytometry. Cytokines were quantified using a cytometric bead assay (CBA mouse inflammation kit, BD) according to manufacturer instructions.

Figure 2:
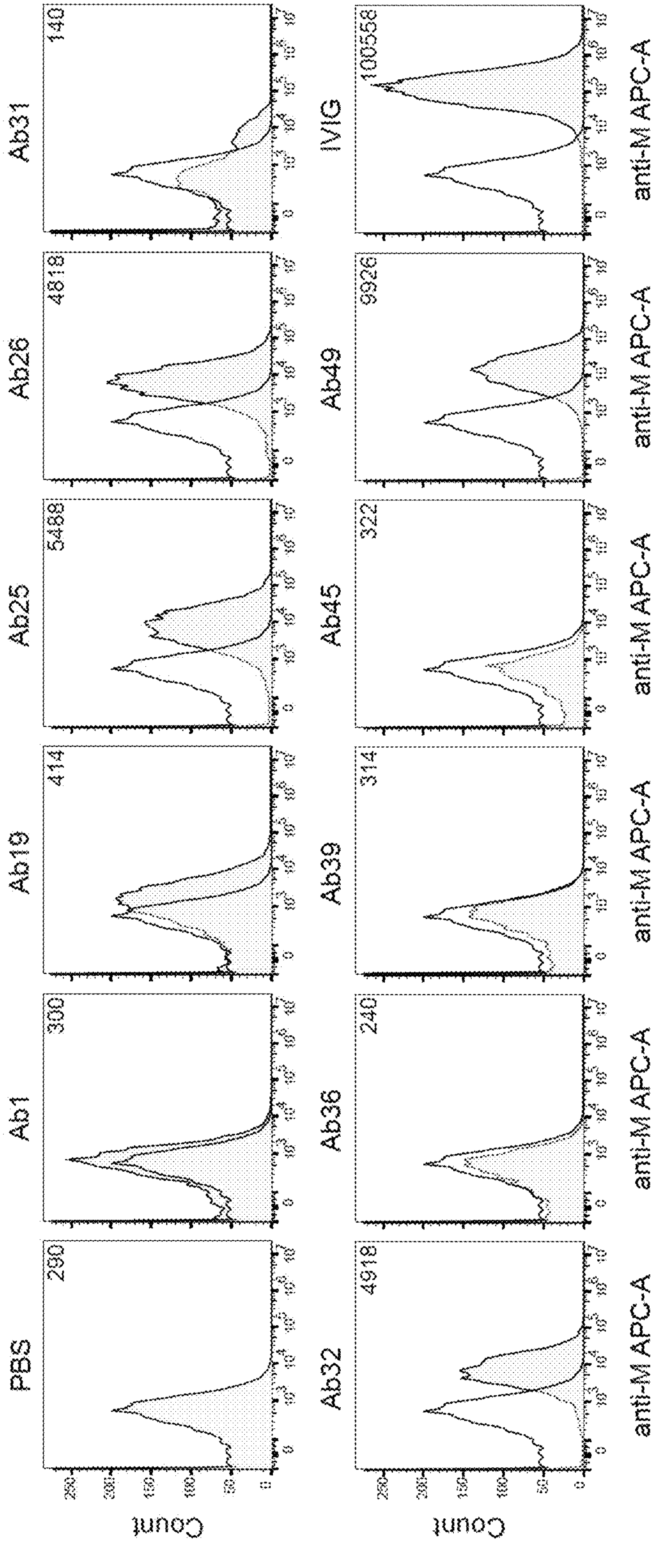
FIG. 2. SF370 (GFP-transformed) bacteria were stained with the shown antibody and a secondary Fab anti-Fab antibody (conjugated to AF647) was used to generate the signal for flow cytometric analysis. The number in the upper right corner of the flow histograms indicates the median fluorescence intensity.
Figure 3:
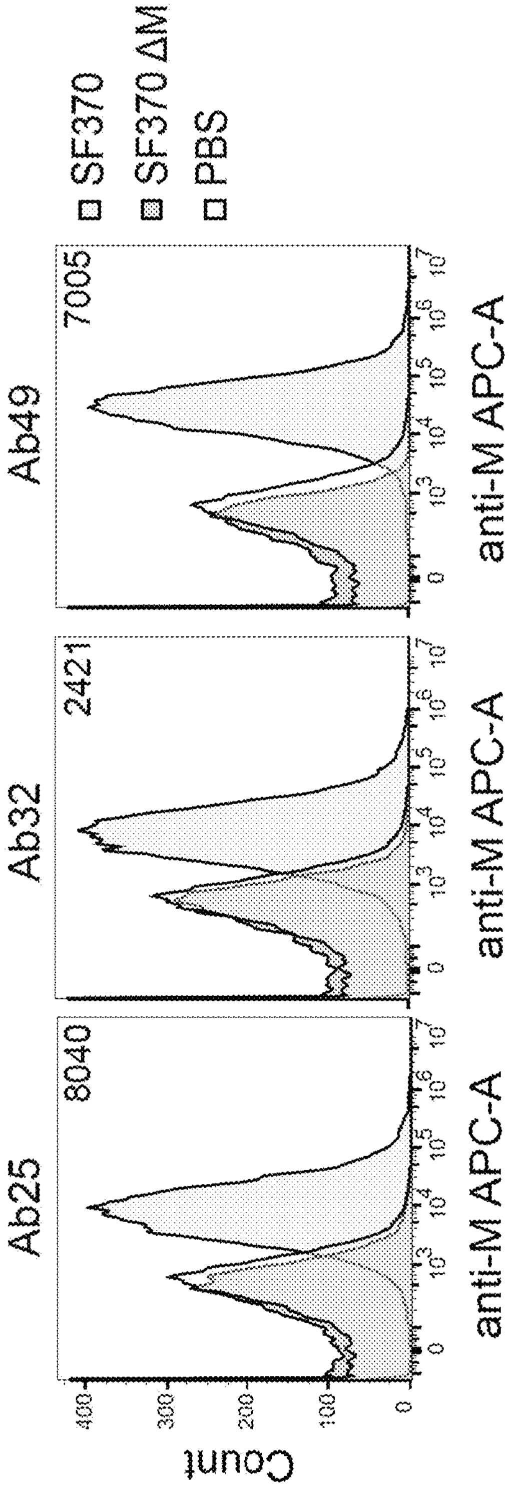
FIG. 3. The specificity of the successful antibodies was assessed by comparing the staining of WT SF370 and ΔM SF370.
Figure 4:
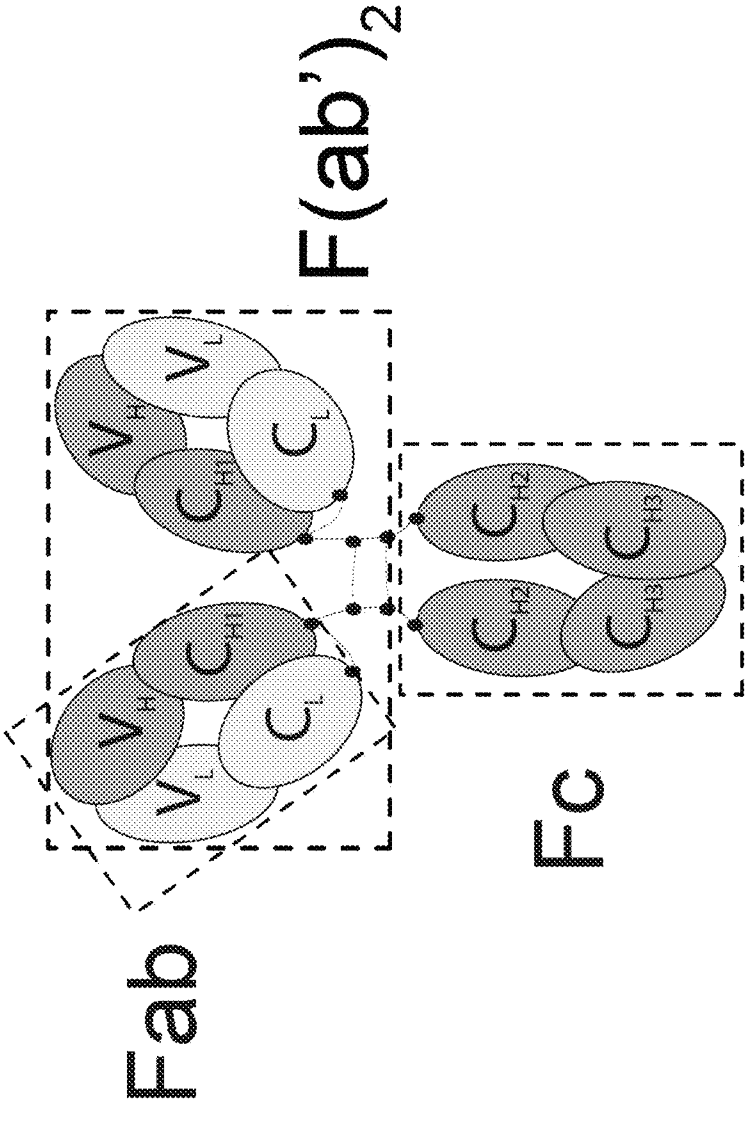
FIG. 4. Schematic representation of an IgG antibody.
Figure 5:
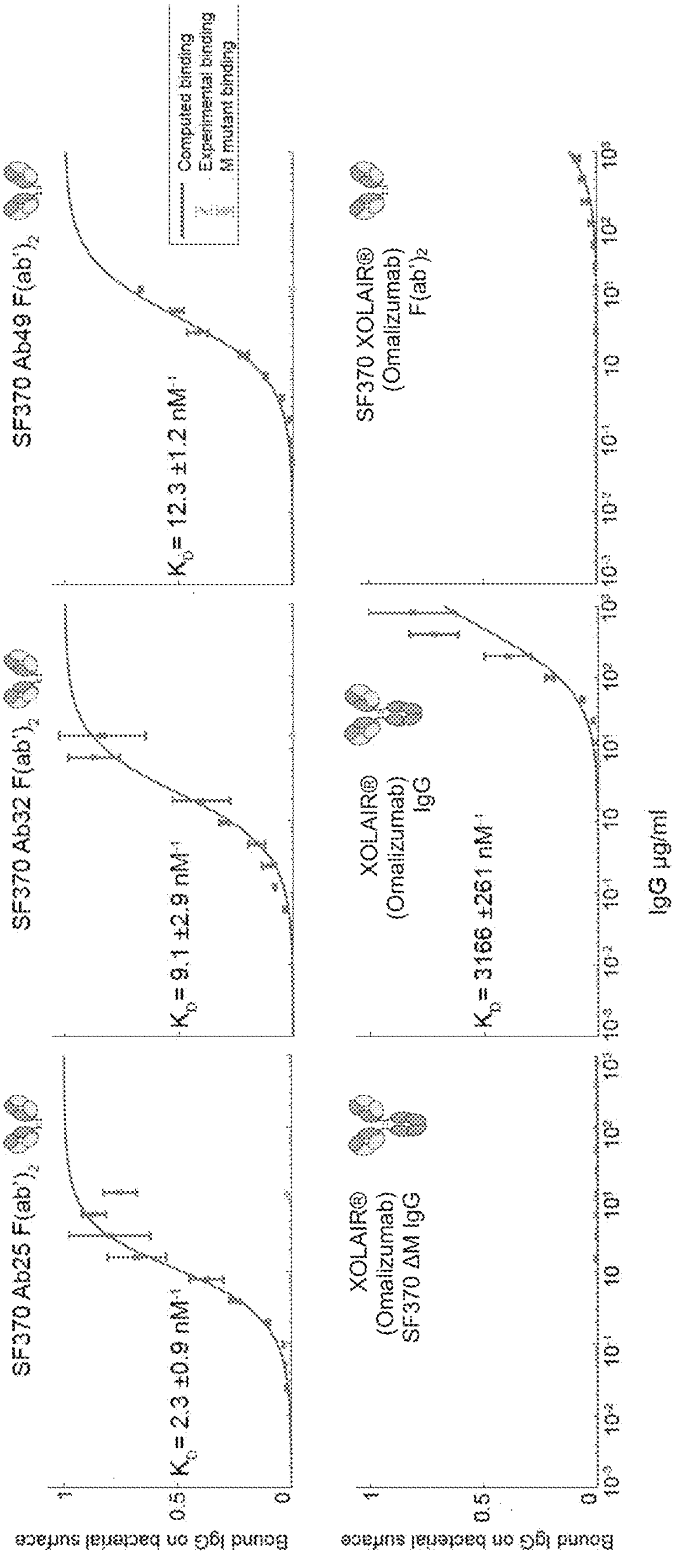
FIG. 5. Plots showing the measured binding (dark error bars) of specific antibody to mid-log grown SF370 or the M mutant as a function of the total antibody concentration, together with a fitted binding curve using least squares method (dark curve). The bottom three plots are controls with a non-specific antibody that have been normalized according to the fitting of the bottom left binding curve, making the binding comparable across the three controls. $K_D$ values for the fitting are given in each plot, together with a confidence interval calculated using the Bootstrap method. The antibodies (antibody fragments) used are shown in the top-right side of each graph.
Figure 29:
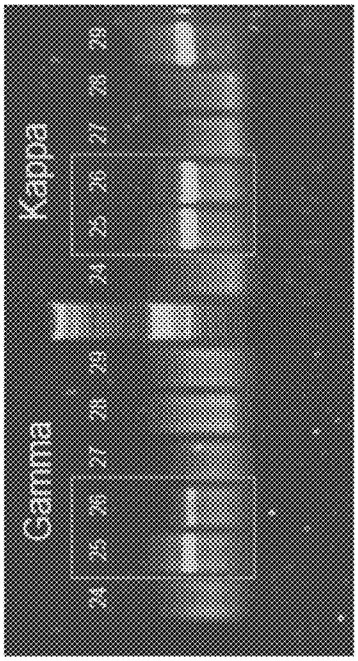
FIG. 29. Ten antibody pairs from cloning RT-PCR of the variable regions of the heavy and light chains.
Figure 29:
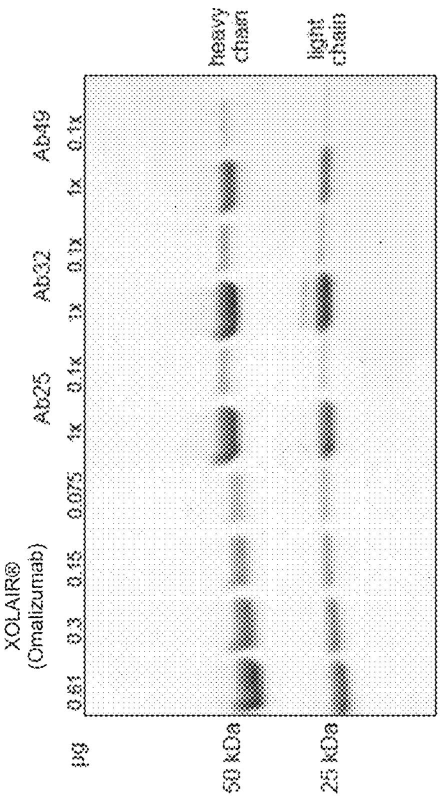
Figure 30:
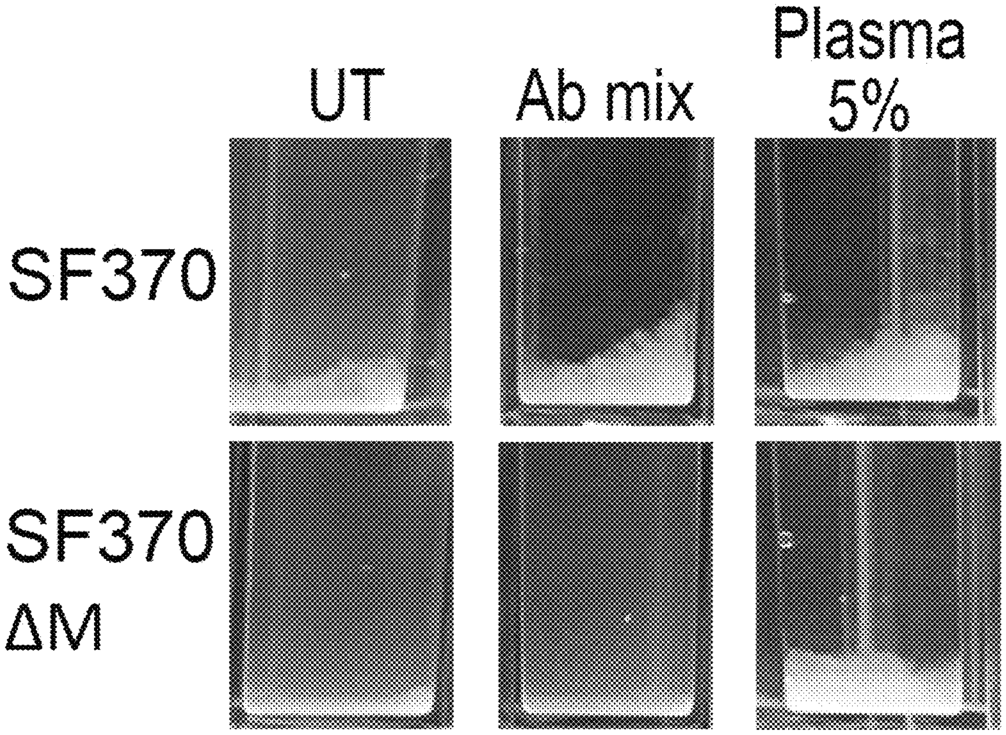
FIG. 30. Images of the cuvettes used to measure agglutination. SF370 overnight cultures were diluted 1:5 into THY and incubated with antibodies (100 μg/ml) for 3 hours in plastic cuvettes at 37° C. before measuring their $OD_{600}$. The agglutination effects of the antibody mix (Ab25,32 and 49 at 100 μg/ml each) were compared on WT and ΔM bacteria. Donor plasma was used as a positive control.

Example 1. Antigen-Baiting for the Development of Human Single Cell-Derived M-Specific Antibodies To understand what constitutes a protective antibody towards GAS infection, we wanted to generate functional human antibodies and analyze their effects on virulence. We choose M protein as a target antigen, with a donor that had successfully cleared a streptococcal infection as a source of M protein-specific antibodies. To identify human antibodies with specificity towards streptococcal M protein, we isolated M-reactive B cells by baiting donor B cells with fluorescently conjugated M protein. We sorted live single $CD19^+$ $CD3^-$ $IgG^+$ $M^+$ B cells (FIG. 1). Cloning RT-PCR of the variable regions of the heavy and light chains yielded ten antibody pairs. SDS-PAGE analysis of the antibodies after expression in HEK293 cells showed correct migration patterns, indicating proper expression of intact antibodies (FIG. 29). Four antibodies showed clear reactivity to surface-bound M1 protein on GAS (strain SF370), the most common M protein among GAS isolates (FIG. 2). Further experiments with three selected antibodies using a ΔM SF370 mutant strain lacking M1 protein, demonstrated the specificity of the interaction between Ab25, 32, and 49 and M1 (FIG. 3). We measured the antibody binding affinities to the surface of SF370 with either intact antibodies or $F(ab')_2$ fragments (FIG. 4), the latter to avoid contribution from M1's binding to IgGFc (Åkesson et al. 1994). Intact XOLAIR® (Omalizumab, anti-IgE) showed a $K_D$ of $3.2\times10^{-6}$ $M^{-1}$, signifying a low binding affinity in concordance with previous reported IgGFc affinity for purified M1 protein ($3.4\times10^{-6}$ $M^{-1}$) (Åkesson et al. 1994). $F(ab')_2$ fragments of Ab25, 32, and 49 had significantly higher affinities for M1; $2.3\times10^{-9}$, $9.1\times10^{-9}$, and $12.3\times10^{-9} M^{-1}$, respectively (FIG. 5).

Example 2. Characterization of Anti-M Antibodies

Figure 6:
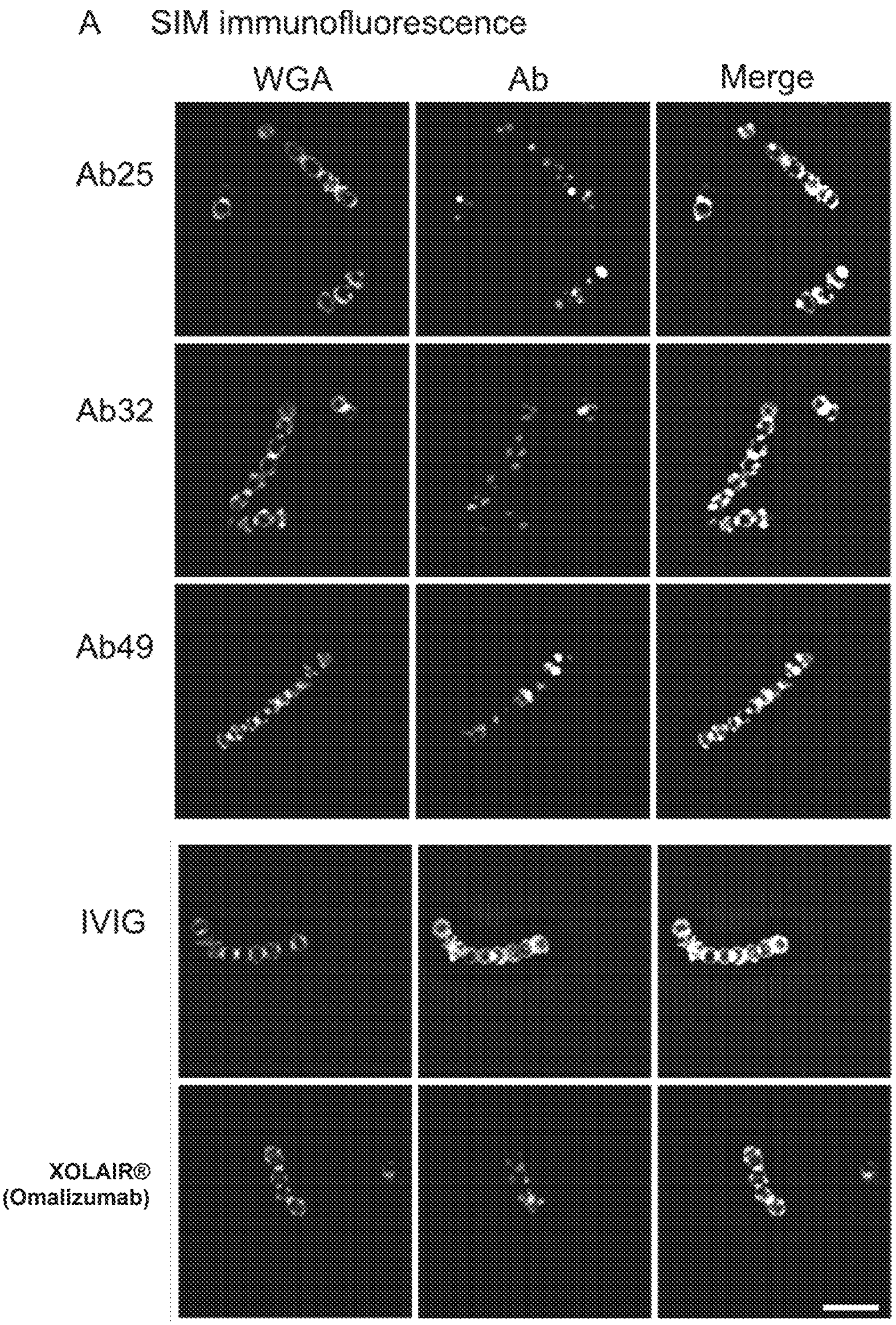
FIG. 6. Structured illumination microscopy (SIM) super resolution imaging was performed on bacteria stained with IdeS cleaved α-M antibodies and probed with Dylight488-conjugated Fab α-Fab fragments. AF647-conjugated WGA was used as a counter stain to highlight the bacterial structures. The scale bar represents 5 μm.
Figure 7:
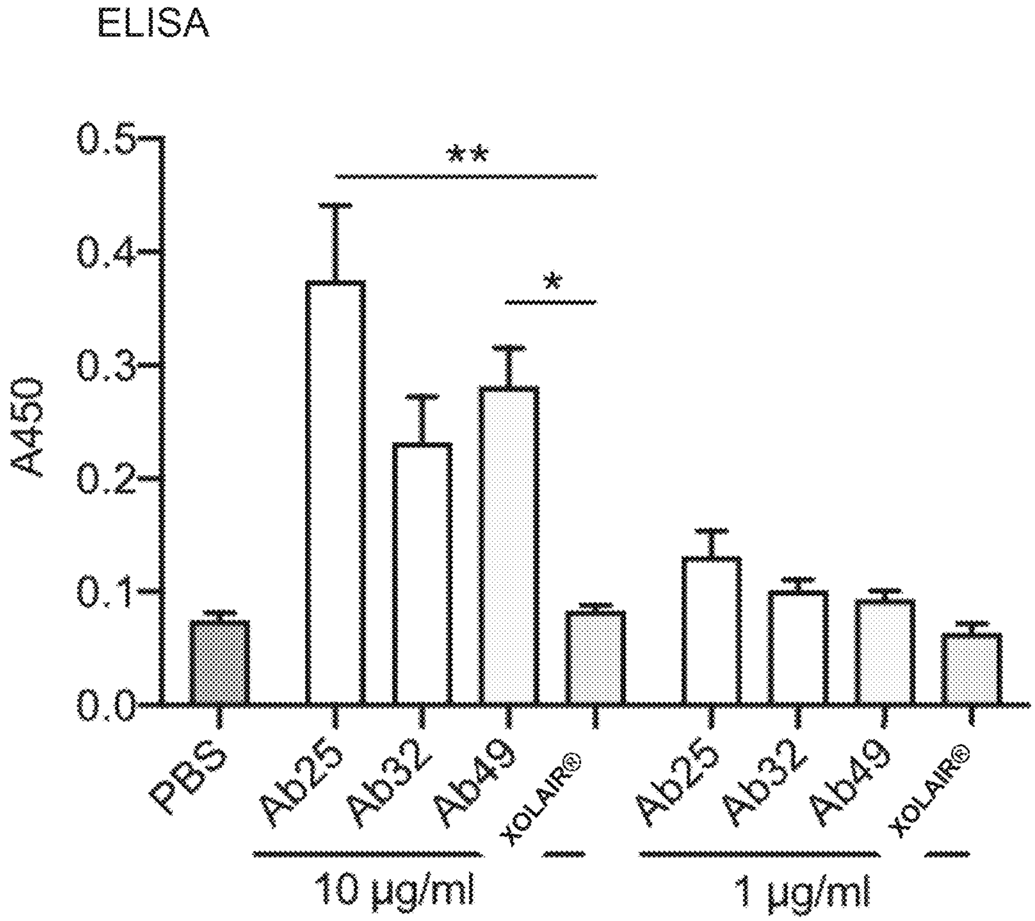
FIG. 7. Antibodies were tested for reactivity against the M protein in an ELISA assay. XOLAIR® (Omalizumab) and PBS were used as negative controls. The absorbance at 450 nm was measured and plotted as an average of quadruplicate wells.
Figure 8:
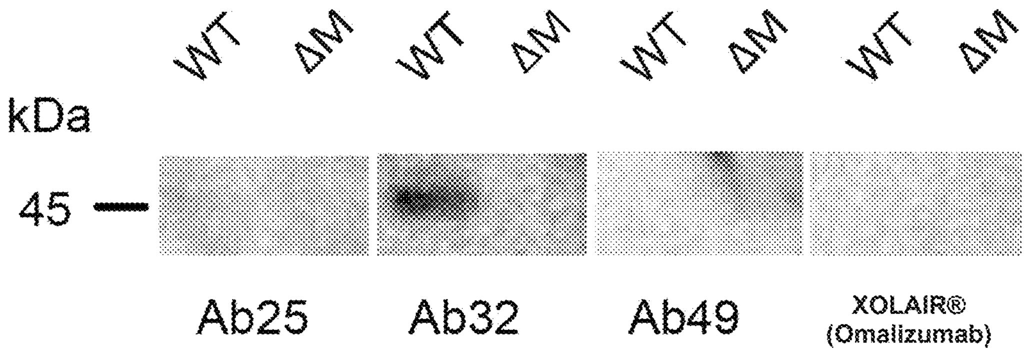
FIG. 8. Probing with the mentioned antibodies at a concentration of 2 μg/ml. Protein lysates from logarithmically grown WT and ΔM SF370 bacteria were run on SDS-PAGE and after blotting, were probed with the antibodies.

To characterize the identified anti-M1 antibodies, we performed a panel of biochemical and immunological assays. We used structured illumination microscopy (SIM) immunofluorescence (IF) to visualize the anti-M binding pattern on the surface of SF370. Interestingly, M protein shows a similar punctate distribution along the surface of the organism with all the monoclonal antibodies, including the Fc-mediated XOLAIR® (Omalizumab) binding (FIG. 6). IVIG, which contains pooled IgG from thousands of donors, instead stained the whole surface of the bacteria indicating expected polyspecific coverage (FIG. 6). Only Ab25 showed reactivity with M protein using an anti-M ELISA (FIG. 7), whereas Ab32 showed the best binding to M protein in Western blot (WB) experiments (FIG. 8). Taken together, the data from IF, ELISA, and WB indicate that the three monoclonals bind to different epitopes on M protein.

Figure 9:
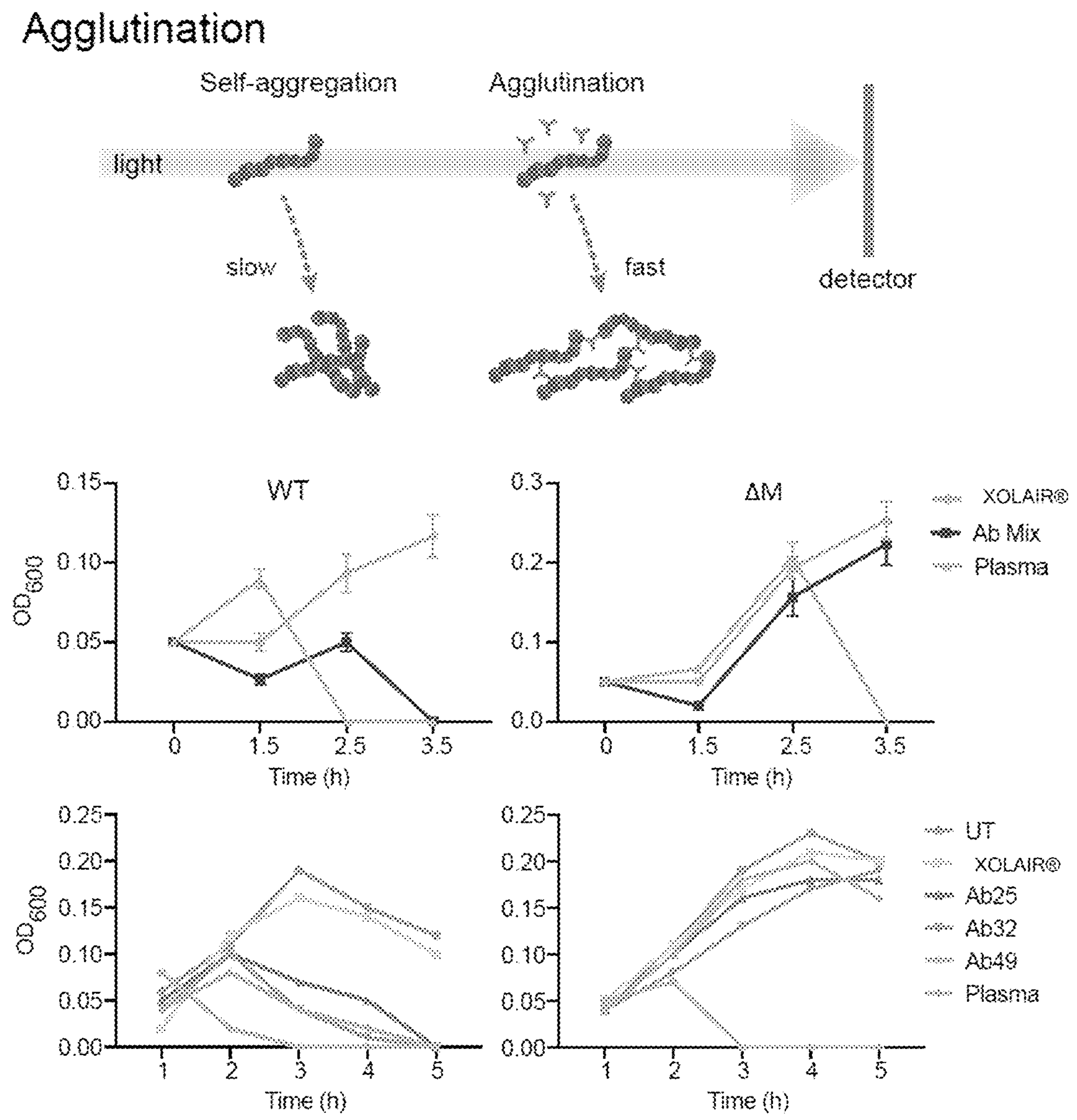
FIG. 9. Time course analysis of the effect of the antibody mix (upper graphs) or individual antibodies (lower graphs) used at 100 μg/ml each on bacterial agglutination was assessed by $OD_{600}$ measurements.
Figure 31:
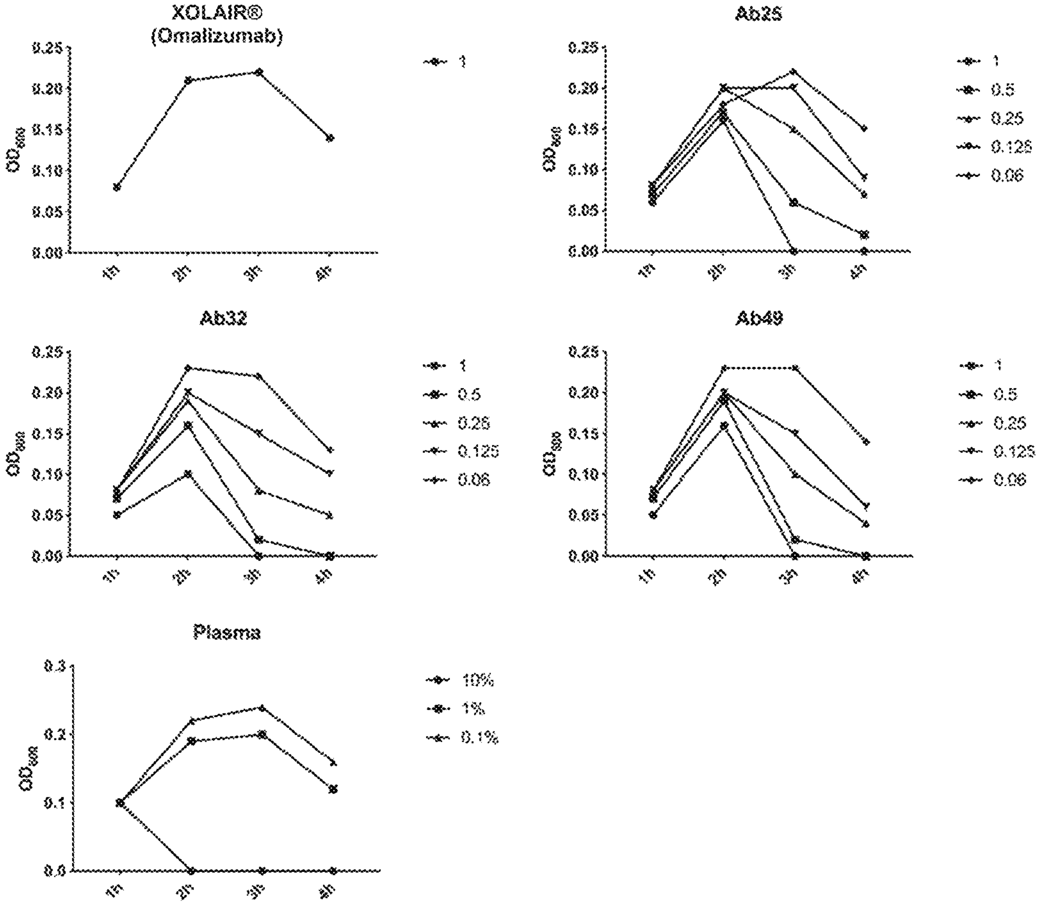
FIG. 31. Dose-dependent agglutination of both the triple antibody cocktail as well as individual antibodies.
Figure 32:
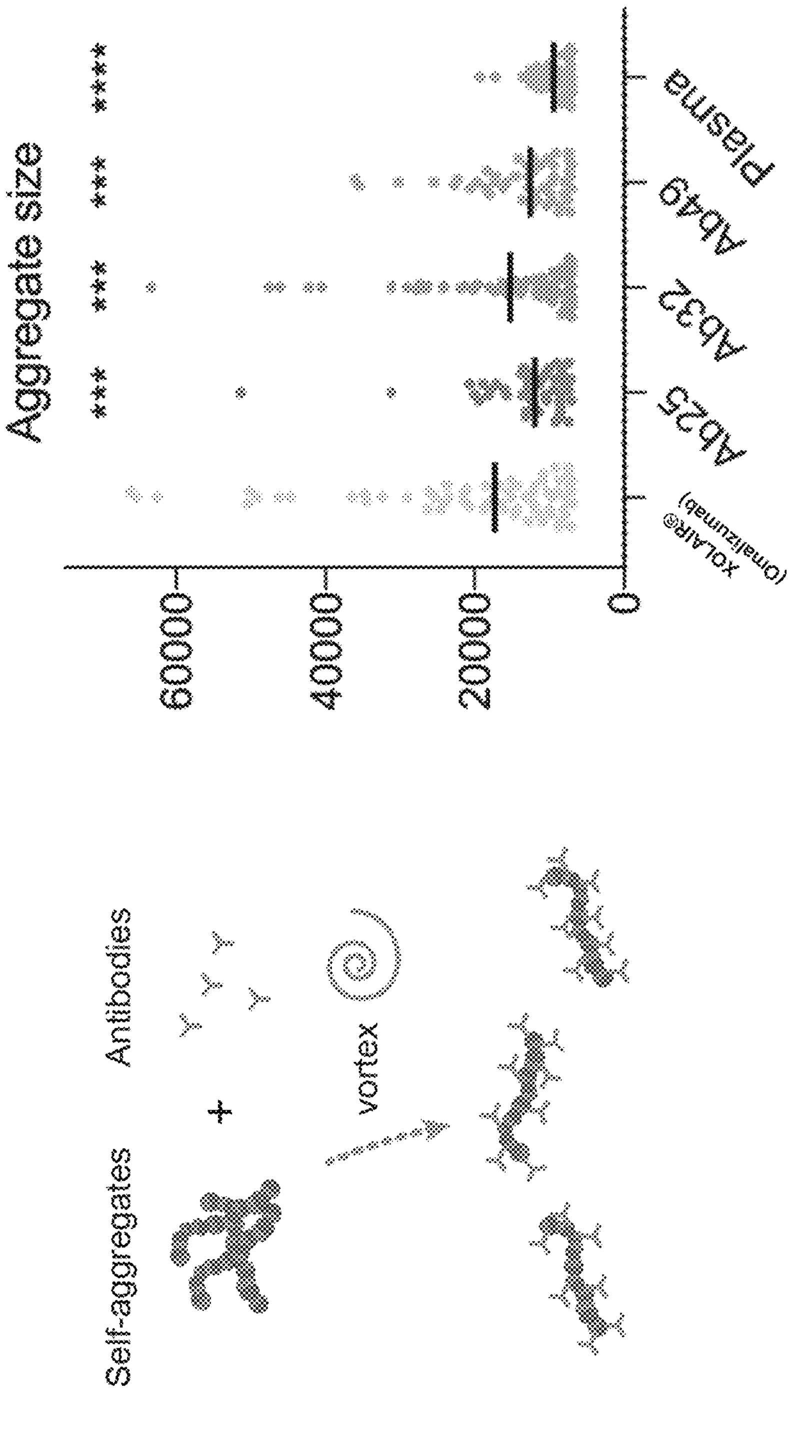
FIG. 32. Agglutinated bacteria, as well as the typical GAS aggregates, are dissipated by vigorous vortexing in the presence of the anti-M antibodies or plasma.

Antibody-mediated bacterial agglutination is a well-documented antibody function and has important biological significance such as enchaining bacteria for effective immune clearance (Moor et al. 2017; Mitsi et al. 2017). Another well-known interbacterial, GAS-specific phenomenon is the formation of M-dependent bacterial aggregates at the bottom of the growth tube (Frick et al. 2000). While it is not possible to grow GAS without having any self-aggregation, the antibodies greatly enhanced bacterial agglutination. Both the triple antibody cocktail as well as individual antibodies led to dose-dependent agglutination, as is also the case with donor serum from the patient from which the M-reactive B cells were obtained (FIG. 9, FIG. 31). This enhancement was not observed for the ΔM strain, further validating that the antibody-dependent agglutination is an M-specific phenomenon. Agglutinated bacteria, as well as the typical GAS aggregates, could be dissipated by vigourous vortexing in the presence of the anti-M antibodies or plasma (FIG. 32). GAS agglutination and aggregate dissolution were most pronounced in Ab25, 49, and to a lesser extent with Ab32, while XOLAIR® (Omalizumab) (with only IgGFc-binding) had no effect.

Figure 10:
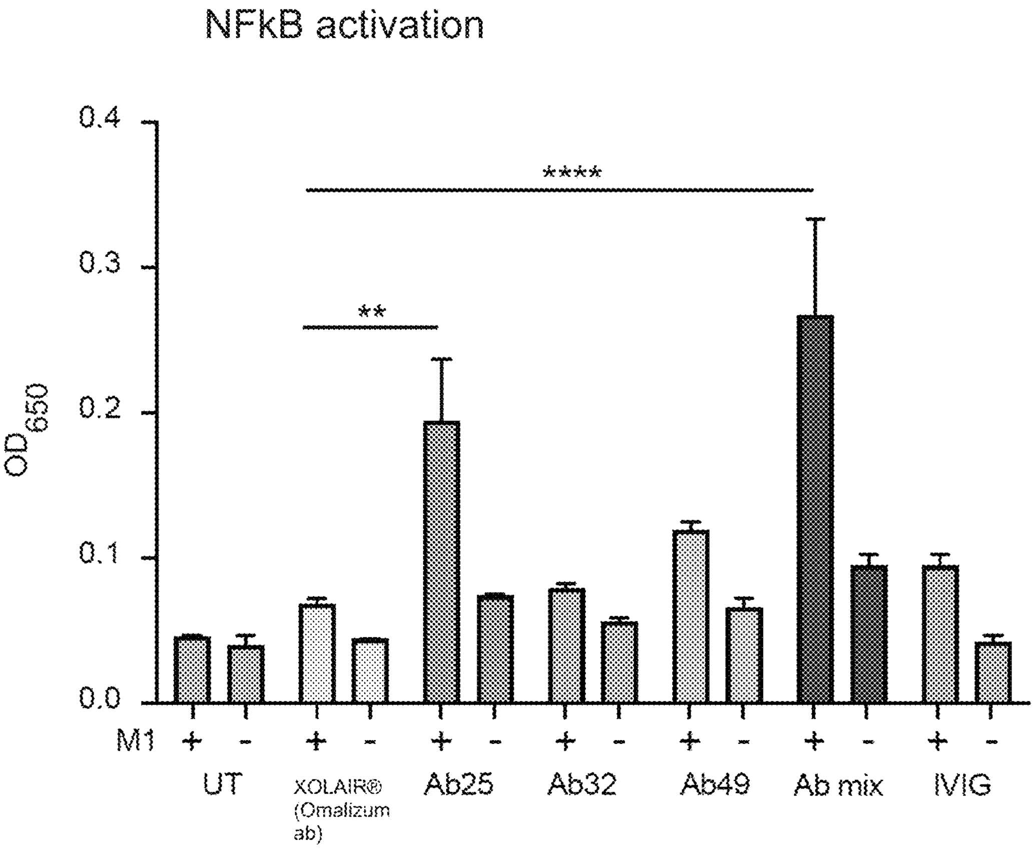
FIG. 10. THP-1-blue cells were treated with M1 protein (2 μg/ml) with or without anti-M specific antibodies. The data shown is from triplicate samples, representing experiments which were done three times. Error bars represent the SEM. Statistical significance was assessed using a one-way ANOVA with Kruskal-Wallis multiple comparison correction. * denotes p≤0.05,  for p≤0.01, * for p≤0.001 and **** for p≤0.0001.

Through ligating their antigens and mediating antigen uptake, antibodies also activate macrophages leading to proinflammatory cytokine production (Bournazos et al. 2017). We addressed the antibody-dependent M protein-induced immune activation using THP1 X-Blue reporter cells, which secrete SEAP (secreted embryonic alkaline phosphatase) as a quantitative indicator of NF-κB activation. We found that M protein alone cannot induce NF-κB signaling. However, combining M protein with Ab25 led to a significant 2.8-fold increase in NF-κB activation when compared to M protein with XOLAIR® (Omalizumab) (FIG. 10). Combining M protein with Ab49 had a modest effect on NF-κB activation (1.6-fold, ns), whereas its combination with Ab32 had no impact (1.2-fold). Combining all three antibodies led to a significant cumulative 3.9-fold increase in NF-κB activation, probably due to the combined amount of Ab25 and 49. Interestingly, we also found that IVIG does not elicit the same antibody-mediated NF-κB activation upon THP-1 exposure to the IVIG-treated M protein (1.4-fold). The combined biochemical and immunological characterization of the monoclonals shows that all are specific for M protein, bind to different epitopes, and can induce immunological effects, and that Ab25 has the most potent effect overall.

Example 3. Anti-M Antibody Promotes Efficient Phagocytosis

Figure 11:
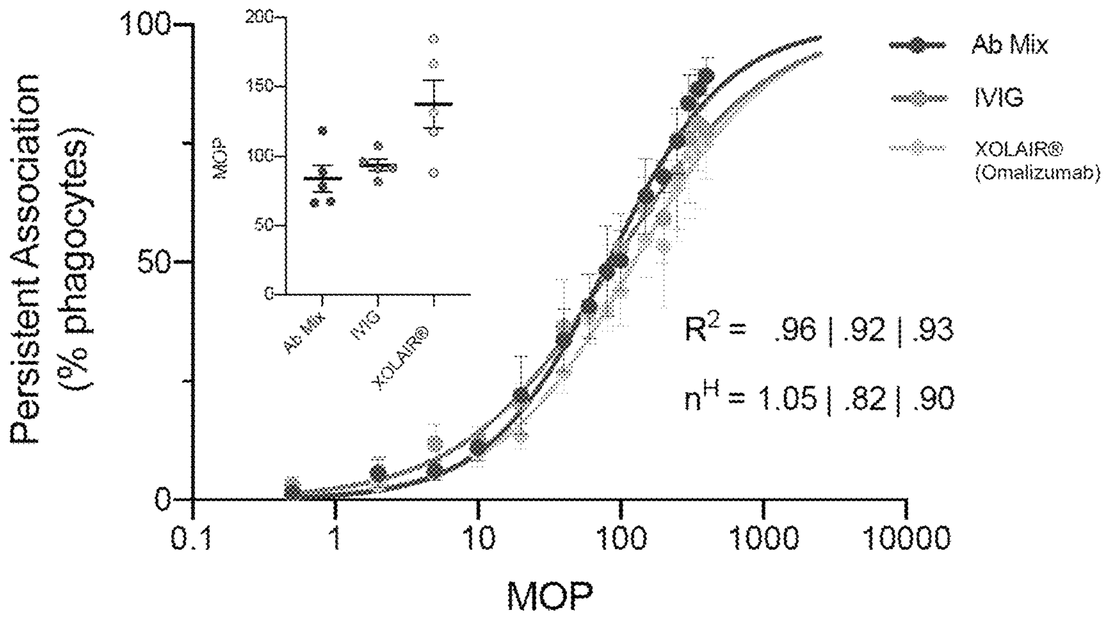
FIG. 11. Curves representing the percentage of cells that were associated with bacteria as a function of the MOP. The inset displays the $MOP_{50}$ for each opsonization condition. THP-1 cells were incubated with increasing MOPs of heat killed SF370 bacteria The THP-1 cells were allowed to associate with and internalize the bacteria for 30 minutes before flow cytometric analysis.
Figure 12:
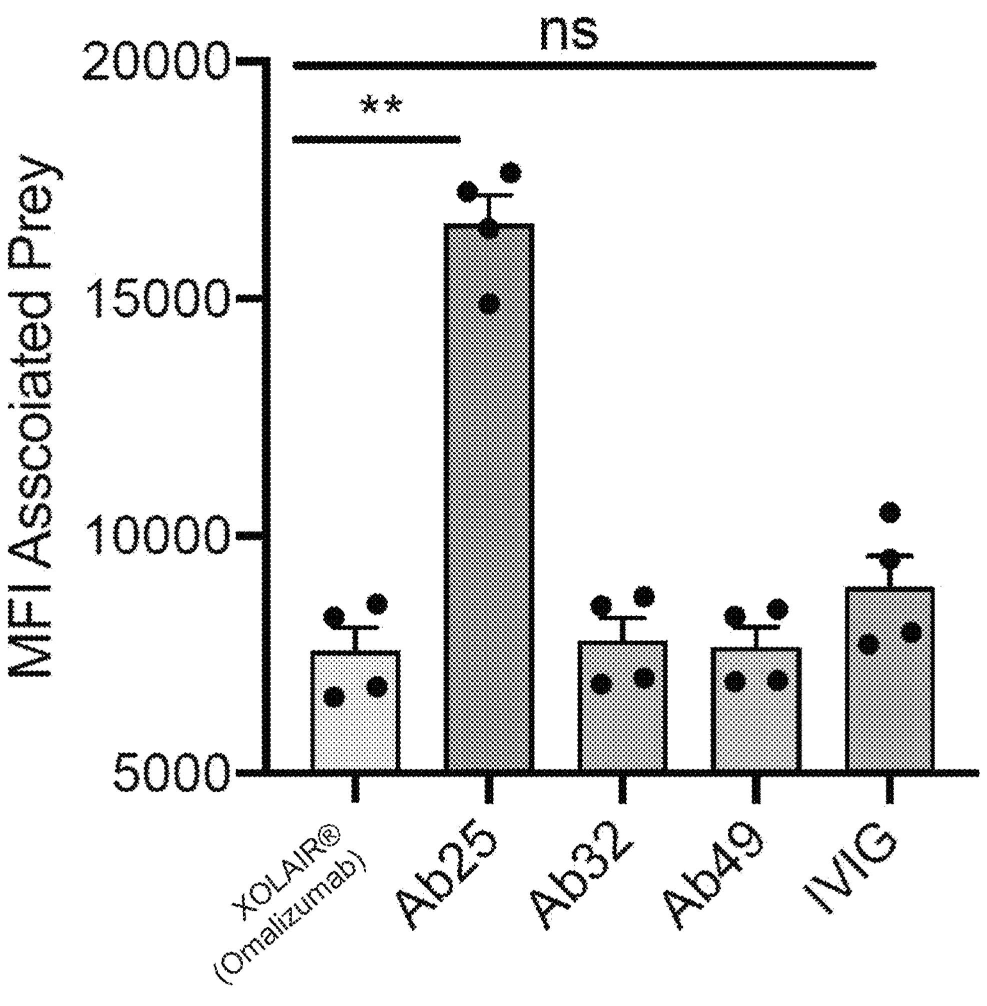
FIG. 12. The MFI of THP1 cells in the FITC channel indicates the effect of each antibody on bacteria association to THP1 cells at MOP 400.
Figure 13:
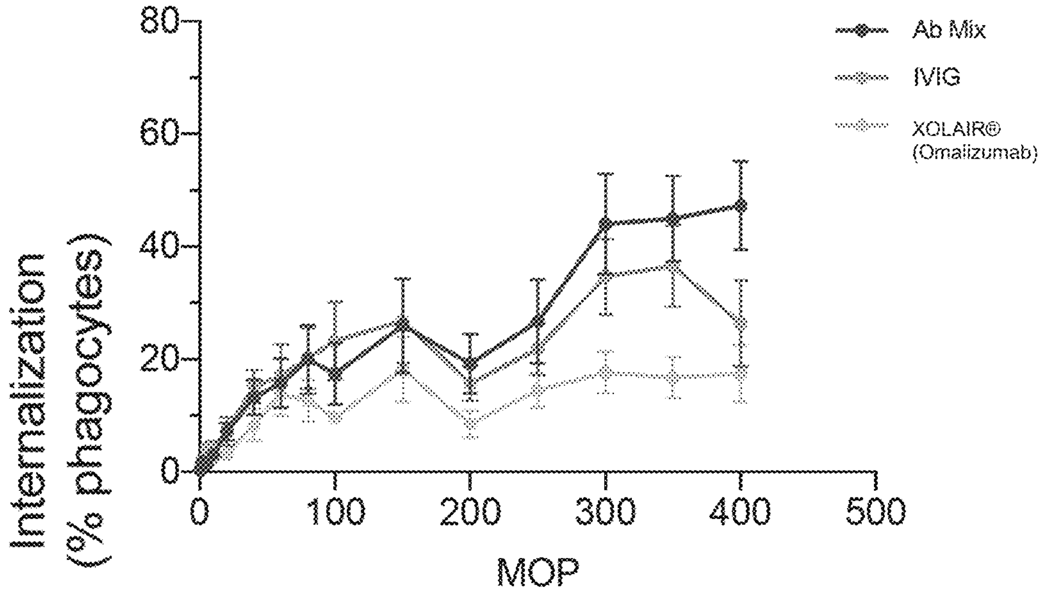
FIG. 13. The percentage of cells with internalized bacteria plotted for each MOP.
Figure 14:
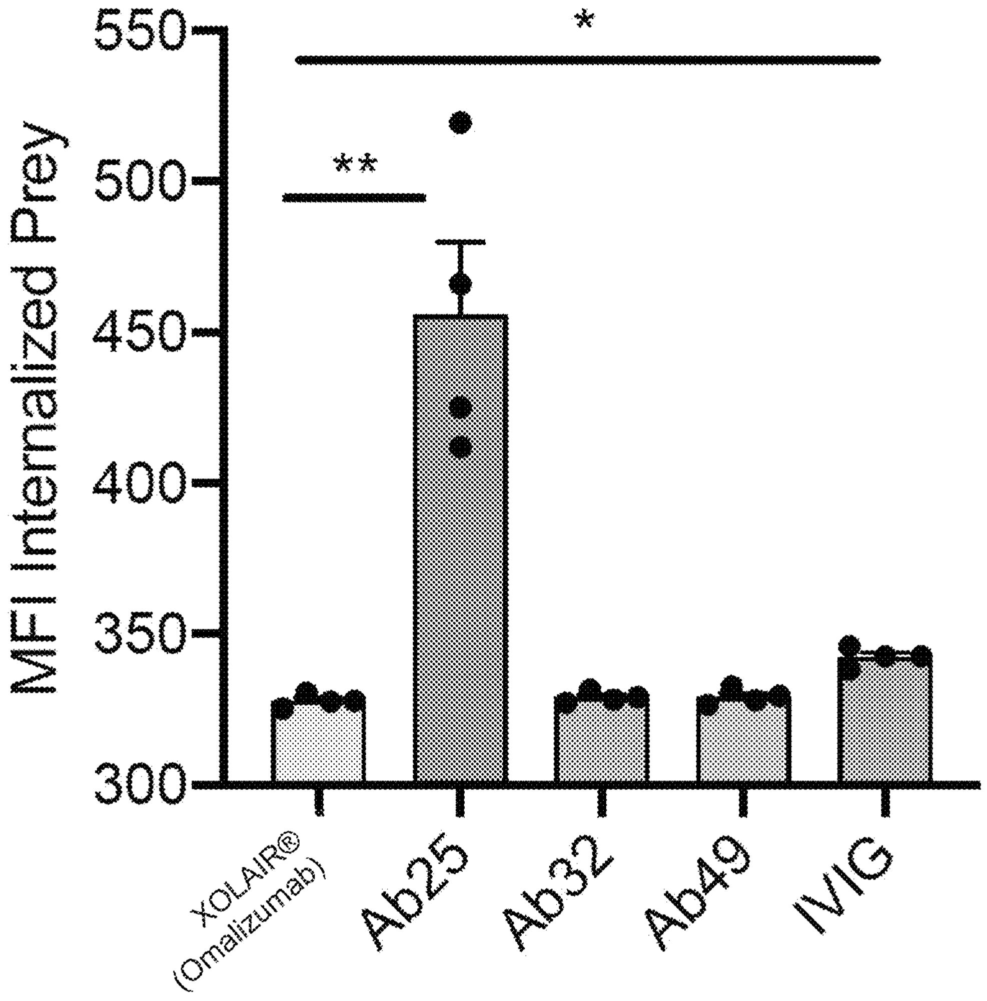
FIG. 14. MFI of THP1 cells which had internalized bacteria pre-opsonized with 10 μg/ml individual antibodies are presented at an MOP of 400 (internalized bacteria channel).
Figure 15:
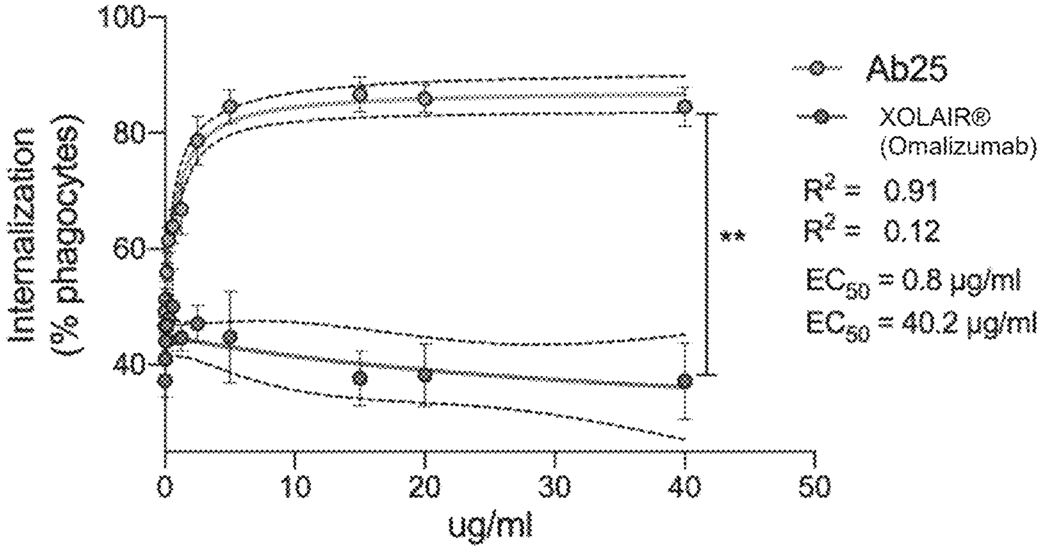
FIG. 15. Heat killed SF370 opsonized with Ab25 (upper symbols in graph) or XOLAIR® (Omalizumab) (lower symbols in graph) at a range of concentrations (0.017-40 μg/ml) were incubated with THP1 cells at MOP 150. Data shown in this figure is from the pooled results of three independent experiments. Error bars represent the SEM. Statistical significance was assessed using one-way ANOVA with Kruskal-Wallis multiple comparison correction and * denotes p≤0.05,  for p≤0.01, * for p≤0.001 and **** for p≤0.0001.
Figure 33A:
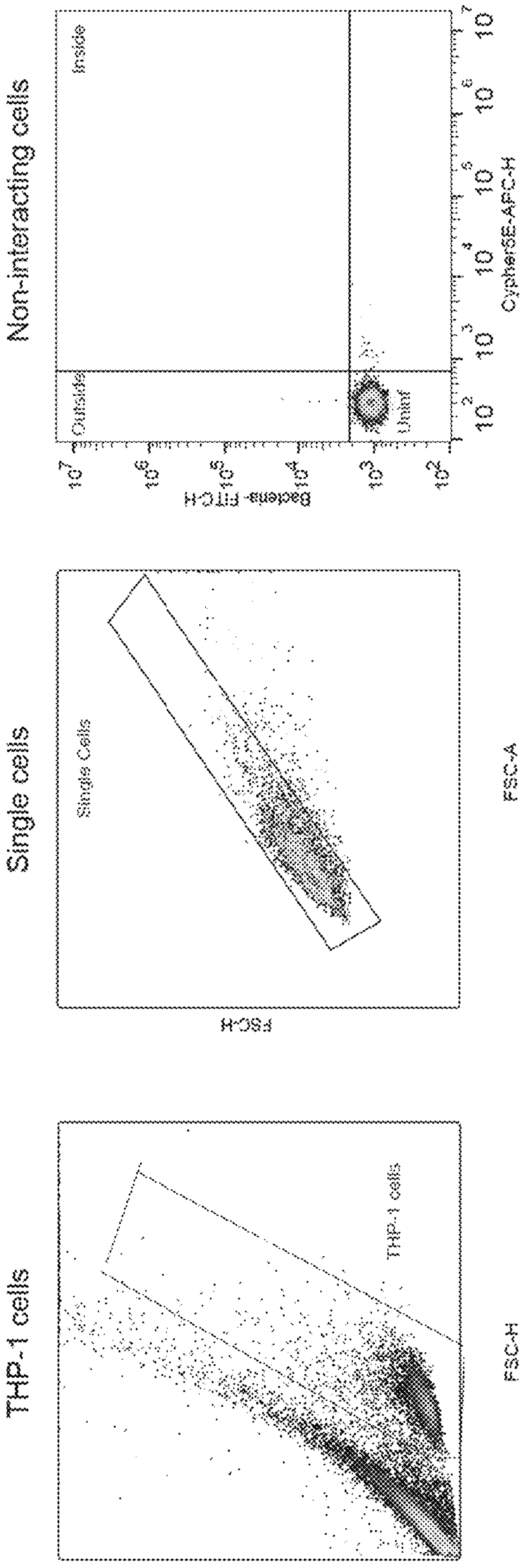
FIG. 33A-B. Incubation of phagocytic THP-1 cells with pH-sensitive CypHer5-stained bacteria at increasing multiplicities of prey (MOP). We combined Ab25, 32, and 49 to assess their cumulative effect on bacterial association with THP-1 cells. THP-1 cells were gated based on FSC and SCC. Single cells were selected based on FSC-area and height parameters. Non-interacting cells have no FITC (bacteria) or CypHer5E (internalized bacteria) signal. Interacting cells associated with bacteria show a shift to the upper left quadrant (outside) whereas THP-1 cells with internalized bacteria shift to the upper right quadrant due to acquisition of the APC signal. THP-1 cells inoculated with bacteria were kept on ice to reduce the phagocytosis. This is visible as a reduction in the number of events in the upper right quadrant.
Figure 33B:
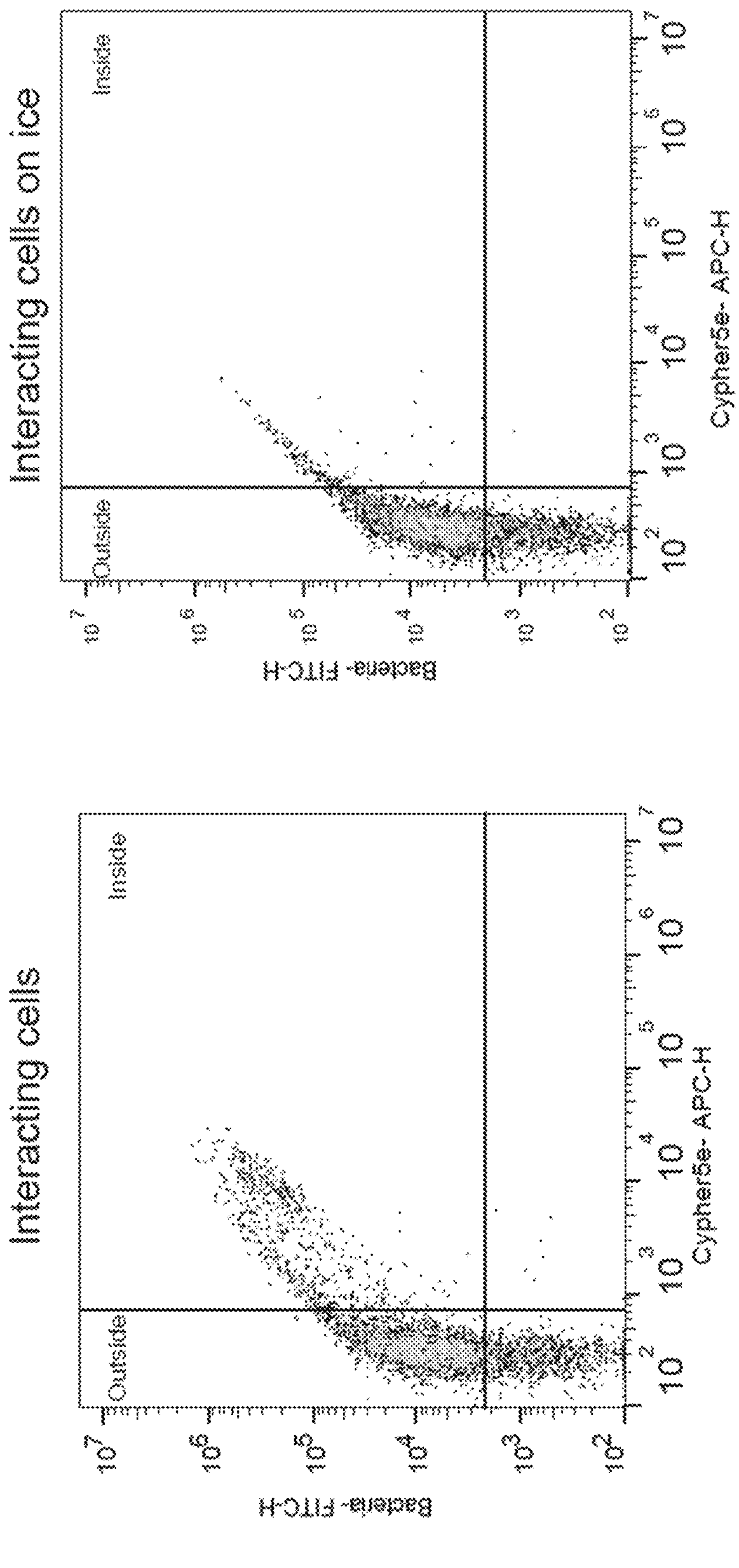
Figure 34:
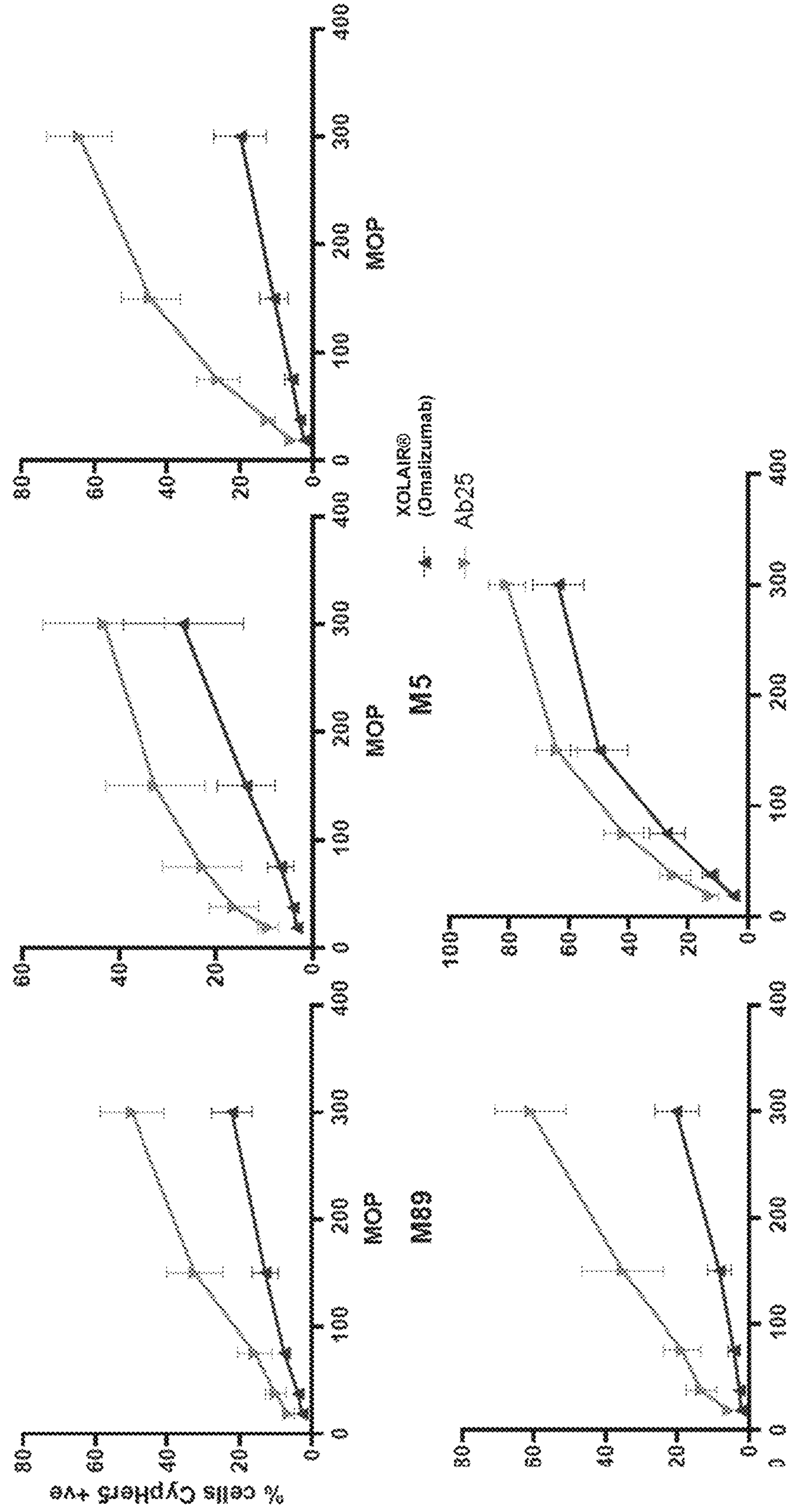
FIG. 34. Phagocytic enhancement by Ab25. 10 μg/ml of XOLAIR® (Omalizumab) or Ab25 were used to study phagocytic enhancement across different M serotypes. GAS with serotypes M1 (AP1), M12, M89 and M5 were compared in addition to the M1 SF370 strain. The effect of the antibody treatment on internalization rate was measured by flow cytometry. The error bars represent the standard error of the mean (SEM). The data are from three independent experiments.

Phagocytosis is a receptor-mediated process where prey are internalized into phagosomes, followed by their maturation into acidic, hostile compartments. To investigate the ability of the antibodies to trigger phagocytosis, we used persistent association-based normalization (de Neergaard et al. 2019) to study both the antibodies' ability to increase phagocyte association as well as internalization. We incubated phagocytic THP-1 cells with pH-sensitive CypHer5-stained bacteria (FIG. 33-34) at increasing multiplicities of prey (MOP). We combined Ab25, 32, and 49 to assess their cumulative effect on bacterial association with THP-1 cells. Compared to XOLAIR® (Omalizumab), the antibody mix and, to a lesser extent, IVIG modestly increased the association of the bacteria with THP-1 cells (FIG. 11). This can be seen as a left shift in the curve, meaning that fewer bacteria are required to achieve maximal association. When tested individually, only Ab25 showed association enhancement, indicating that the antibody mix-mediated increase in association is solely due to Ab25 (FIG. 12). The antibody mix increased internalization when compared to XOLAIR® (Omalizumab), and the divergence between the two treatments was increased as a function of MOP (FIG. 13). Upon a more detailed examination of individual antibodies, only Ab25 showed an increase in internalization (FIG. 14). Dose-response analysis showed that Ab25 is significantly more effective than XOLAIR® (Omalizumab) in mediating internalization (concentration at which 50% of THP-1 cells have internalized bacteria; $EC_{50}$ 0.8 vs. 40.2 μg/ml) (FIG. 15). The phagocytosis data showed that despite strong Fab-mediated binding and induction of other immunological effects by all monoclonals, only one antibody, Ab25, can promote phagocytosis of group A streptococci.

Example 4. Anti-M Antibody Protects Mice from GAS Infection

Figure 16:
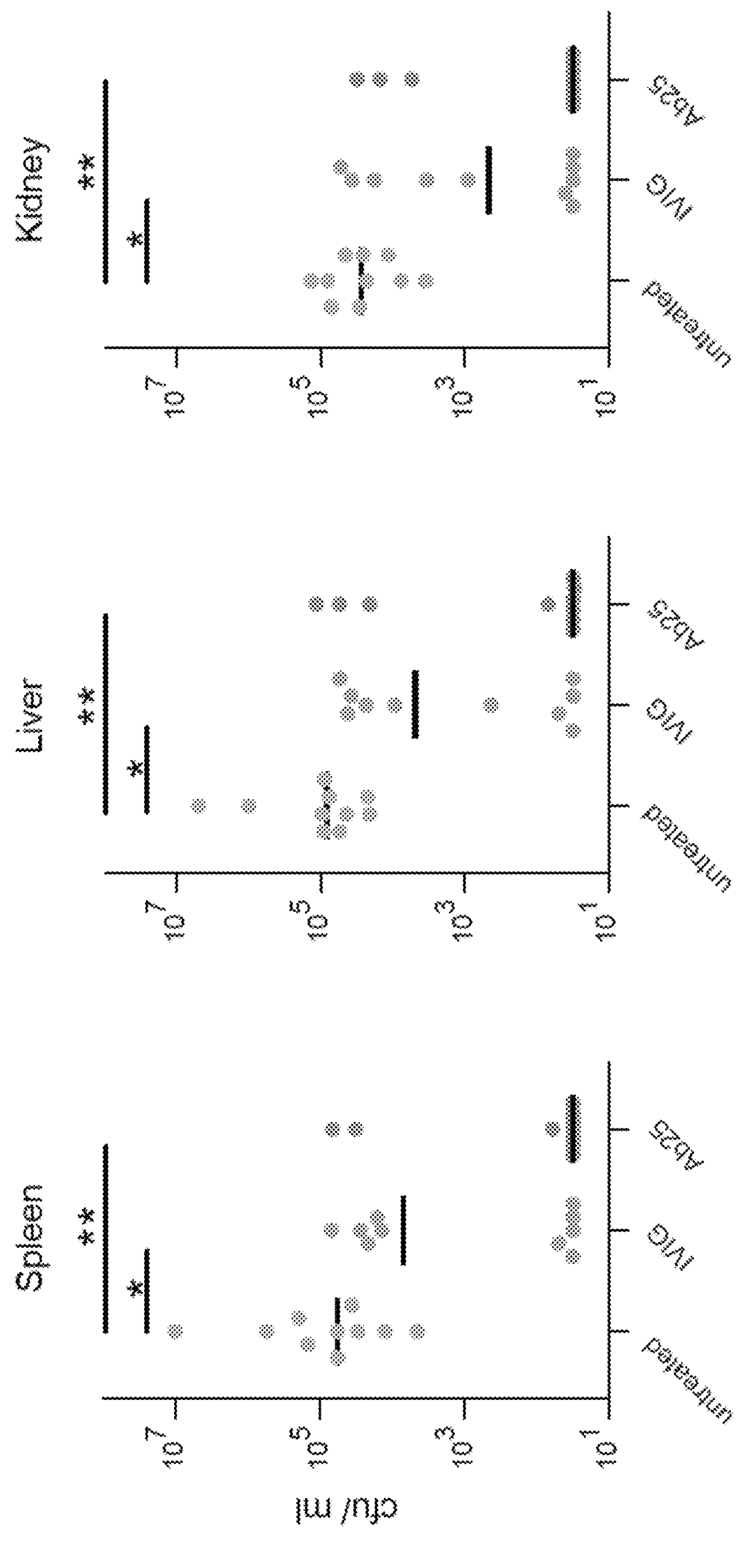
FIG. 16 shows the bacterial burden in spleen, kidney and liver tissue was measured by colony counts.
Figure 17:
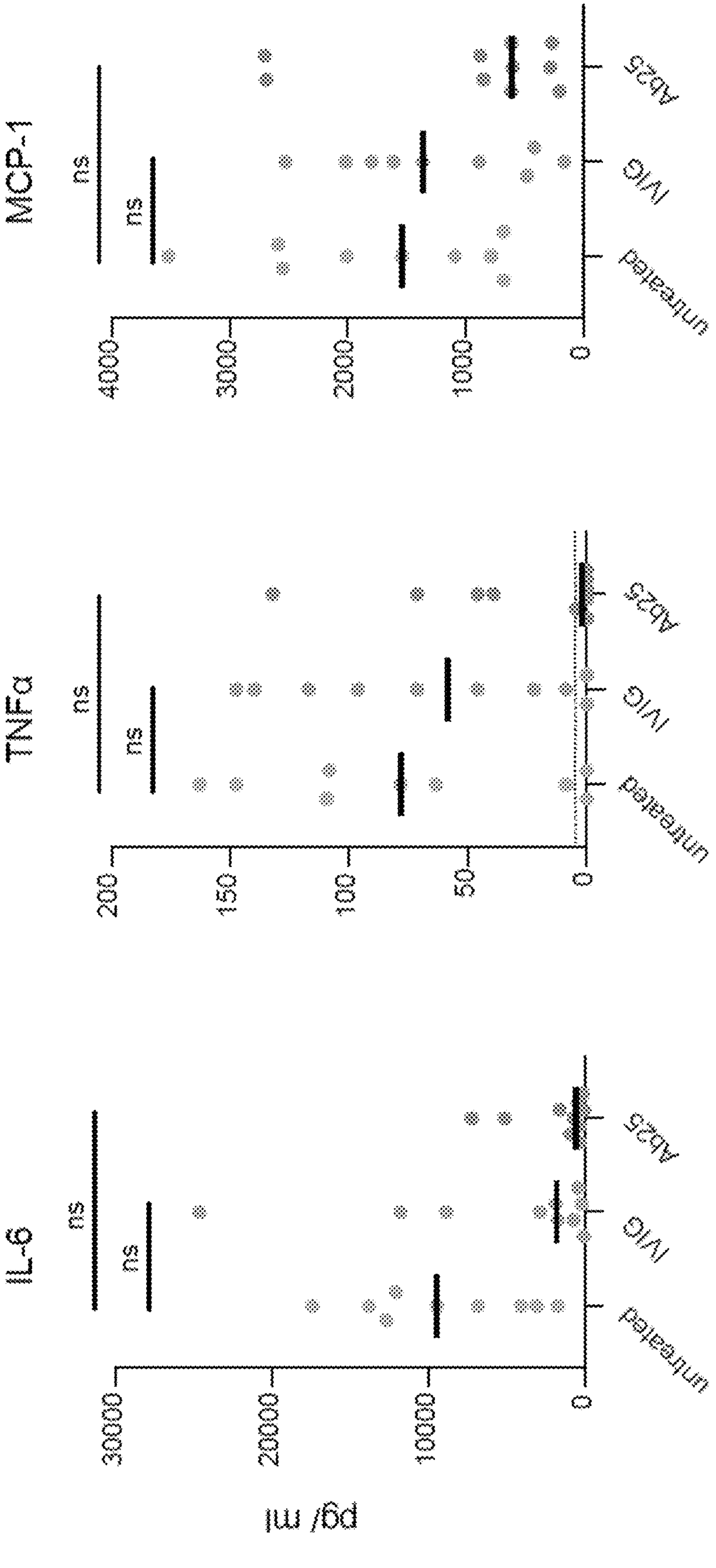
FIG. 17. Cytokine levels in plasma was assessed using a cytometric bead array. The data is pooled from two independent experiments (5 mice per condition, per set).

The induction of phagocytosis and NF-κB, as seen with Ab25, are important indicators of immune function. To test the potential protective effects of Ab25 in vivo, we used a mouse model of subcutaneous infection with GAS. The mice were pretreated with intraperitoneal injections of Ab25 or IVIG. High-dose IVIG have been used in mice models of severe GAS infections (Sriskandan et al. 2006) and served as a positive control. Treatment with IVIG or Ab25 reduced the bacterial burden in the spleen, kidney, and liver when compared to untreated controls, with Ab25 exhibiting better protection than IVIG (FIG. 16). Ab25 or IVIG treatment also affected the cytokine mobilization as seen by a reduction of TNFα, MCP-1, and IL-6 levels in plasma (FIG. 17). The levels of IFNγ, IL-10 and IL-12p70 were below the level of detection under our experimental conditions. Taken together, the agglutination, NF-kB, phagocytosis, and animal experiments show that Ab25 has an immunomodulatory effect, which protects an animal from GAS infection.

Figure 19:
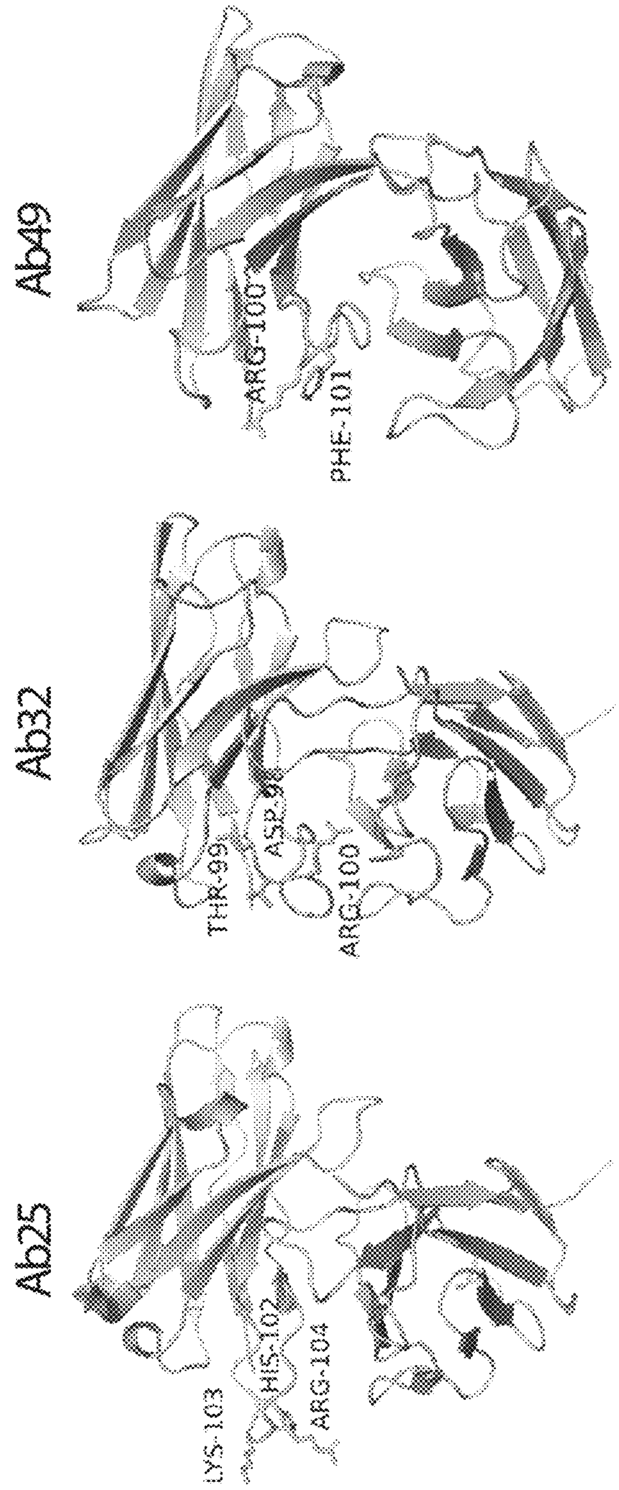
FIG. 19. Representations of the Fab fragments of the modelled antibodies Ab25, Ab32 and Ab49 are shown in FIG. 19. In each antibody, the CDR H3 and L3 loops are indicated (Ab25, to the left; Ab32, middle; and Ab45, to the right).
Figure 20:
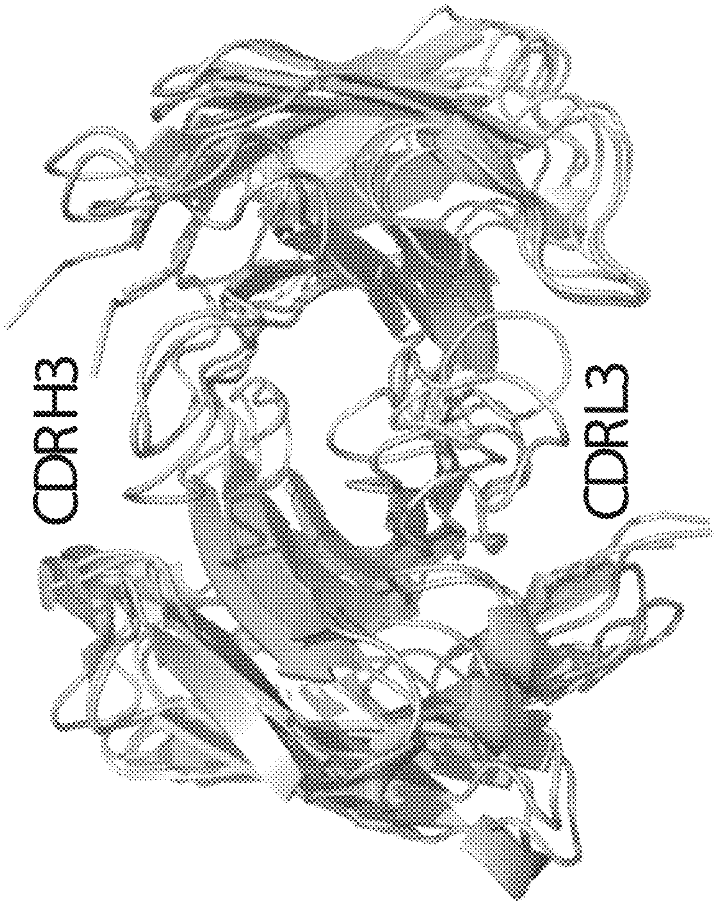
FIG. 20. Structural alignment of Ab25, Ab32 and Ab49 are shown in FIG. 20.

Example 5. Antibodies Target a Similar Region in M Protein Through Single Fab or Dual-Fab Binding Antibodies that bind via their Fabs with high affinity are typically expected to promote an immune response. However, of the tested anti-M antibodies, only Ab25 can promote all tested immune effector functions. To assess structural differences between the antibodies, we present Rosetta-generated molecular models of the Fab fragments of Ab25, Ab32, and Ab49 in which we highlight the complementarity-determining region (CDR) domains (FIG. 18). In order to compare the conformations in the CDR H3 and L3 loop regions, we analyzed the Fab fragments of all three antibodies (FIG. 19). The similarity between Ab25 to Ab49 is apparent over the CDR H3 loop (RMSD 1.OA), whereas the conformation of Ab32 CDR H3 is different (FIG. 20). The conservation at the primary amino acid sequence level of Ab25 and Ab49 is less evident.

Figure 21:
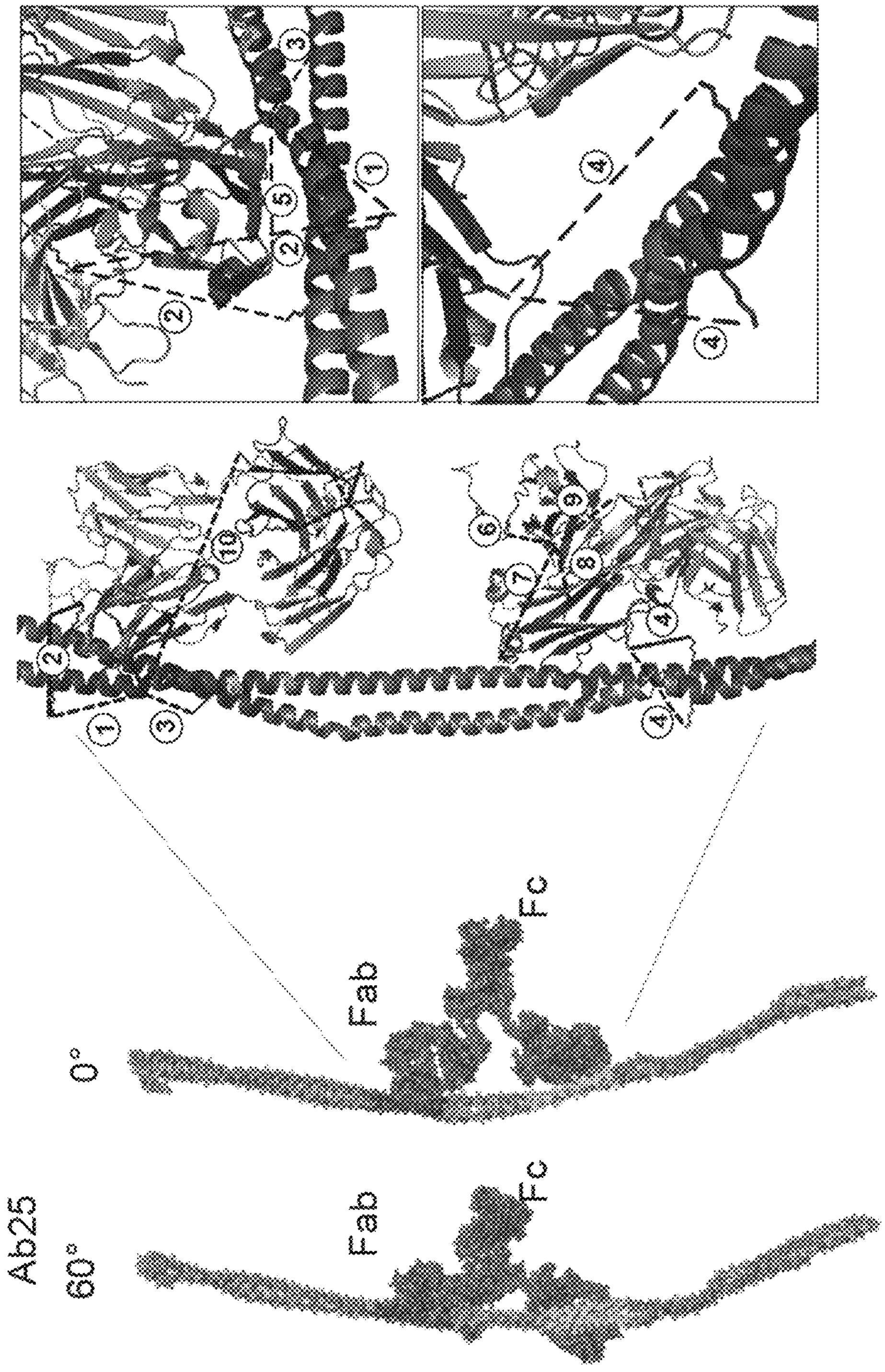
FIG. 21. The M1 interaction sites of Ab25 is shown in FIG. 21. A rotation of 60° along the y-axis has been applied between the views. The length of contact surface is 45 Å in the upper binding site (B2-B3-domain) and 18 Å in the lower (C-domain).
Figure 22:
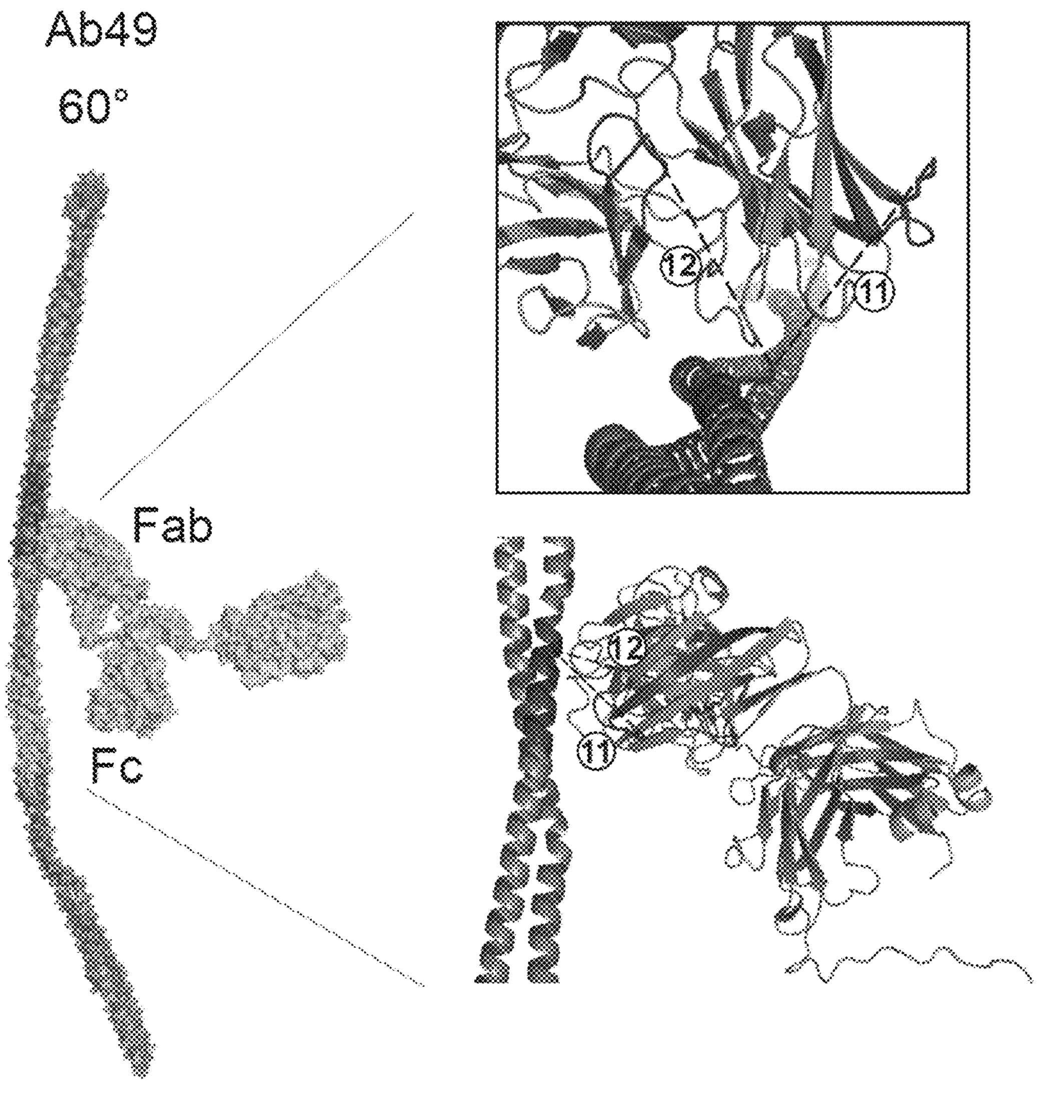
FIG. 22. Presentation of the M1 interaction site of Ab49. The length of contact for Ab49 (B2-B3 domain) is approximately 16 Å. Insets in FIGS. 21 and 22 represent a full-length model generated by TX-MS (Hauri et al. 2019) showing the Fab-mediated interaction of Ab25 or Ab49 (heavy chain in dark shade, light chain in a lighter shade) with the M1 protein (in gray). Crosslinked peptides are indicated in dark gray shade, and crosslinks between lysine (K) residues as dashed black lines. The CDR H3 loop is shown in light gray shade (for Ab25) or in gray (for Ab49). There are two interaction sites for Ab25 on the M1 protein, the upper one in the B2-B3-domain (inset) supported by 4 crosslinks and the lower one in the C1-domain (inset) by 6 crosslinks. Only one interaction site for Ab49 with M1 exists, and it is supported by 2 crosslinks.
Figure 35:
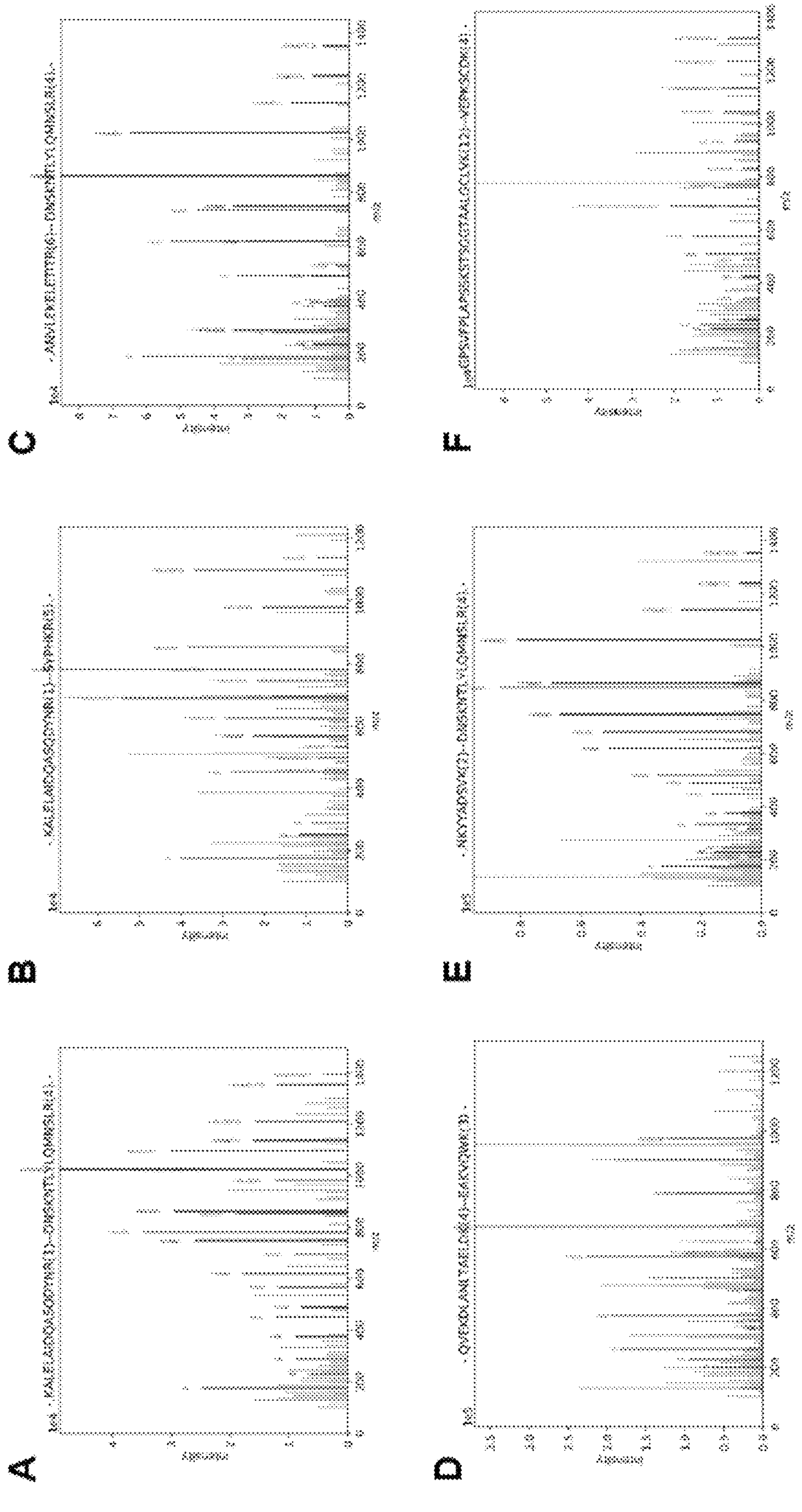
FIG. 35. M/S data for identification of cross-linked peptides between the antibodies and M1-protein (panel A-F).
Figure 36:
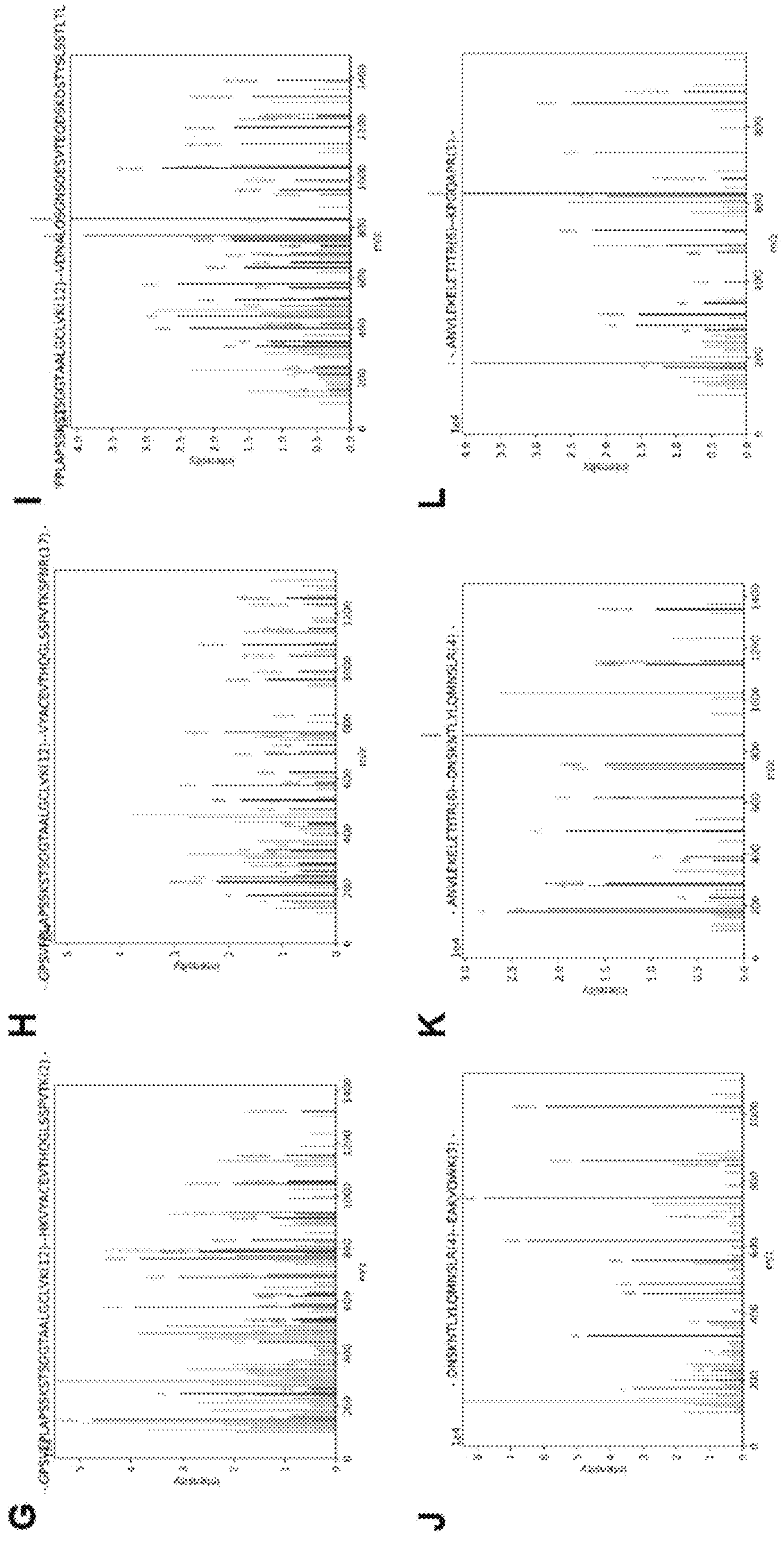
FIG. 36. M/S data for identification of cross-linked peptides between the antibodies and M1-protein (panel G-L).
Figure 37:
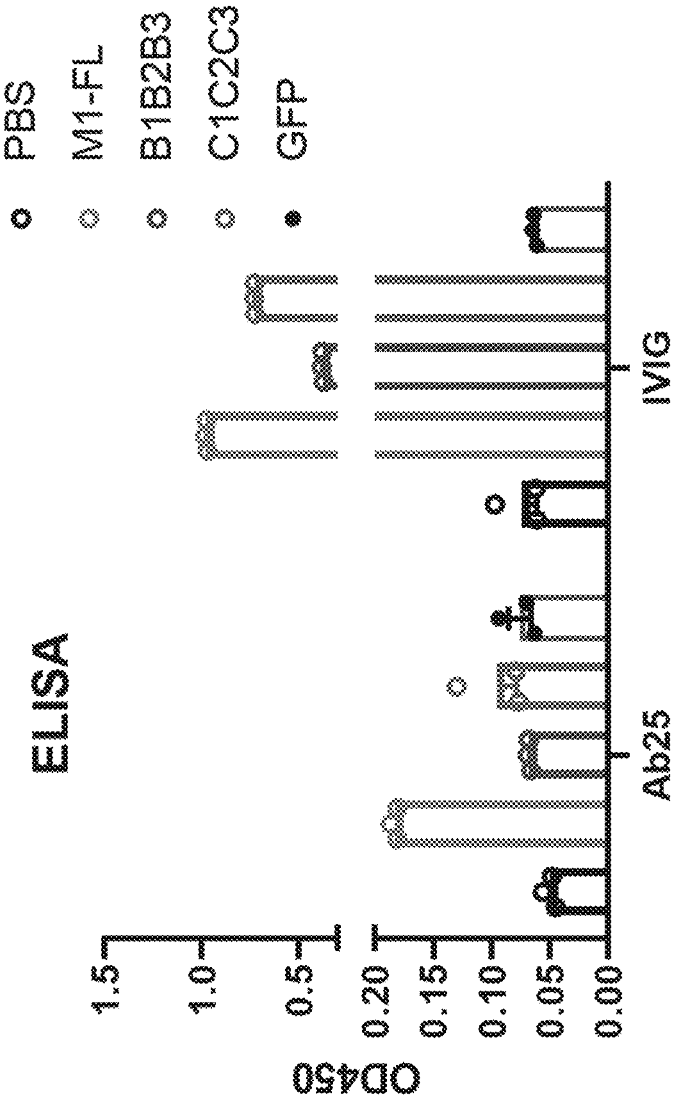
FIG. 37. ELISA reactivity of Ab25 (30 μg/ml) or IVIG (1 mg/ml) against fragments spanning the B1B2B3 as well as the C1C2C3 regions of the M protein. The full length M1 and GFP serve as positive and negative controls, respectively. Three independent experiments with SD shown.

To determine the epitopes recognized by the respective F(ab')2-fragments on the M1 protein, we performed targeted in solution cross-linking coupled to mass spectrometry (TX-MS) (Hauri et al. 2019). TX-MS can model accurate quaternary conformations of large protein complexes and support these conformations via identifying several independent cross-links based on many high-accuracy cross-linked peptide fragments. Of the three antibodies analyzed, we identified ten cross-linked peptides between Ab25 and M1-protein. These cross-links are found between the $F(ab')_2$ and two different regions on the M-protein, indicating that Ab25 has two different binding-sites in the B-S-C domain region (FIG. 21, FIG. 35). As part of the TX-MS protocol a large number of protein-protein docking models are created. Superimposing the cross-linked distant constraints onto these docking models, shows that Ab25 F(ab')s can simultaneously bind the two crosslinked epitopes without inducing large conformational changes in the hinge region. This implies that Ab25 is capable of dual-Fab binding in an intramolecular cis-binding fashion. Antibody cis-binding is different from the traditional intermolecular trans-binding interaction that can induce avidity when antigens are in close proximity (Klein and Bjorkman 2010). A similar binding-site in the M1 protein B-S-domain region is also identified for Ab49, for which we identified two cross-linked peptides to the M1-protein (FIG. 22, FIG. 35). Intriguingly, the M1 protein S-region has previously only been associated with Fc-mediated binding (Nordenfelt et al. 2012; Akesson et al. 1994).

Figure 23:
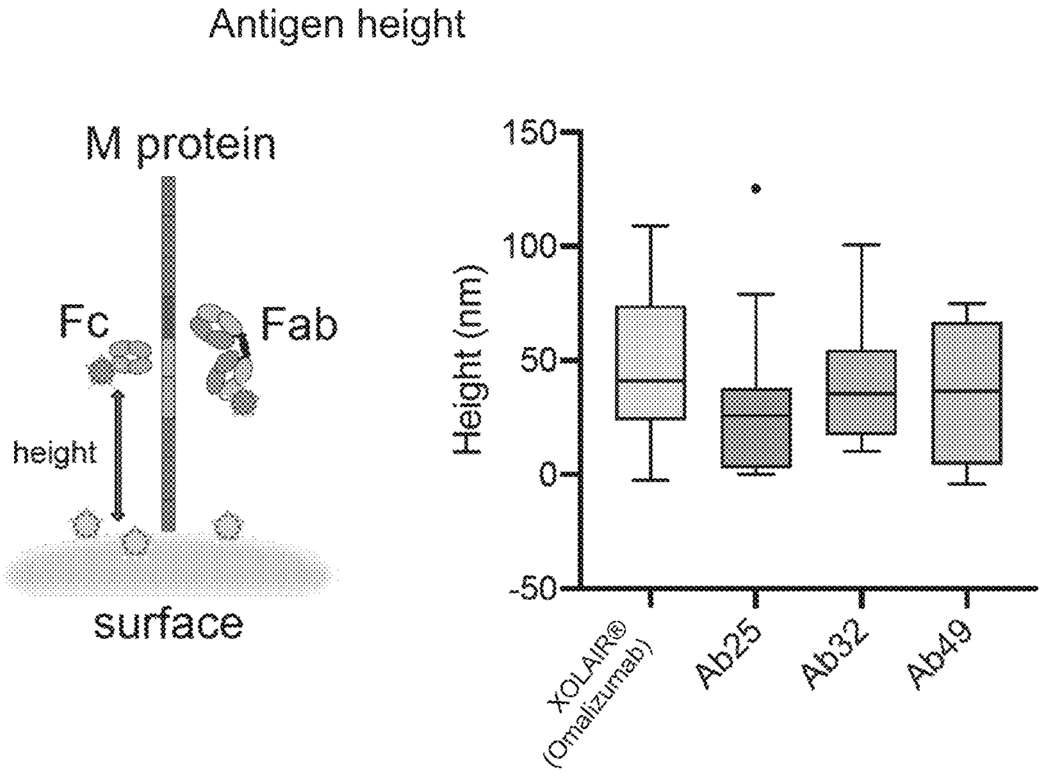
FIG. 23. The Fab epitopes as well as the Fc-binding region on the M protein are estimated by a fluorescence localization averaging method using structured illumination microscopy (SIM) images (Kumra Ahnlide et al manuscript 2020). A relative binding site is determined by resolving the distance between the antibody and a reference channel (WGA) using the cumulative signals from many images. The results are from 4 independent experiments with N=9, 13, 9, 9, respectively.
Figure 24:
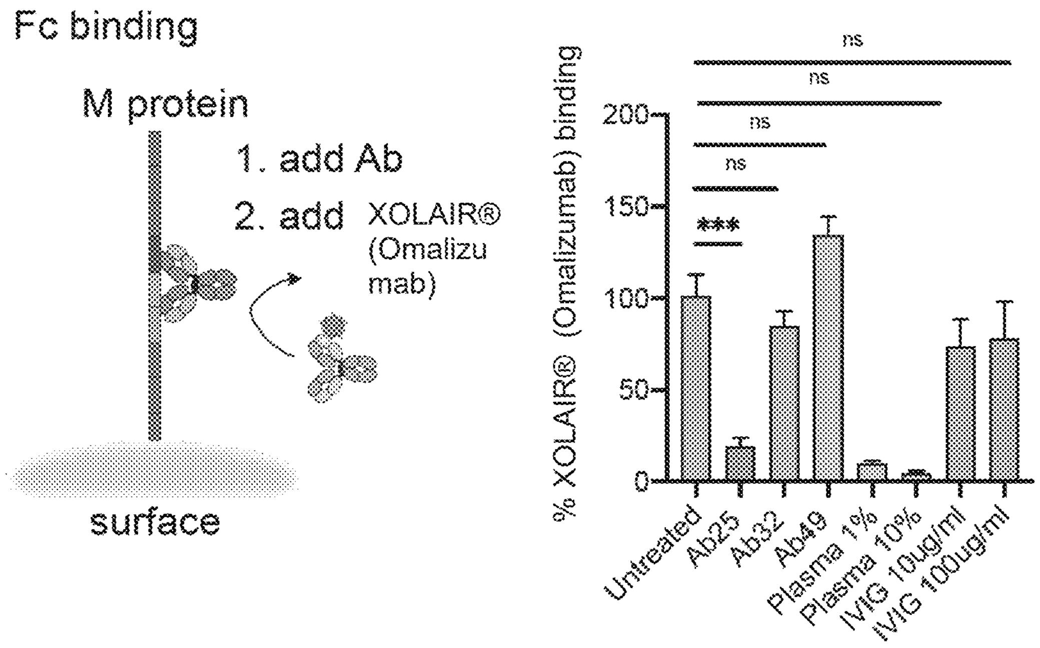
FIG. 24 shows data from the binding of Alexa647-conjugated XOLAIR® (Omalizumab) (100 μg/ml) to SF370 after pre-treatment with indicated antibody samples (10 μg/ml). The data is from 3 independent experiments pooled together. Statistical significance was assessed using one-way ANOVA with Kruskal-Wallis multiple comparison correction and * denotes p≤0.05,  for p≤0.01, * for p≤0.001 and **** for p≤0.0001.

To validate the observed binding sites through an orthogonal approach, we used site-localization microscopy, where the relative distance between fluorescently labeled cell wall and antibody binding sites is determined by repeated measures of multiple individual bacteria (FIG. 23). The height analysis showed that all monoclonal F(ab')2 fragments bind close to the Fc binding domain (S) on the M1 protein (compared to XOLAIR® (Omalizumab) Fc binding), which supports the TX-MS results. Since the antibodies appear to have epitopes close to the Fc binding domain (as seen in FIG. 21-22), we further investigated if any of the antibodies could interfere with Fc binding. If the observed dual-Fab cis binding of Ab25 is valid, Ab25 would cover the S domain (FIG. 5D) and would be able to block Fc binding, whereas single Fab interactions would have a smaller or no interference with Fc-binding. We measured the binding of fluorescent XOLAIR® (Omalizumab) to SF370 that had been preincubated with antibody samples. Ab25 significantly obstructed Fc-binding, whereas Ab32 and Ab49 did not. Since Ab49 and Ab25 share one similar epitope, located above the S region, it indicates that binding there alone is not sufficient to break the Fc interaction, and strongly suggests that this is due to a dual-Fab cis binding capacity of Ab25.

Figure 25:
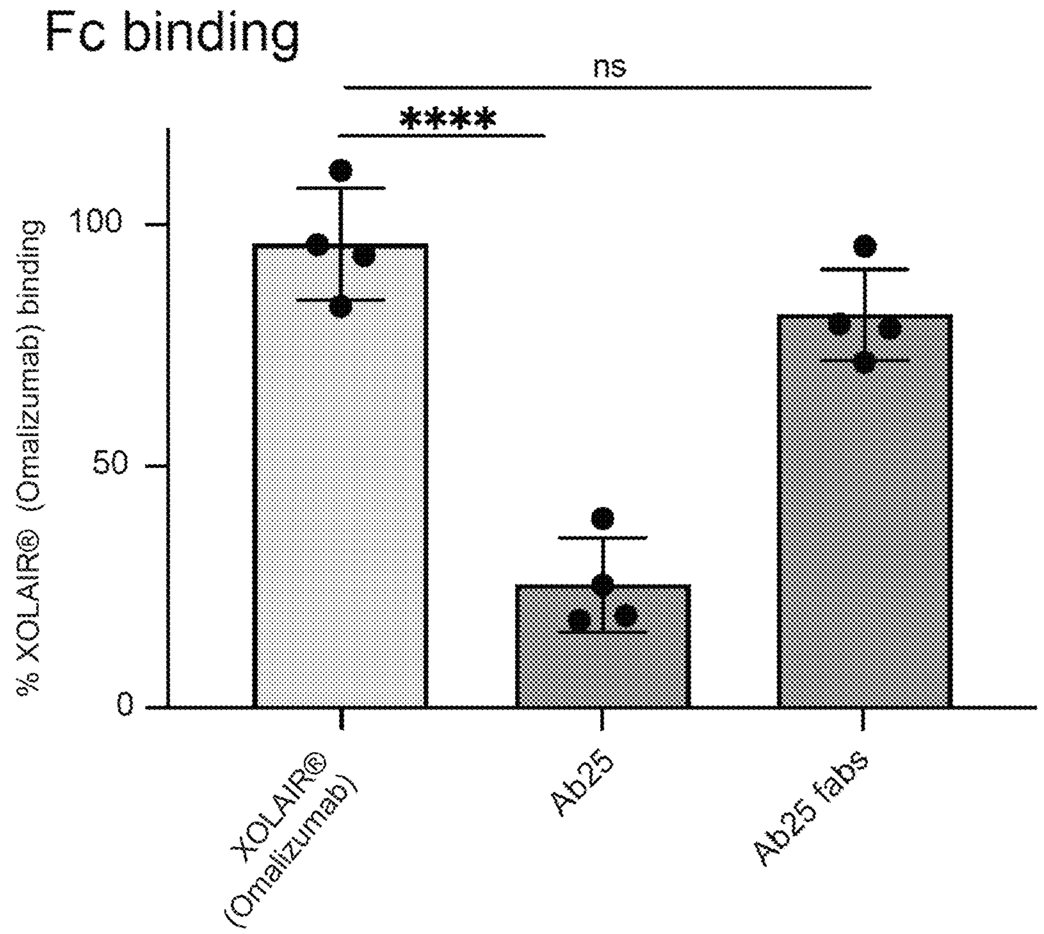
FIG. 25 shows results from XOLAIR® (Omalizumab) binding to bacteria via its Fc binding. Heat killed bacteria previously stained with Oregon Green were incubated with 10 μg/ml of Ab25 or IgdE-digested (Spoerry et al. 2016) Ab25 (Fabs). The bacteria were then incubated with fluorescently labelled XOLAIR® (Omalizumab) (AF647) before being analyzed with flow cytometry. Bacteria which bound XOLAIR® (Omalizumab) via its Fc binding are shown as positive.
Figure 26:
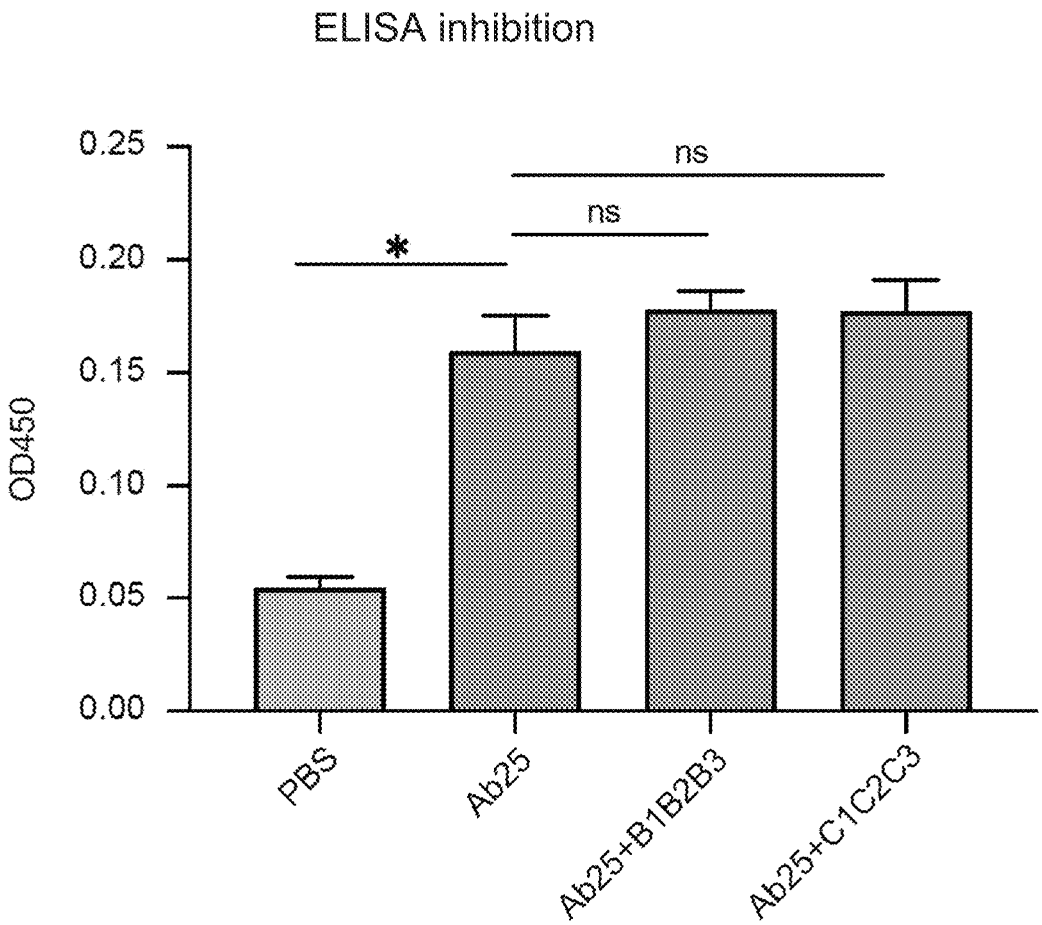
FIG. 26 shows results from a competition anti-M protein ELISA which was performed where free M1 fragments were mixed with Ab25 at equimolar ratios (10 μg/ml). The wells were then washed, and the signal developed using Protein G-HRP.
Figure 27:
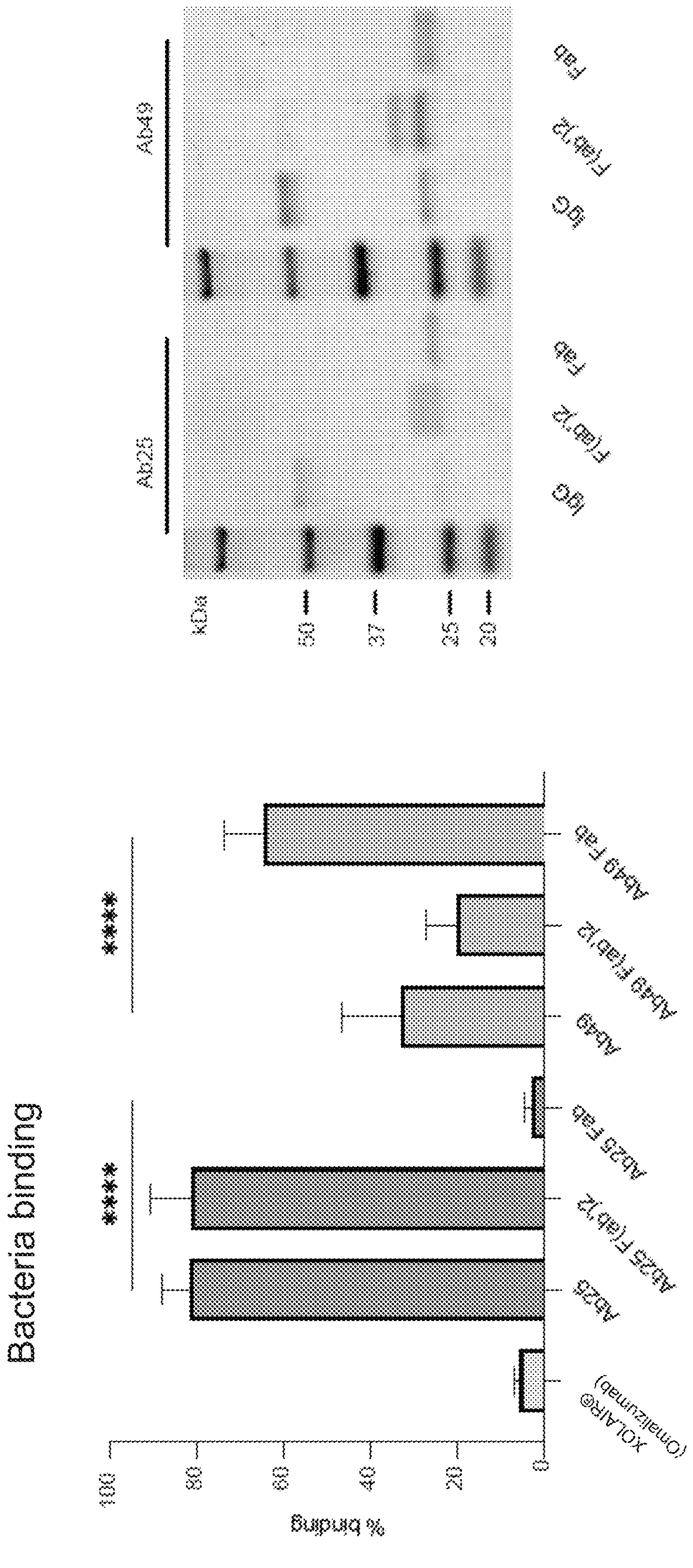
FIG. 27 shows results from experiment on binding properties of XOLAIR® (Omalizumab), IdeS-cleaved or IgdE-cleaved Ab25 or Ab49 as studied by mixing the antibodies with heat killed, Oregon Green bacteria which were then washed and stained with Alexafluor 647-conjugated Fab anti-Fabs and analyzed by flow cytometry. The panel to the right shows SDS-PAGE analysis of the antibodies used in the binding analysis.
Figure 28:
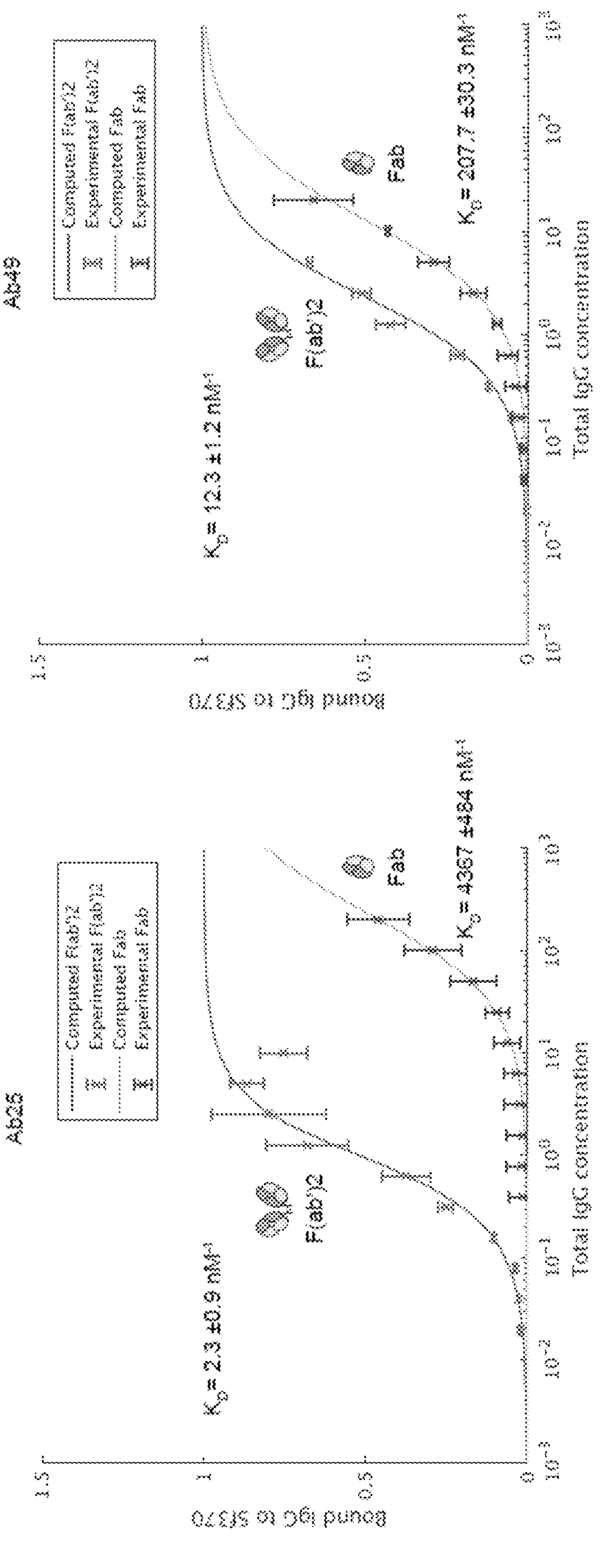
FIG. 28 shows affinities for Fabs generated by IgdE treatment of Ab25 and Ab49 that were performed as described in Example 1 (FIGS. 1-5). The new Fab data is overlaid on the data from FIG. 5. The data represents pooled results from four independent experiments. Statistical significance was assessed using one-way ANOVA with Kruskal-Wallis multiple comparison correction and * denotes p≤0.05,  for p≤0.01, * for p≤0.001 and **** for p≤0.0001.

Example 6. Dual-Fab Mode of Interaction is Required for Functional Antibody Binding Dual-Fab antibody binding, in cis-mode, of two identical Fabs to two different epitopes on a single protein is a novel, previously not observed, mode of antibody interaction. Combined with the fact that dual-Fab cis binding is connected with a clear gain in immunological protective function prompted us to verify this finding and elucidate the particular nature of Ab25s dual-Fab binding capacity. First, we investigated the ability of single Ab25 Fabs to obstruct Fc binding. If either binding site could sustain a steric hindrance of Fc binding, we should see a reduction. However, Fc binding was not affected by single Fabs (FIG. 25). Second, since Ab25 works well in ELISA (FIG. 7), we wanted to see if we could inhibit Ab25 binding with M1-based fragments (FIG. 38) lacking either binding site. If Ab25 could bind to the single epitopes on their own, it should be possible to reduce binding with the fragments. However, M1-binding was not affected by the fragments (FIG. 26), nor could we see binding to the fragments in a separate assay (FIG. 38). Third, we wanted to see how well different forms of the antibodies could bind to bacteria. We compared the binding of whole IgG, F(ab')2, and single Fabs to SF370. Strikingly, Ab25 single Fabs could not bind to the bacteria, whereas Ab49 Fabs increased their binding (FIG. 27). The latter is the expected result since single Fabs should have easier access and, yet the results reveal that Ab25's predominant mode of interaction with M protein is dual-Fab cis binding. To assess how much weaker the binding via single Fabs is, we performed affinity measurements of single Fabs. These showed that Ab25 Fab binding has a 2000-fold lower affinity (4.4 mM-1), compared to F(ab)'2 binding (2.3 $nM^{-1}$, FIG. 28). These results demonstrate that Ab25 requires a dual-Fab cis mode of interaction to bind effectively and exert a protective function.

What is claimed is:

1. An antibody binding to streptococcal M protein, wherein said antibody comprises:

a) a heavy chain comprising SEQ ID NO: 9; and b) a light chain comprising SEQ ID NO: 13.

2. The antibody according to claim 1, wherein the antibody binds to streptococcal M protein with a Kp of less than $50\times10^{-9}$ $M^{-1}$, as determined by binding to *Streptococcus pyogenes* SF370.

3. The antibody according to claim 1, wherein the antibody is configured to mediate bacterial agglutination.

4. The antibody according to claim 1, wherein the antibody is configured to mediate NFKB-activation.

5. The antibody according to claim 1, wherein the antibody is configured to induce phagocytosis.

6. A pharmaceutical composition comprising an antibody comprising:

a) a heavy chain comprising SEQ ID NO: 9; and b) a light chain comprising SEQ ID NO: 13;

and at least one pharmaceutically acceptable excipient.

7. A method of treating a Group A streptococcal infection, the method comprising administering an antibody comprising:

a) a heavy chain comprising SEQ ID NO: 9; and b) a light chain comprising SEQ ID NO: 13;

to a subject in need thereof.

* * * * *

SEQUENCE LISTING

<160> NUMBER OF SEQ ID NOS: 29

<210> SEQ ID NO 1
<211> LENGTH: 18
<212> TYPE: PRT
<213> ORGANISM: homo sapiens

<400> SEQUENCE: 1

Cys Ala Arg Ser Tyr Pro His Lys Arg Trp Leu Arg Pro Pro Phe Asp
1 5 10 15

Tyr Trp

<210> SEQ ID NO 2
<211> LENGTH: 18
<212> TYPE: PRT
<213> ORGANISM: homo sapiens

<400> SEQUENCE: 2

Cys Ala Lys Asn Ser Arg Ser Gly Trp Tyr Phe Phe Phe Asp Tyr Trp
1 5 10 15

Gly Gln

<210> SEQ ID NO 3
<211> LENGTH: 18
<212> TYPE: PRT
<213> ORGANISM: homo sapiens

<400> SEQUENCE: 3

Cys Ala Arg Gln Gly Phe Asp Thr Arg Gly Glu Asp Ala Phe Glu Ile
1 5 10 15

Trp Gly

<210> SEQ ID NO 4
<211> LENGTH: 18
<212> TYPE: PRT
<213> ORGANISM: homo sapiens

<400> SEQUENCE: 4

Cys Val Arg Asp Ser Arg Phe Trp Gly Ile Phe Asp Tyr Trp Gly Gln
1 5 10 15

Gly Thr

<210> SEQ ID NO 5
<211> LENGTH: 15
<212> TYPE: PRT
<213> ORGANISM: homo sapiens

<400> SEQUENCE: 5

Gln Tyr Asn Ser Tyr Pro Val Thr Phe Gly Gln Gly Thr Lys Val
1 5 10 15

<210> SEQ ID NO 6
<211> LENGTH: 15
<212> TYPE: PRT
<213> ORGANISM: homo sapiens

<400> SEQUENCE: 6

Gln Tyr Asp Asn Leu Pro Leu Thr Phe Gly Gly Gly Thr Lys Val
1 5 10 15

<210> SEQ ID NO 7
<211> LENGTH: 17

<212> TYPE: PRT
<213> ORGANISM: homo sapiens

<400> SEQUENCE: 7

Gln Arg Ser Gly Trp Pro Ser Ile Phe Thr Phe Gly Pro Gly Thr Lys
1               5                   10                  15

Val

<210> SEQ ID NO 8
<211> LENGTH: 15
<212> TYPE: PRT
<213> ORGANISM: homo sapiens

<400> SEQUENCE: 8

Gln Arg Ser Asn Trp Pro Pro Thr Phe Gly Gln Gly Thr Lys Val
1               5                   10                  15

<210> SEQ ID NO 9
<211> LENGTH: 122
<212> TYPE: PRT
<213> ORGANISM: homo sapiens

<400> SEQUENCE: 9

Val Gln Leu Val Glu Ser Gly Gly Gly Val Val Gln Pro Gly Arg Ser
1               5                   10                  15

Leu Arg Leu Ser Cys Ala Ala Ser Gly Phe Thr Phe Ser Ser Tyr Ala
            20                  25                  30

Met His Trp Val Arg Gln Ala Pro Gly Lys Gly Leu Glu Trp Val Ala
        35                  40                  45

Leu Ile Ser Tyr Asp Gly Arg Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Tyr Pro His Lys Arg Trp Leu Arg Pro Pro Phe Asp Tyr Trp
            100                 105                 110

Gly Gln Gly Thr Leu Val Thr Val Ser Ser
        115                 120

<210> SEQ ID NO 10
<211> LENGTH: 112
<212> TYPE: PRT
<213> ORGANISM: homo sapiens

<400> SEQUENCE: 10

Val Gln Leu Val Glu Ser Gly Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30

Met His Trp Val Arg Gln Ala Pro Gly Lys Gly Leu Glu Trp Val Ala
        35                  40                  45

Val Ile Ser Tyr Asp Gly Asn Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Arg Ala Glu Asp Thr Ala Val Tyr Tyr Cys Ala
                85                  90                  95

```
Lys Asn Ser Arg Ser Gly Trp Tyr Phe Phe Phe Asp Tyr Trp Gly Gln
            100                 105                 110


<210> SEQ ID NO 11
<211> LENGTH: 121
<212> TYPE: PRT
<213> ORGANISM: homo sapiens

<400> SEQUENCE: 11

Val Gln Leu Val Glu Ser Gly Gly Gly Leu Val Arg Pro Gly Gly Ser
1               5                   10                  15

Leu Arg Leu Ser Cys Val Ala Ser Gly Phe Met Phe Asn Glu Tyr Tyr
            20                  25                  30

Met Ser Trp Ile Arg Gln Ala Pro Gly Lys Gly Leu Glu Trp Ile Ser
        35                  40                  45

Phe Ile Ser Asn Ala Gly Thr Tyr Thr Asn Tyr Ala Glu Ser Val Lys
    50                  55                  60

Gly Arg Phe Thr Ile Ser Arg Asp Asn Ala Lys Asp Ser Leu Tyr Leu
65                  70                  75                  80

Glu Met Asn Ser Leu Arg Gly Glu Asp Thr Ala Val Tyr Tyr Cys Ala
                85                  90                  95

Arg Gln Gly Phe Asp Thr Arg Gly Glu Asp Ala Phe Glu Ile Trp Gly
            100                 105                 110

Gln Gly Thr Met Val Thr Val Ser Ser
        115                 120


<210> SEQ ID NO 12
<211> LENGTH: 118
<212> TYPE: PRT
<213> ORGANISM: homo sapiens

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ile Asn
            20                  25                  30

Tyr Met Ser Trp Val Arg Gln Ala Pro Gly Lys Gly Leu Gln Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Met Tyr Tyr Cys Val
                85                  90                  95

Arg Asp Ser Arg Phe Trp Gly Ile Phe Asp Tyr Trp Gly Gln Gly Thr
            100                 105                 110

Leu Val Thr Val Ser Ser
        115


<210> SEQ ID NO 13
<211> LENGTH: 107
<212> TYPE: PRT
<213> ORGANISM: homo sapiens

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
```

```
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Cys Cys Gln Gln Tyr Asn Ser Tyr Pro Val
                85                  90                  95

Thr Phe Gly Gln Gly Thr Lys Val Asp Ile Lys
            100                 105


<210> SEQ ID NO 14
<211> LENGTH: 107
<212> TYPE: PRT
<213> ORGANISM: homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105


<210> SEQ ID NO 15
<211> LENGTH: 109
<212> TYPE: PRT
<213> ORGANISM: homo sapiens

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Pro Leu Ser Gly Tyr
            20                  25                  30

Leu Ala Trp Tyr Gln Gln Lys Pro Gly Gln Ala Pro Arg Leu Leu Ile
        35                  40                  45

Tyr Asn Ala Ser Lys Arg Ala Thr Gly Ile Pro Ala Arg Phe Thr Gly
    50                  55                  60

Ser Gly Ser Gly Thr Asp Phe Thr Leu Thr Ile Ser Ser Leu Glu Ser
65                  70                  75                  80

Glu Asp Phe Ala Val Tyr Tyr Cys Gln Gln Arg Ser Gly Trp Pro Ser
                85                  90                  95

Ile Phe Thr Phe Gly Pro Gly Thr Lys Val Asp Ile Lys
            100                 105


<210> SEQ ID NO 16
<211> LENGTH: 107
<212> TYPE: PRT
```

<213> ORGANISM: homo sapiens

<400> SEQUENCE: 16

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Arg Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 17
<211> LENGTH: 472
<212> TYPE: PRT
<213> ORGANISM: homo sapiens

<400> SEQUENCE: 17

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Ala Met His Trp Val Arg Gln Ala Pro Gly Lys Gly Leu
    50                  55                  60

Glu Trp Val Ala Leu Ile Ser Tyr Asp Gly Arg Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ser Tyr Pro His Lys Arg Trp Leu Arg Pro Pro
        115                 120                 125

Phe Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
```

```
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470


<210> SEQ ID NO 18
<211> LENGTH: 470
<212> TYPE: PRT
<213> ORGANISM: homo sapien

<400> SEQUENCE: 18

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Ser Tyr Asp Gly Asn Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Val Asn Ser Leu Arg Ala Glu Asp Thr Ala Val
            100                 105                 110

Tyr Tyr Cys Ala Lys Asn Ser Arg Ser Gly Trp Tyr Phe Phe Phe Asp
        115                 120                 125

Tyr Trp Gly Gln Gly Thr Leu Val Thr Val Ser Ser Ala Ser Thr Lys
    130                 135                 140
```

```
Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

```
<210> SEQ ID NO 19
<211> LENGTH: 471
<212> TYPE: PRT
<213> ORGANISM: homo sapien

<400> SEQUENCE: 19

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Arg
            20                  25                  30

Pro Gly Gly Ser Leu Arg Leu Ser Cys Val Ala Ser Gly Phe Met Phe
        35                  40                  45
```

```
Asn Glu Tyr Tyr Met Ser Trp Ile Arg Gln Ala Pro Gly Lys Gly Leu
    50                  55                  60

Glu Trp Ile Ser Phe Ile Ser Asn Ala Gly Thr Tyr Thr Asn Tyr Ala
65                  70                  75                  80

Glu Ser Val Lys Gly Arg Phe Thr Ile Ser Arg Asp Asn Ala Lys Asp
                85                  90                  95

Ser Leu Tyr Leu Glu Met Asn Ser Leu Arg Gly Glu Asp Thr Ala Val
            100                 105                 110

Tyr Tyr Cys Ala Arg Gln Gly Phe Asp Thr Arg Gly Glu Asp Ala Phe
        115                 120                 125

Glu Ile Trp Gly Gln Gly Thr Met Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460
```

```
Leu Ser Leu Ser Pro Gly Lys
465                 470


<210> SEQ ID NO 20
<211> LENGTH: 467
<212> TYPE: PRT
<213> ORGANISM: homo sapien

<400> SEQUENCE: 20

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Val
        35                  40                  45

Ser Ile Asn Tyr Met Ser Trp Val Arg Gln Ala Pro Gly Lys Gly Leu
    50                  55                  60

Gln Trp Val Ser Val Ile Tyr Ser Gly Gly Ser Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Met Tyr
            100                 105                 110

Tyr Cys Val Arg Asp Ser Arg Phe Trp Gly Ile Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

```
Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 21
<211> LENGTH: 233
<212> TYPE: PRT
<213> ORGANISM: homo sapien

<400> SEQUENCE: 21

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Thr Leu Ser Ala
            20                  25                  30

Ser Val Gly Asp Arg Val Thr Ile Thr Cys Arg Ala Ser Gln Ser Ile
        35                  40                  45

Ser Ser Trp Leu Ala Trp Tyr Gln Gln Lys Pro Gly Lys Ala Pro Lys
    50                  55                  60

Leu Leu Ile Tyr Asp Ala Ser Ser Leu Glu Ser Gly Val Pro Ser Arg
65                  70                  75                  80

Phe Ser Gly Ser Gly Ser Gly Thr Glu Phe Thr Leu Thr Ile Ser Ser
                85                  90                  95

Leu Gln Pro Asp Asp Phe Ala Ser Tyr Cys Cys Gln Gln Tyr Asn Ser
            100                 105                 110

Tyr Pro Val Thr Phe Gly Gln Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 22
<211> LENGTH: 233
<212> TYPE: PRT

<213> ORGANISM: homo sapien

<400> SEQUENCE: 22

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Gln Ala Ser Gln Asp Ile
        35                  40                  45

Ser Asn Tyr Leu Asn Trp Tyr Gln Gln Lys Pro Gly Lys Ala Pro Lys
    50                  55                  60

Leu Leu Ile Tyr Asp Ala Ser Asn Leu Glu Thr Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Tyr Asp Asn
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 23
<211> LENGTH: 235
<212> TYPE: PRT
<213> ORGANISM: homo sapiens

<400> SEQUENCE: 23

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Pro Leu
        35                  40                  45

Ser Gly Tyr Leu Ala Trp Tyr Gln Gln Lys Pro Gly Gln Ala Pro Arg
    50                  55                  60

Leu Leu Ile Tyr Asn Ala Ser Lys Arg Ala Thr Gly Ile Pro Ala Arg
65                  70                  75                  80

Phe Thr Gly Ser Gly Ser Gly Thr Asp Phe Thr Leu Thr Ile Ser Ser
                85                  90                  95

Leu Glu Ser Glu Asp Phe Ala Val Tyr Tyr Cys Gln Gln Arg Ser Gly
            100                 105                 110

Trp Pro Ser Ile Phe Thr Phe Gly Pro Gly Thr Lys Val Asp Ile Lys
```

```
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 24
<211> LENGTH: 233
<212> TYPE: PRT
<213> ORGANISM: homo sapiens

<400> SEQUENCE: 24

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Ser Ser Tyr Leu Ala Trp Tyr Gln Arg Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 25
<211> LENGTH: 65
```

<212> TYPE: PRT
<213> ORGANISM: Group A Streptococcus

<400> SEQUENCE: 25

```
Ala Thr Ala Leu Glu Lys Glu Leu Glu Glu Lys Lys Glu Ala Leu Glu
1               5                   10                  15

Leu Ala Ile Asp Gln Ala Ser Arg Asp Tyr His Arg Ala Thr Ala Leu
            20                  25                  30

Glu Lys Glu Leu Glu Glu Lys Lys Lys Ala Leu Glu Leu Ala Ile Asp
        35                  40                  45

Gln Ala Ser Gln Asp Tyr Asn Arg Ala Asn Val Leu Glu Lys Glu Leu
    50                  55                  60

Glu
65
```

<210> SEQ ID NO 26
<211> LENGTH: 120
<212> TYPE: PRT
<213> ORGANISM: Group A Streptococcus

<400> SEQUENCE: 26

```
Ala Lys Leu Glu Glu Glu Lys Gln Ile Ser Asp Ala Ser Arg Gln Ser
1               5                   10                  15

Leu Arg Arg Asp Leu Asp Ala Ser Arg Glu Ala Lys Lys Gln Val Glu
            20                  25                  30

Lys Asp Leu Ala Asn Leu Thr Ala Glu Leu Asp Lys Val Lys Glu Asp
        35                  40                  45

Lys Gln Ile Ser Asp Ala Ser Arg Gln Gly Leu Arg Arg Asp Leu Asp
    50                  55                  60

Ala Ser Arg Glu Ala Lys Lys Gln Val Glu Lys Asp Leu Ala Asn Leu
65                  70                  75                  80

Thr Ala Glu Leu Asp Lys Val Lys Glu Glu Lys Gln Ile Ser Asp Ala
                85                  90                  95

Ser Arg Gln Gly Leu Arg Arg Asp Leu Asp Ala Ser Arg Glu Ala Lys
            100                 105                 110

Lys Gln Val Glu Lys Ala Leu Glu
        115                 120
```

<210> SEQ ID NO 27
<211> LENGTH: 444
<212> TYPE: PRT
<213> ORGANISM: Group A Streptococcus

<400> SEQUENCE: 27

```
Met Asp Gly Asn Pro Arg Glu Val Ile Glu Asp Leu Ala Ala Asn Asn
1               5                   10                  15

Pro Ala Ile Gln Asn Ile Arg Leu Arg Tyr Glu Asn Lys Asp Leu Lys
            20                  25                  30

Ala Arg Leu Glu Asn Ala Met Glu Val Ala Gly Arg Asp Phe Lys Arg
        35                  40                  45

Ala Glu Glu Leu Glu Lys Ala Lys Gln Ala Leu Glu Asp Gln Arg Lys
    50                  55                  60

Asp Leu Glu Thr Lys Leu Lys Glu Leu Gln Gln Asp Tyr Asp Leu Ala
65                  70                  75                  80

Lys Glu Ser Thr Ser Trp Asp Arg Gln Arg Leu Glu Lys Glu Leu Glu
                85                  90                  95

Glu Lys Lys Glu Ala Leu Glu Leu Ala Ile Asp Gln Ala Ser Arg Asp
```

```
            100                 105                 110

Tyr His Arg Ala Thr Ala Leu Glu Lys Glu Leu Glu Glu Lys Lys Lys
        115                 120                 125

Ala Leu Glu Leu Ala Ile Asp Gln Ala Ser Gln Asp Tyr Asn Arg Ala
    130                 135                 140

Asn Val Leu Glu Lys Glu Leu Glu Thr Ile Thr Arg Glu Gln Glu Ile
145                 150                 155                 160

Asn Arg Asn Leu Leu Gly Asn Ala Lys Leu Glu Leu Asp Gln Leu Ser
                165                 170                 175

Ser Glu Lys Glu Gln Leu Thr Ile Glu Lys Ala Lys Leu Glu Glu Glu
            180                 185                 190

Lys Gln Ile Ser Asp Ala Ser Arg Gln Ser Leu Arg Arg Asp Leu Asp
        195                 200                 205

Ala Ser Arg Glu Ala Lys Lys Gln Val Glu Lys Asp Leu Ala Asn Leu
    210                 215                 220

Thr Ala Glu Leu Asp Lys Val Lys Glu Asp Lys Gln Ile Ser Asp Ala
225                 230                 235                 240

Ser Arg Gln Gly Leu Arg Arg Asp Leu Asp Ala Ser Arg Glu Ala Lys
                245                 250                 255

Lys Gln Val Glu Lys Asp Leu Ala Asn Leu Thr Ala Glu Leu Asp Lys
            260                 265                 270

Val Lys Glu Glu Lys Gln Ile Ser Asp Ala Ser Arg Gln Gly Leu Arg
        275                 280                 285

Arg Asp Leu Asp Ala Ser Arg Glu Ala Lys Lys Gln Val Glu Lys Ala
    290                 295                 300

Leu Glu Glu Ala Asn Ser Lys Leu Ala Ala Leu Glu Lys Leu Asn Lys
305                 310                 315                 320

Glu Leu Glu Glu Ser Lys Lys Leu Thr Glu Lys Glu Lys Glu Lys Ala
                325                 330                 335

Glu Leu Gln Ala Lys Leu Glu Ala Glu Ala Lys Ala Leu Lys Glu Gln
            340                 345                 350

Leu Ala Lys Gln Ala Glu Glu Leu Ala Lys Leu Arg Ala Gly Lys Ala
        355                 360                 365

Ser Asp Ser Gln Thr Pro Asp Thr Lys Pro Gly Asn Lys Ala Val Pro
    370                 375                 380

Gly Lys Gly Gln Ala Pro Gln Ala Gly Thr Lys Pro Asn Gln Asn Lys
385                 390                 395                 400

Ala Pro Met Lys Glu Thr Lys Arg Gln Leu Pro Ser Thr Gly Glu Thr
                405                 410                 415

Ala Asn Pro Phe Phe Thr Ala Ala Ala Leu Thr Val Met Ala Thr Ala
            420                 425                 430

Gly Val Ala Ala Val Val Lys Arg Lys Glu Glu Asn
        435                 440
```

<210> SEQ ID NO 28
<211> LENGTH: 18
<212> TYPE: PRT
<213> ORGANISM: homo sapien
<220> FEATURE:
<221> NAME/KEY: MISC_FEATURE
<222> LOCATION: (2)..(2)
<223> OTHER INFORMATION: A or V
<220> FEATURE:
<221> NAME/KEY: MISC_FEATURE
<222> LOCATION: (3)..(3)
<223> OTHER INFORMATION: R or K
<220> FEATURE:

```
<221> NAME/KEY: MISC_FEATURE
<222> LOCATION: (4)..(4)
<223> OTHER INFORMATION: S, N, Q or D
<220> FEATURE:
<221> NAME/KEY: MISC_FEATURE
<222> LOCATION: (5)..(5)
<223> OTHER INFORMATION: Y, S, G, or absent
<220> FEATURE:
<221> NAME/KEY: MISC_FEATURE
<222> LOCATION: (6)..(6)
<223> OTHER INFORMATION: P, F, or absent
<220> FEATURE:
<221> NAME/KEY: MISC_FEATURE
<222> LOCATION: (7)..(7)
<223> OTHER INFORMATION: H, R, D, or absent
<220> FEATURE:
<221> NAME/KEY: MISC_FEATURE
<222> LOCATION: (8)..(8)
<223> OTHER INFORMATION: K, S, or T
<220> FEATURE:
<221> NAME/KEY: MISC_FEATURE
<222> LOCATION: (9)..(9)
<223> OTHER INFORMATION: R or G
<220> FEATURE:
<221> NAME/KEY: MISC_FEATURE
<222> LOCATION: (10)..(10)
<223> OTHER INFORMATION: W, G, or F
<220> FEATURE:
<221> NAME/KEY: MISC_FEATURE
<222> LOCATION: (10)..(10)
<223> OTHER INFORMATION: W, G, or F
<220> FEATURE:
<221> NAME/KEY: MISC_FEATURE
<222> LOCATION: (11)..(11)
<223> OTHER INFORMATION: L, Y, E, or W
<220> FEATURE:
<221> NAME/KEY: MISC_FEATURE
<222> LOCATION: (12)..(12)
<223> OTHER INFORMATION: R or absent
<220> FEATURE:
<221> NAME/KEY: MISC_FEATURE
<222> LOCATION: (13)..(13)
<223> OTHER INFORMATION: P, F, D, or G
<220> FEATURE:
<221> NAME/KEY: MISC_FEATURE
<222> LOCATION: (14)..(14)
<223> OTHER INFORMATION: P, F, A, or I
<220> FEATURE:
<221> NAME/KEY: MISC_FEATURE
<222> LOCATION: (15)..(15)
<223> OTHER INFORMATION: F, A
<220> FEATURE:
<221> NAME/KEY: MISC_FEATURE
<222> LOCATION: (16)..(16)
<223> OTHER INFORMATION: D or E
<220> FEATURE:
<221> NAME/KEY: MISC_FEATURE
<222> LOCATION: (17)..(17)
<223> OTHER INFORMATION: Y or I

<400> SEQUENCE: 28

Cys Xaa Xaa Xaa Xaa Xaa Xaa Xaa Xaa Xaa Xaa Xaa Xaa Xaa Xaa Xaa
1               5                   10                  15

Xaa Trp


<210> SEQ ID NO 29
<211> LENGTH: 17
<212> TYPE: PRT
<213> ORGANISM: homo sapien
<220> FEATURE:
<221> NAME/KEY: MISC_FEATURE
<222> LOCATION: (2)..(2)
<223> OTHER INFORMATION: Y or R
<220> FEATURE:
<221> NAME/KEY: MISC_FEATURE
<222> LOCATION: (3)..(3)
```

-continued

```
<223> OTHER INFORMATION: N, D, or S
<220> FEATURE:
<221> NAME/KEY: MISC_FEATURE
<222> LOCATION: (4)..(4)
<223> OTHER INFORMATION: S, N, or G
<220> FEATURE:
<221> NAME/KEY: MISC_FEATURE
<222> LOCATION: (5)..(5)
<223> OTHER INFORMATION: Y, L, or W
<220> FEATURE:
<221> NAME/KEY: MISC_FEATURE
<222> LOCATION: (7)..(7)
<223> OTHER INFORMATION: V, L, S, or P
<220> FEATURE:
<221> NAME/KEY: MISC_FEATURE
<222> LOCATION: (8)..(8)
<223> OTHER INFORMATION: I or absent
<220> FEATURE:
<221> NAME/KEY: MISC_FEATURE
<222> LOCATION: (9)..(9)
<223> OTHER INFORMATION: F or absent
<220> FEATURE:
<221> NAME/KEY: MISC_FEATURE
<222> LOCATION: (13)..(13)
<223> OTHER INFORMATION: Q, G, or P

<400> SEQUENCE: 29

Gln Xaa Xaa Xaa Xaa Pro Xaa Xaa Xaa Thr Phe Gly Xaa Gly Thr Lys
1               5                   10                  15

Val
```